United States Patent
Shusta et al.

(10) Patent No.: US 12,077,609 B2
(45) Date of Patent: Sep. 3, 2024

(54) VARIABLE LYMPHOCYTE RECEPTORS THAT TARGET THE BRAIN EXTRACELLULAR MATRIX AND METHODS OF USE

(71) Applicants: Wisconsin Alumni Research Foundation, Madison, WI (US); Emory University, Atlanta, GA (US)

(72) Inventors: Eric V. Shusta, Madison, WI (US); Benjamin Umlauf, Madison, WI (US); Brantley Herrin, Atlanta, GA (US); Paul Clark, Madison, WI (US); John Kuo, Austin, TX (US)

(73) Assignees: WISCONSIN ALUMNI RESEARCH FOUNDATION, Madison, WI (US); EMORY UNIVERSITY, Atlanta, GA (US)

( * ) Notice: Subject to any disclaimer, the term of this patent is extended or adjusted under 35 U.S.C. 154(b) by 247 days.

(21) Appl. No.: 17/414,581

(22) PCT Filed: Dec. 19, 2019

(86) PCT No.: PCT/US2019/067579
§ 371 (c)(1),
(2) Date: Jun. 16, 2021

(87) PCT Pub. No.: WO2020/132301
PCT Pub. Date: Jun. 25, 2020

(65) Prior Publication Data
US 2022/0041659 A1 Feb. 10, 2022

Related U.S. Application Data

(60) Provisional application No. 62/783,475, filed on Dec. 21, 2018.

(51) Int. Cl.
| | | |
|---|---|---|
| C07K 7/08 | (2006.01) | |
| A61K 38/00 | (2006.01) | |
| A61K 45/06 | (2006.01) | |
| A61P 35/00 | (2006.01) | |
| C07K 7/06 | (2006.01) | |
| C12N 15/86 | (2006.01) | |

(52) U.S. Cl.
CPC ............... *C07K 7/08* (2013.01); *A61K 45/06* (2013.01); *A61P 35/00* (2018.01); *C07K 7/06* (2013.01); *C12N 15/86* (2013.01); *A61K 38/00* (2013.01)

(58) Field of Classification Search
None
See application file for complete search history.

(56) References Cited

U.S. PATENT DOCUMENTS

| | | |
|---|---|---|
| 8,039,588 B2 | 10/2011 | Pancer et al. |
| 8,212,018 B2 | 7/2012 | Pancer et al. |
| 9,127,087 B2 | 9/2015 | Pancer et al. |
| 10,036,747 B2 | 7/2018 | Pancer et al. |
| 2017/0081385 A1 | 3/2017 | Herrin et al. |
| 2022/0204583 A1 | 6/2022 | Shusta et al. |

FOREIGN PATENT DOCUMENTS

| | | |
|---|---|---|
| WO | 2006083275 A2 | 8/2006 |
| WO | 2013078425 A1 | 5/2013 |
| WO | 2015168469 A1 | 11/2015 |
| WO | 2015174869 A1 | 11/2015 |

OTHER PUBLICATIONS

Waters and Shusta. "The variable lymphocyte receptor as an antibody alternative." Curr Opin Biotechnol. Aug. 2018; 52:74-79.
Wolak, R. G. Thorne, Diffusion of macromolecules in the brain: Implications for drug delivery. Mol. Pharm. 10, 1492-1504 (2013).
Woodworth, G. P. Dunn, E. A. Nance, J. Hanes, H. Brem, Emerging insights into barriers to effective brain tumor therapeutics. Front. Oncol. 4, 126 (2014).
Wu A M, Senter P D, Arming antibodies: prospects and challenges for immunoconjugates, Nat Biotechnol. Sep. 2005; 23(9):1137-46.
Zlokovic et al., "Strategies to Circumvent Vascular Barriers of the Central Nervous System," Neurosurgery, (1998).
Abbott,N. J., A. A. K. Patabendige, D. E. M. Dolman, S. R. Yusof, D. J. Begley, Structure and function of the blood-brain barrier. Neurobiol. Dis. 37, 13-25 (2010).
Alavi et al. "Application of Various Types of Liposomes in Drug Delivery Systems" Adv. Pharm Bull Apr. 2017:7(1):3-9.
Allen and Cullis "Liposomal drug delivery systems: From concept to clinical applications" Advanced Drug Delivery Reviews, 65:1 (Jan. 2013) pp. 36-48.
Brown, B. Badie, M. E. Barish, L. Weng, J. R. Ostberg, W.-C. Chang, A. Naranjo, R. Starr, J. Wagner, C. Wright, Y. Zhai, J. R. Bading, J. A. Ressler, J. Portnow, M. D'Apuzzo, S. J. Forman, M. C. Jensen, Bioactivity and safety of IL13Rα2-redirected chimeric antigen receptor CD8+ T cells in patients with recurrent glioblastoma. Clin. Cancer Res. 21, 4062-4072 (2015).
Brown, D. Alizadeh, R. Starr, L. Weng, J. R. Wagner, A. Naranjo, J. R. Ostberg, M. S. Blanchard, J. Kilpatrick, J. Simpson, A. Kurien, S. J. Priceman, X. Wang, T. L. Harshbarger, M. D'Apuzzo, J. A. Ressler, M. C. Jensen, M. E. Barish, M. Chen, J. Portnow, S. J. Forman, B. Badie, Regression of glioblastoma after chimeric antigen receptor T-cell therapy. N. Engl. J. Med. 375, 2561-2569 (2016).
Brown, Peptidic tumor targeting agents: The road from phage display peptide selections to clinical applications. Curr. Pharm. Des. 16, 1040-1054 (2010).

(Continued)

*Primary Examiner* — Thomas S Heard
(74) *Attorney, Agent, or Firm* — Quarles & Brady, LLP

(57) ABSTRACT

The present disclosure provides isolated polypeptides comprising variable lymphocyte receptors that specifically bind the brain extracellular matrix, compositions, and methods of use. Methods of using the variable lymphocyte receptors for the detection and treatment of disease or injury, specifically, for example, cancers including glioblastoma are provided.

30 Claims, 15 Drawing Sheets

Specification includes a Sequence Listing.

(56) References Cited

OTHER PUBLICATIONS

Burns, T. M. Malott, K. J. Metcalf, B. J. Hackel, J. R. Chan, E. V. Shusta, Directed evolution of brain-derived neurotrophic factor for improved folding and expression in *Saccharomyces cerevisiae*. Appl. Environ. Microbiol. 80, 5732-5742 (2014).

Clark et al. "Neurovascular-targeting antibodies discovered using yeast biopanning enhance drug delivery and improve survival for glioblastoma," Cancer Res (2018) 78 (13_Supplement): 1764. (Abstract).

Etame, R. J. Diaz, C. A. Smith, T. G. Mainprize, H. K. Hynynen, J. T. Rutka, Focused ultrasound disruption of the blood brain barrier: A new frontier for therapeutic delivery in molecular neuro-oncology. Neurosurg. Focus 1, E3 (2012).

Gray, M. J. McGuire, K. C. Brown, A liposomal drug platform overrides peptide ligand targeting to a cancer biomarker, irrespective of ligand affinity or density. PLOS One 8, e72938 (2013).

Groothuis, The blood-brain and blood-tumor barriers: A review of strategies for increasing drug delivery. Neuro Oncol. 2, 45-59 (2000).

Guo, M. Hirano, B. R. Herrin, J. Li, C. Yu, A. Sadlonova, M. D. Cooper, Dual nature of the adaptive immune system in lampreys. Nature 459, 796-801 (2009).

Gupta, V. P. Torchilin, Monoclonal antibody 2C5-modified doxorubicin-loaded liposomes with significantly enhanced therapeutic activity against intracranial human brain U-87 MG tumor xenografts in nude mice. Cancer Immunol. Immunother. 56, 1215-1223 (2007).

Han, B. R. Herrin, M. D. Cooper, I. A. Wilson, Antigen recognition by variable lymphocyte receptors. Science 321, 1834-1837 (2008).

Herrin et al., "Structure and specificity of lamprey monoclonal antibodies," Proc Natl Acad Sci U S A Feb. 12, 2008;105(6):2040-5.

Herrin, M. D. Cooper, Alternative adaptive immunity in jawless vertebrates. J. Immunol. 185, 1367-1374 (2010).

Holodinsky, A. Y. X. Yu, Z. A. Assis, A. S. Al Sultan, B. K. Menon, A. M. Demchuk, M. Goyal, M. D. Hill, History, evolution, and importance of emergency endovascular treatment of acute ischemic stroke. Curr. Neurol. Neurosci. Rep. 16, 42 (2016).

Hong, M. Z. Ma, J. C. Gildersleeve, S. Chowdhury, J.J. BarchiJr., R. A. Mariuzza, M. B. Murphy, L. Mao, Z. Pancer, Sugar-binding proteins from fish: Selection of high affinity "lambodies" that recognize biomedically relevant glycans. ACS Chem. Biol. 8, 152-160 (2013).

Hwang, J.-H. Ryou, J. R. Oh, J. W. Han, T. K. Park, H.-S. Kim, Anti-human VEGF repebody effectively suppresses choroidal neovascularization and vascular leakage. PLOS One 11, e0152522 (2016).

International Search Report and Written Opinion for corresponding PCT/US2019/067579, mailed May 8, 2020.

Kasahara et al., "Two Forms of Adaptive Immunity in Vertebrates: Similarities and Differences." Adv in Immunol. (2014).

Kim, A. Rait, E. Kim, J. DeMarco, K. F. Pirollo, E. H. Chang, Encapsulation of temozolomide in a tumor-targeting nanocomplex enhances anti-cancer efficacy and reduces toxicity in a mouse model of glioblastoma. Cancer Lett. 369, 250-258 (2015).

Kuznetsov, R. K. Puri, Kinetic analysis of high affinity forms of interleukin (IL)-13 receptors: Suppression of IL-13 binding by IL-2 receptor gamma chain. Biophys. J. 77, 154-172 (1999).

Lajoie, "Application of yeast surface display screening methods to antibody discovery and proteomics of the blood-brain barrier," thesis, University of WisconsinMadison (2016).

Lamsam, E. Johnson, I. D. Connolly, M. Wintermark, M. Hayden Gephart, A review of potential applications of MR-guided focused ultrasound for targeting brain tumor therapy. Neurosurg. Focus 44, E10 (2018).

Lee, H. J. Kim, C.-S. Yang, H.-H. Kyeong, J.-M. Choi, D.-E. Hwang, J.-M. Yuk, K. Park, Y. J. Kim, S.-G. Lee, D. Kim, E.-K. Jo, H.-K. Cheong, H.-S. Kim, A high-affinity protein binder that blocks the IL-6/STAT3 signaling pathway effectively suppresses non-small cell lung cancer. Mol. Ther. 22, 1254-1265 (2014).

Lockman, R. K. Mittapalli, K. S. Taskar, V. Rudraraju, B. Gril, K. A. Bohn, C. E. Adkins, A. Roberts, H. R. Thorsheim, J. A. Gaasch, S. Huang, D. Palmieri, P. S. Steeg, Q. R. Smith, Heterogeneous blood-tumor barrier permeability determines drug efficacy in experimental brain metastases of breast cancer. Clin. Cancer Res. 16, 5664-5678 (2010).

Madhankumar, B. Slagle-Webb, X. Wang, Q. X. Yang, D. A. Antonetti, P. A. Miller, J. M. Sheehan, J. R. Connor, Efficacy of interleukin-13 receptor-targeted liposomal doxorubicin in the intracranial brain tumor model. Mol. Cancer Ther. 8, 648-654 (2009).

Mann, P. Scodeller, S. Hussain, J. Joo, E. Kwon, G. B. Braun, T. Mölder, Z.-G. She, V. R. Kotamraju, B. Ranscht, S. Krajewski, T. Teesalu, S. Bhatia, M. J. Sailor, E. Ruoslahti, A peptide for targeted, systemic delivery of imaging and therapeutic compounds into acute brain injuries. Nat. Commun. 7, 11980 (2016).

Marshall, V. A. Grosskopf, T. J. Moehling, B. J. Tillotson, G. J. Wiepz, N. L. Abbott, R. T. Raines, E. V. Shusta, An evolved Mxe GyrA intein for enhanced production of fusion proteins. ACS Chem. Biol. 10, 527-538 (2015).

McCaffrey,G., T. P. Davis, Physiology and pathophysiology of the blood-brain barrier: P-glycoprotein and occludin trafficking as therapeutic targets to optimize central nervous system drug delivery. J. Invest. Med. 60, 1131-1140 (2012).

McCarty, J. DiRosario, K. Gulaid, J. Muenzer, H. Fu, Mannitol-facilitated CNS entry of rAAV2 vector significantly delayed the neurological disease progression in MPS IIIB mice. Gene Ther. 16, 1340-1352 (2009).

Minagar, J. S. Alexander, Blood-brain barrier disruption in multiple sclerosis. Mult. Scler. 9, 540-549 (2003).

Nance, K. Timbie, G. W. Miller, J. Song, C. Louttit, A. L. Klibanov, T.-Y. Shih, G. Swaminathan, R. J. Tamargo, G. F. Woodworth, J. Hanes, R. J. Price, Non-invasive delivery of stealth, brain-penetrating nanoparticles across the blood-brain barrier using MRI-guided focused ultrasound. J. Control. Release 189, 123-132 (2014).

Nico, D. Ribatti, Morphofunctional aspects of the blood-brain barrier. Curr. Drug Metab. 13, 50-60 (2012).

Obermeier, A. Verma, R. M. Ransohoff, The blood-brain barrier. Handb. Clin. Neurol. 133, 39-59 (2016).

Oh, S. Fakurnejad, E. T. Sayegh, A. J. Clark, M. E. Ivan, M. Z. Sun, M. Safaee, O. Bloch, C. D. James, A. T. Parsa, Immunocompetent murine models for the study of glioblastoma immunotherapy. J. Transl. Med. 12, 107 (2014).

Ostrom, H.Gittleman, J. Fulop, M. Liu, R. Blanda, C. Kromer, Y. Wolinsky, C. Kruchko, J. S. Barnholtz-Sloan, CBTRUS statistical report: Primary brain and central nervous system tumors diagnosed in the united states in 2008-2012. Neuro Oncol. 17 Suppl 4, iv1-iv62 (2015).

Pellegatta, B. Savoldo, N. Di Ianni, C. Corbetta, Y. Chen, M. Patané, C. Sun, B. Pollo, S. Ferrone, F. DiMeco, G. Finocchiaro, G. Dotti, Constitutive and TNF□-inducible expression of chondroitin sulfate proteoglycan 4 in glioblastoma and neurospheres: Implications for CAR-T cell therapy. Sci. Transl. Med. 10, eaao2731 (2018).

Preusser, M. Lim, D. A. Hafler, D. A. Reardon, J. H. Sampson, Prospects of immune checkpoint modulators in the treatment of glioblastoma. Nat. Rev. Neurol. 11, 504-514 (2015).

Saito G, Swanson JA, Lee K D. Drug delivery strategy utilizing conjugation via reversible disulfide linkages: role and site of cellular reducing activities, Adv Drug Deliv Rev. Feb. 2003. 10; 55(2):199-215.

Shi et al., "Rapid endothelial cytoskeletal reorganization enables early blood-brain barrier disruption and long-term ischaemic reperfusion brain injury," Nat Commun. Jan. 2, 20167;7:10523.

Steiner, P. Forrer, A. Plückthun, Efficient selection of DARPins with sub-nanomolar affinities using SRP phage display. J. Mol. Biol. 382, 1211-1227 (2008).

Sugano et al., Antibody Targeting of Doxorubicin-loaded Liposomes Suppresses the Growth and Metastatic Spread of Established Human Lung Tumor Xenografts in Severe Combined Immunodeficient Mice Cancer Research 60, 6942-6949, Dec. 15, 2000.

Sukhanova et al., "Oriented conjugates of single-domain antibodies and quantum dots: toward a new generation of ultrasmall diagnostic nanoprobes," Nanomedicine 8(4): 516-525, 2012.

(56) References Cited

OTHER PUBLICATIONS

Swanson, P. A. Clark, R. R. Zhang, I. K. Kandela, M. Farhoud, J. P. Weichert, J. S. Kuo, Fluorescent cancer-selective alkylphosphocholine analogs for intraoperative glioma detection. Neurosurgery 76, 115-124 (2015).

Trail P A, King H D, Dubowchik G M, Monoclonal antibody drug immunoconjugates for targeted treatment of cancer, Cancer Immunol Immunother. May 2003; 52(5):328-37.

Umlauf, "Identification and Development of Variable Lymphocyte Targeting Ligands for Glioblastoma," PEGS Boston, 2018. Presented May 2, 2018.

Umlauf, K. A. Mix, V. A.Grosskopf, R. T. Raines, E. V. Shusta, Site-specific antibody functionalization using tetrazine-styrene cycloaddition. Bioconjug. Chem. 29, 1605-1613 (2018).

Van De Broek et al., "Specific cell targeting with nanobody conjugated branched gold nanoparticles for photothermal therapy," ACS Nano 5(6): 4319-4328, 2011.

Alder, M. N. et al. Antibody responses of variable lymphocyte receptors in the lamprey. Nat. Immunol. 9, 319-27 (2008).

Castaldo, C. et al. Cardiac fibroblast-derived extracellular matrix (biomatrix) as a model for the studies of cardiac primitive cell biological properties in normal and pathological adult human heart. Biomed Res. Int. (2013).

Chao, G. et al. Isolating and engineering human antibodies using yeast surface display. Nat. Protoc. 1, 755-768 (2006).

Collins, B. C. et al. Structural Insights into VLR Fine Specificity for Blood Group Carbohydrates. Structure 25, 1-12 (2017).

Daneman, R. The blood-brain barrier in health and disease. Ann. Neurol. 72, 648-72 (2012).

Harvey, A., Yen, T.-Y., Aizman, I., Tate, C. & Case, C. Proteomic analysis of the extracellular matrix produced by mesenchymal stromal cells: implications for cell therapy mechanism. PLoS One 8, e79283 (2013).

Kumar, P. et al. Macromolecularly crowded in vitro microenvironments accelerate the production of extracellular matrix-rich supramolecular assemblies. Sci. Rep. 5, 8729 (2015).

Lee, S.-C. et al. Design of a binding scaffold based on variable lymphocyte receptors of jawless vertebrates by module engineering. Proc. Natl. Acad. Sci. U. S. A. 109, 3299-304 (2012).

Luo, M. et al. Recognition of the Thomsen-Friedenreich pancarcinoma carbohydrate antigen by a lamprey variable lymphocyte receptor. J. Biol. Chem. 288, 23597-606 (2013).

Pasqualini, R. & Ruoslahti, E. Organ targeting in vivo using phage display peptide libraries. Nature 380, 364-6 (1996).

Ponsel, D., Neugebauer, J., Ladetzki-Baehs, K. & Tissot, K. High affinity, developability and functional size: the holy grail of combinatorial antibody library generation. Molecules 16, 3675-700 (2011).

Shusta, E, "Using Lamprey Antibodies to Profile the Blood-Brain Barrier", National Institute of Health (2015).

Stern, L. A. et al. Geometry and expression enhance enrichment of functional yeast displayed ligands via cell panning. Biotechnol. Bioeng. (2016). doi:10.1002/bit.26001.

Stutz, C. C., Zhang, X. & Shusta, E. V. Combinatorial approaches for the identification of brain drug delivery targets. Curr. Pharm. Des. 20, 1564-76 (2014).

Umlauf, BJ et al., "Identification of variable lymphocyte receptors that can target therapeutics to pathologically exposed brain extracellular matrix." Science Advances, May 15, 2019, vol. 5, No. eaau4245, pp. 1-12.

Wang, X. X. & Shusta, E. V. The use of scFv-displaying yeast in mammalian cell surface selections. J. Immunol. Methods 304, 30-42 (2005).

Yu, C. et al. Identification of human plasma cells with a lamprey monoclonal antibody. JCI Insight 1 (2016).

Zhou, H., Zhang, Y.-L., Lu, G., Ji, H. & Rodi, C. P. Recombinant antibody libraries and selection technologies. N. Biotechnol. 28, 448-52 (2011).

Gunn, R. J., Herrin, B. R., Acharya, S., Cooper, M. D. & Wilson, I. A. VLR Recognition of TLR5 Expands the Molecular Characterization of Protein Antigen Binding by Non-Ig based Antibodies. J. Mol. Biol. 430, 1350-1367 (2018).

FIG. 1A-1D
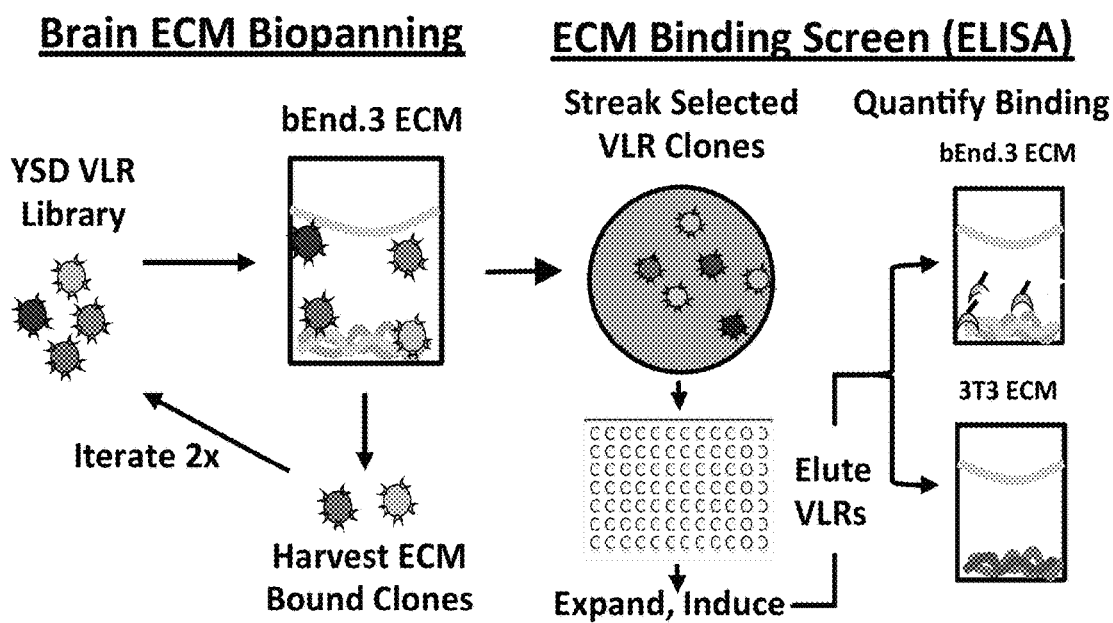
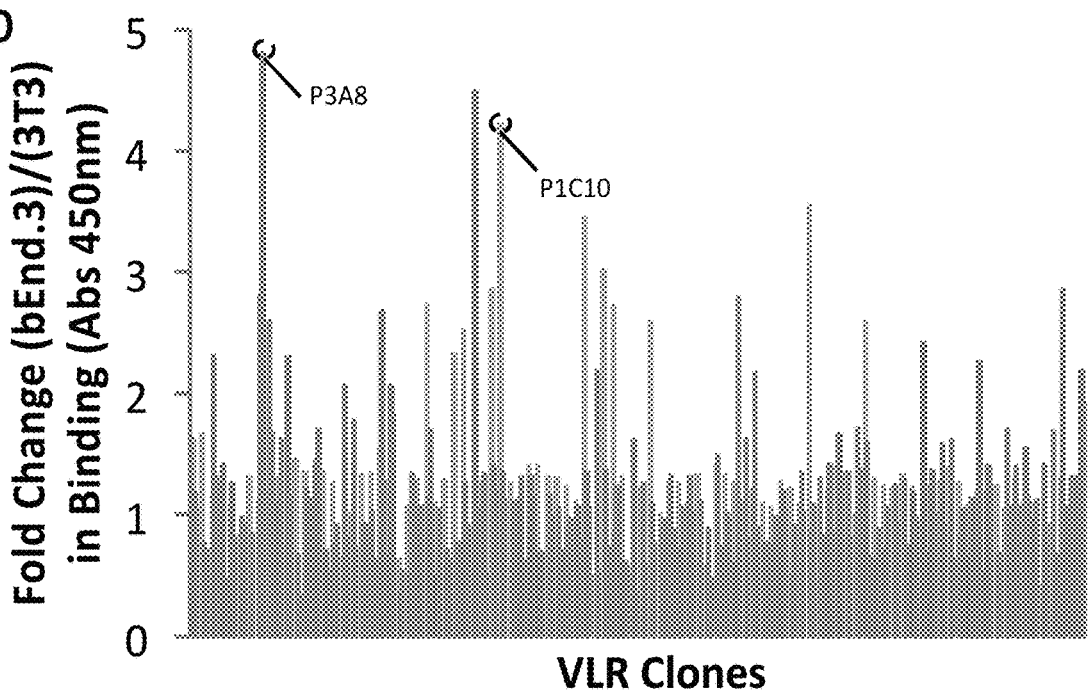

FIG. 1A-1D (continued)
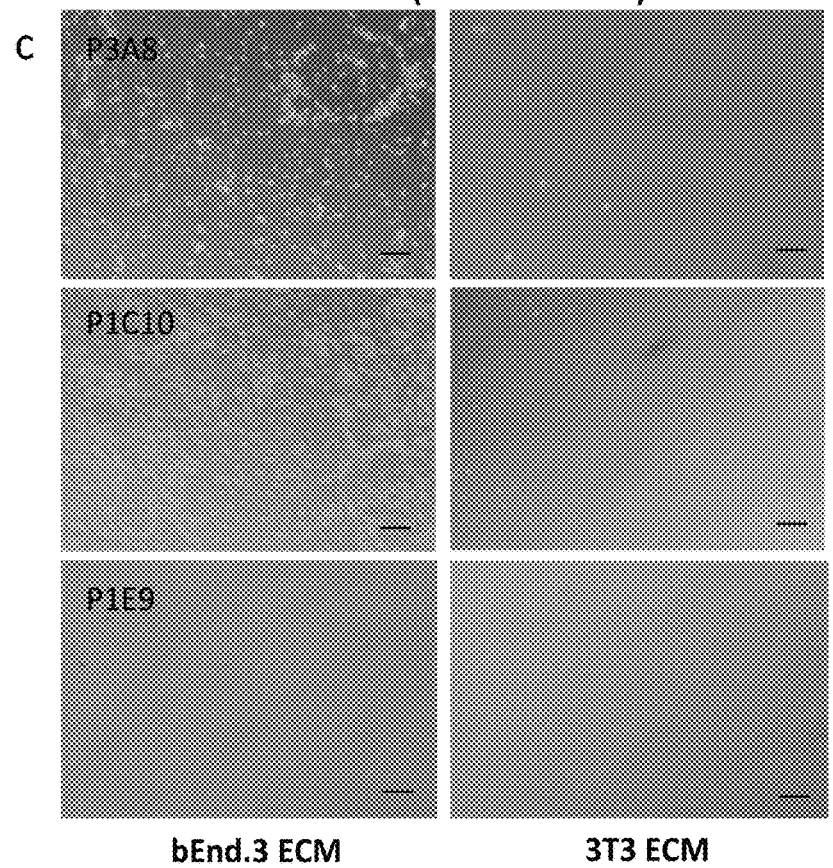
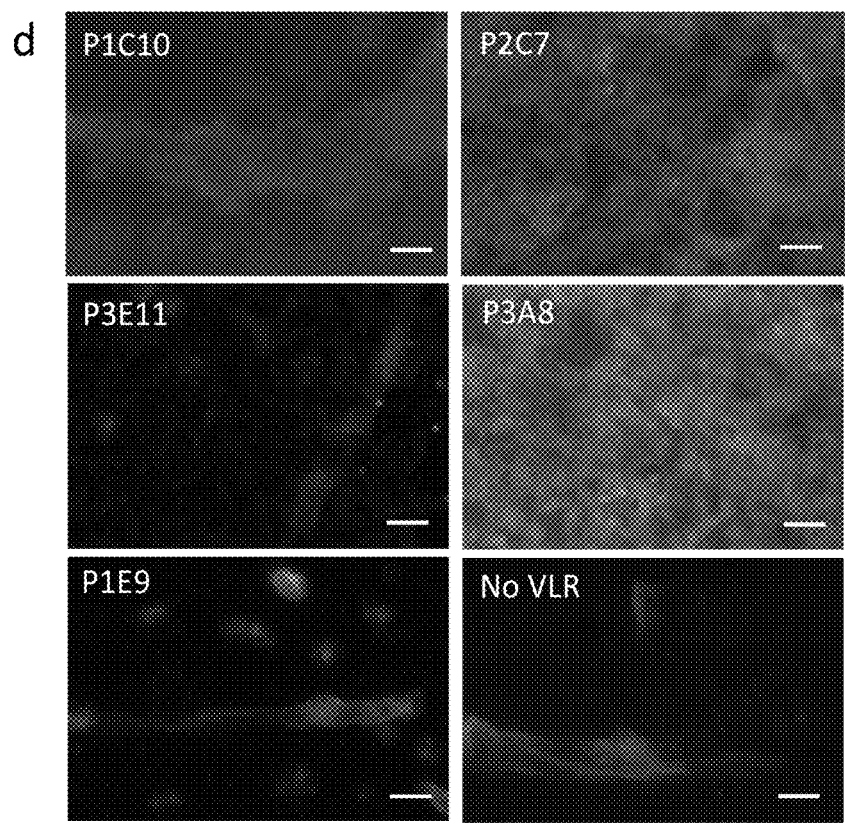

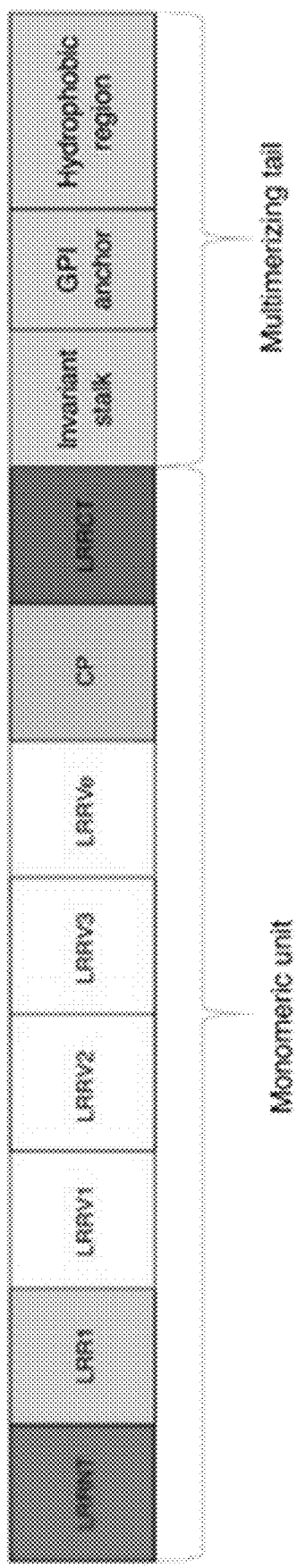

ACPSQCSCDQTTVKCHSRLITSVPAGIPTTTKLRLYSWQITKCLEPGVTDHLVMLEKLYISWNQLSALPVGVTDKLIKCIHLSLGY* SEQ ID NO:1
ACPSQCSCSGTQVNCHERRLASVPAGIPTTTRDLYIMDWQITKCLEPGVTDSLANLRELHLMGNQLVSLPGVTDKLIKCIHLYLGY* SEQ ID NO:2

NQLKSVPRGAFDNLKSLTHIWLLNPWDCECSDILYLKWTVQRASTVNLAGNEGDTVKCSGTNTPVRAVTEASTSPSKCP- SEQ ID NO:1
NQLKSVPRGAFDNLKSLTHIYLPNPWDCECSDILYLKWTVQRASTVNLAGNEGDTVKCSGTNTPVRAVTEASTSPSKCP- SEQ ID NO:2

*- sequence continued on next line

SEQUENCE LISTING

<160> NUMBER OF SEQ ID NOS: 36

<210> SEQ ID NO 1
<211> LENGTH: 168
<212> TYPE: PRT
<213> ORGANISM: Artificial Sequence
<220> FEATURE:
<223> OTHER INFORMATION: Synthetic- VLR clone P1C10

<400> SEQUENCE: 1

Ala Cys Pro Ser Gln Cys Ser Cys Asp Gln Thr Thr Val Lys Cys His
1               5                   10                  15

Ser Arg Arg Leu Thr Ser Val Pro Ala Gly Ile Pro Thr Thr Thr Lys
            20                  25                  30

Ile Leu Arg Leu Tyr Ser Asn Gln Ile Thr Lys Leu Glu Pro Gly Val
        35                  40                  45

Phe Asp His Leu Val Asn Leu Glu Lys Leu Tyr Ile Ser Trp Asn Gln

```
                    50                  55                  60
Leu Ser Ala Leu Pro Val Gly Val Phe Asp Lys Leu Thr Lys Leu Thr
 65                  70                  75                  80

His Leu Ser Leu Gly Tyr Asn Gln Leu Lys Ser Val Pro Arg Gly Ala
                     85                  90                  95

Phe Asp Asn Leu Lys Ser Leu Thr His Ile Trp Leu Leu Asn Asn Pro
                100                 105                 110

Trp Asp Cys Glu Cys Ser Asp Ile Leu Tyr Leu Lys Asn Trp Ile Val
            115                 120                 125

Gln His Ala Ser Ile Val Asn Leu Gln Gly His Gly Gly Val Asp Asn
        130                 135                 140

Val Lys Cys Ser Gly Thr Asn Thr Pro Val Arg Ala Val Thr Glu Ala
145                 150                 155                 160

Ser Thr Ser Pro Ser Lys Cys Pro
                165

<210> SEQ ID NO 2
<211> LENGTH: 168
<212> TYPE: PRT
<213> ORGANISM: Artificial Sequence
<220> FEATURE:
<223> OTHER INFORMATION: Synthetic- VLR clone P3A8

<400> SEQUENCE: 2

Ala Cys Pro Ser Gln Cys Ser Cys Ser Gly Thr Gln Val Asn Cys His
  1               5                  10                  15

Glu Arg Arg Leu Ala Ser Val Pro Ala Gly Ile Pro Thr Thr Thr Arg
                 20                  25                  30

Asp Leu Tyr Leu His Asp Asn Gln Ile Thr Lys Leu Glu Pro Gly Val
             35                  40                  45

Phe Asp Ser Leu Ala Asn Leu Arg Glu Leu His Leu Trp Gly Asn Gln
         50                  55                  60

Leu Val Ser Leu Pro Pro Gly Val Phe Asp Lys Leu Thr Lys Leu Thr
 65                  70                  75                  80

His Leu Tyr Leu Gly Tyr Asn Gln Leu Lys Ser Val Pro Arg Gly Ala
                     85                  90                  95

Phe Asp Asn Leu Lys Ser Leu Thr His Ile Tyr Leu Phe Asn Asn Pro
                100                 105                 110

Trp Asp Cys Glu Cys Ser Asp Ile Leu Tyr Leu Lys Asn Trp Ile Val
            115                 120                 125

Gln His Ala Ser Ile Val Asn Leu Gln Gly His Gly Gly Val Asp Asn
        130                 135                 140

Val Lys Cys Ser Gly Thr Asn Thr Pro Val Arg Ala Val Thr Glu Ala
145                 150                 155                 160

Ser Thr Ser Pro Ser Lys Cys Pro
                165

<210> SEQ ID NO 3
<211> LENGTH: 6
<212> TYPE: PRT
<213> ORGANISM: Artificial Sequence
<220> FEATURE:
<223> OTHER INFORMATION: Synthetic-VLR antigen binding region from clone
      P1C10
<220> FEATURE:
<221> NAME/KEY: misc_feature
<222> LOCATION: (2)..(2)
<223> OTHER INFORMATION: Xaa can be any naturally occurring amino acid
<220> FEATURE:
```

```
<221> NAME/KEY: misc_feature
<222> LOCATION: (4)..(4)
<223> OTHER INFORMATION: Xaa can be any naturally occurring amino acid

<400> SEQUENCE: 3

Thr Xaa Lys Xaa His Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic- VLR antigen binding region from
      clone P1C10
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 4

Ile Xaa Arg Xaa Tyr Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic- VLR antigen binding region from
      clone P1C10
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Lys Xaa Tyr Xaa Ser Trp
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic- VLR antigen binding region from
      clone P1C10
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 6

His Xaa Ser Xaa Gly Tyr
1               5

<210> SEQ ID NO 7
<211> LENGTH: 6
<212> TYPE: PRT
```

```
<213> ORGANISM: Artificial Sequence
<220> FEATURE:
<223> OTHER INFORMATION: Synthetic- VLR antigen binding region from
      clone P1C10
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 7

His Xaa Trp Xaa Leu Asn
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic- VLR tail region from clone P1C10

<400> SEQUENCE: 8

Ser Ile Val Asn Leu Gln Gly His Gly Gly Val Asp
1               5                   10

<210> SEQ ID NO 9
<211> LENGTH: 168
<212> TYPE: PRT
<213> ORGANISM: Artificial Sequence
<220> FEATURE:
<223> OTHER INFORMATION: Synthetic- generic VLR based on clone P1C10
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (39)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (63)..(80)
<223> OTHER INFORMATION: Xaa can be any naturally occurring amino acid
<220> FEATURE:
```

```
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (87)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (111)..(131)
<223> OTHER INFORMATION: Xaa can be any naturally occurring amino acid
<220> FEATURE:
<221> NAME/KEY: misc_feature
<222> LOCATION: (144)..(168)
<223> OTHER INFORMATION: Xaa can be any naturally occurring amino acid

<400> SEQUENCE: 9

Xaa Xaa Xaa Xaa Xaa Xaa Xaa Xaa Xaa Xaa Xaa Thr Xaa Lys Xaa His
 1               5                  10                  15

Ser Xaa Xaa Xaa Xaa Xaa Xaa Xaa Xaa Xaa Xaa Xaa Xaa Xaa Xaa Xaa
                20                  25                  30

Ile Xaa Arg Xaa Tyr Ser Xaa Xaa Xaa Xaa Xaa Xaa Xaa Xaa Xaa Xaa
            35                  40                  45

Xaa Xaa Xaa Xaa Xaa Xaa Xaa Xaa Lys Xaa Tyr Xaa Ser Trp Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

His Xaa Ser Xaa Gly Tyr Xaa Xaa Xaa Xaa Xaa Xaa Xaa Xaa Xaa Xaa
            85                  90                  95

Xaa Xaa Xaa Xaa Xaa Xaa Xaa Xaa His Xaa Trp Xaa Leu Asn Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Ser Ile Val Asn Leu Gln Gly His Gly Gly Val Asp Xaa
         130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa
                165

<210> SEQ ID NO 10
<211> LENGTH: 168
<212> TYPE: PRT
<213> ORGANISM: Artificial Sequence
<220> FEATURE:
<223> OTHER INFORMATION: Synthetic- generic VLR based on clone P1C10
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (18)..(32)
<223> OTHER INFORMATION: Xaa can be any naturally occurring amino acid
<220> FEATURE:
```

```
<221> NAME/KEY: misc_feature
<222> LOCATION: (39)..(56)
<223> OTHER INFORMATION: Xaa can be any naturally occurring amino acid
<220> FEATURE:
<221> NAME/KEY: misc_feature
<222> LOCATION: (63)..(80)
<223> OTHER INFORMATION: Xaa can be any naturally occurring amino acid
<220> FEATURE:
<221> NAME/KEY: misc_feature
<222> LOCATION: (87)..(104)
<223> OTHER INFORMATION: Xaa can be any naturally occurring amino acid
<220> FEATURE:
<221> NAME/KEY: misc_feature
<222> LOCATION: (111)..(131)
<223> OTHER INFORMATION: Xaa can be any naturally occurring amino acid
<220> FEATURE:
<221> NAME/KEY: misc_feature
<222> LOCATION: (144)..(168)
<223> OTHER INFORMATION: Xaa can be any naturally occurring amino acid

<400> SEQUENCE: 10

Xaa Xaa Xaa Xaa Xaa Xaa Xaa Xaa Xaa Xaa Xaa Thr Val Lys Cys His
 1               5                  10                  15

Ser Xaa Xaa Xaa Xaa Xaa Xaa Xaa Xaa Xaa Xaa Xaa Xaa Xaa Xaa Xaa
                20                  25                  30

Ile Leu Arg Leu Tyr Ser Xaa Xaa Xaa Xaa Xaa Xaa Xaa Xaa Xaa Xaa
            35                  40                  45

Xaa Xaa Xaa Xaa Xaa Xaa Xaa Xaa Lys Leu Tyr Ile Ser Trp Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

His Leu Ser Leu Gly Tyr Xaa Xaa Xaa Xaa Xaa Xaa Xaa Xaa Xaa Xaa
                85                  90                  95

Xaa Xaa Xaa Xaa Xaa Xaa Xaa Xaa His Ile Trp Leu Leu Asn Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Ser Ile Val Asn Leu Gln Gly His Gly Gly Val Asp Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa
                165

<210> SEQ ID NO 11
<211> LENGTH: 6
<212> TYPE: PRT
<213> ORGANISM: Artificial Sequence
<220> FEATURE:
<223> OTHER INFORMATION: Synthetic- VLR antigen binding region from
      clone P1C10

<400> SEQUENCE: 11

Thr Val Lys Cys His Ser
 1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic- VLR antigen binding region from
      clone P1C10

<400> SEQUENCE: 12
```

```
Ile Leu Arg Leu Tyr Ser
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic- VLR antigen binding region from
      clone P1C10

<400> SEQUENCE: 13

Lys Leu Tyr Ile Ser Trp
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic- VLR antigen binding region from
      clone P1C10

<400> SEQUENCE: 14

His Leu Ser Leu Gly Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic- VLR antigen binding region from
      clone P1C10

<400> SEQUENCE: 15

His Ile Trp Leu Leu Asn
1               5

<210> SEQ ID NO 16
<211> LENGTH: 132
<212> TYPE: PRT
<213> ORGANISM: Artificial Sequence
<220> FEATURE:
<223> OTHER INFORMATION: Synthetic- portion of VLR clone P1C10
      comprising antigen binding regions

<400> SEQUENCE: 16

Thr Val Lys Cys His Ser Arg Arg Leu Thr Ser Val Pro Ala Gly Ile
1               5                   10                  15

Pro Thr Thr Thr Lys Ile Leu Arg Leu Tyr Ser Asn Gln Ile Thr Lys
            20                  25                  30

Leu Glu Pro Gly Val Phe Asp His Leu Val Asn Leu Glu Lys Leu Tyr
        35                  40                  45

Ile Ser Trp Asn Gln Leu Ser Ala Leu Pro Val Gly Val Phe Asp Lys
    50                  55                  60

Leu Thr Lys Leu Thr His Leu Ser Leu Gly Tyr Asn Gln Leu Lys Ser
65                  70                  75                  80

Val Pro Arg Gly Ala Phe Asp Asn Leu Lys Ser Leu Thr His Ile Trp
                85                  90                  95

Leu Leu Asn Asn Pro Trp Asp Cys Glu Cys Ser Asp Ile Leu Tyr Leu
            100                 105                 110

Lys Asn Trp Ile Val Gln His Ala Ser Ile Val Asn Leu Gln Gly His
```

Gly Gly Val Asp
    130

<210> SEQ ID NO 17
<211> LENGTH: 6
<212> TYPE: PRT
<213> ORGANISM: Art

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 20

His Xaa Tyr Xaa Gly Tyr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic- VLR antigen binding region from
      clone P3A8
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 21

His Xaa Tyr Xaa Phe Asn
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic- VLR antigen binding region from
      clone P3A8

<400> SEQUENCE: 22

Gln Val Asn Cys His Glu
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic- VLR antigen binding region from
      clone P3A8

<400> SEQUENCE: 23

Asp Leu Tyr Leu His Asp
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic- VLR antigen binding region from
      clone P3A8

<400> SEQUENCE: 24

Glu Leu His Leu Trp Gly
1               5
```

```
<210> SEQ ID NO 25
<211> LENGTH: 6
<212> TYPE: PRT
<213> ORGANISM: Artificial Sequence
<220> FEATURE:
<223> OTHER INFORMATION: Synthetic- VLR antigen binding region from
      clone P3A8

<400> SEQUENCE: 25

His Leu Tyr Leu Gly Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic- VLR antigen binding region from
      clone P3A8

<400> SEQUENCE: 26

His Ile Tyr Leu Phe Asn
1               5

<210> SEQ ID NO 27
<211> LENGTH: 168
<212> TYPE: PRT
<213> ORGANISM: Artificial Sequence
<220> FEATURE:
<223> OTHER INFORMATION: Synthetic- generic VLR based on clone P3A8
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (39)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (63)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
```

-continued

<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (87)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (111)..(131)
<223> OTHER INFORMATION: Xaa can be any naturally occurring amino acid
<220> FEATURE:
<221> NAME/KEY: misc_feature
<222> LOCATION: (145)..(168)
<223> OTHER INFORMATION: Xaa can be any naturally occurring amino acid

<400> SEQUENCE: 27

Xaa Xaa Xaa Xaa Xaa Xaa Xaa Xaa Xaa Xaa Xaa Gln Xaa Asn Xaa His
1               5                   10                  15

Glu Xaa Xaa Xaa Xaa Xaa Xaa Xaa Xaa Xaa Xaa Xaa Xaa Xaa Xaa Xaa
            20                  25                  30

Asp Xaa Tyr Xaa His Asp Xaa Xaa Xaa Xaa Xaa Xaa Xaa Xaa Xaa Xaa
        35                  40                  45

Xaa Xaa Xaa Xaa Xaa Xaa Xaa Xaa Glu Xaa His Xaa Trp Gly Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

His Xaa Tyr Xaa Gly Tyr Xaa Xaa Xaa Xaa Xaa Xaa Xaa Xaa Xaa Xaa
            85                  90                  95

Xaa Xaa Xaa Xaa Xaa Xaa Xaa Xaa His Xaa Tyr Xaa Phe Asn Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Ser Ile Val Asn Leu Gln Gly His Gly Gly Val Asp Asn
130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa
                165

<210> SEQ ID NO 28
<211> LENGTH: 168
<212> TYPE: PRT
<213> ORGANISM: Artificial Sequence
<220> FEATURE:
<223> OTHER INFORMATION: Synthetic- generic VLR based on clone P3A8
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (18)..(32)
<223> OTHER INFORMATION: Xaa can be any naturally occurring amino acid
<220> FEATURE:
<221> NAME/KEY: misc_feature
<222> LOCATION: (39)..(56)
<223> OTHER INFORMATION: Xaa can be any naturally occurring amino acid
<220> FEATURE:

```
<221> NAME/KEY: misc_feature
<222> LOCATION: (63)..(80)
<223> OTHER INFORMATION: Xaa can be any naturally occurring amino acid
<220> FEATURE:
<221> NAME/KEY: misc_feature
<222> LOCATION: (87)..(104)
<223> OTHER INFORMATION: Xaa can be any naturally occurring amino acid
<220> FEATURE:
<221> NAME/KEY: misc_feature
<222> LOCATION: (111)..(131)
<223> OTHER INFORMATION: Xaa can be any naturally occurring amino acid
<220> FEATURE:
<221> NAME/KEY: misc_feature
<222> LOCATION: (145)..(168)
<223> OTHER INFORMATION: Xaa can be any naturally occurring amino acid

<400> SEQUENCE: 28

Xaa Xaa Xaa Xaa Xaa Xaa Xaa Xaa Xaa Xaa Xaa Gln Val Asn Cys His
1               5                   10                  15

Glu Xaa Xaa Xaa Xaa Xaa Xaa Xaa Xaa Xaa Xaa Xaa Xaa Xaa
            20                  25                  30

Asp Leu Tyr Leu His Asp Xaa Xaa Xaa Xaa Xaa Xaa Xaa Xaa Xaa
        35                  40                  45

Xaa Xaa Xaa Xaa Xaa Xaa Xaa Xaa Glu Leu His Leu Trp Gly Xaa Xaa
50                  55                  60

Xaa Xaa Xaa Xaa Xaa Xaa Xaa Xaa Xaa Xaa Xaa Xaa Xaa Xaa Xaa
65                  70                  75                  80

His Leu Tyr Leu Gly Tyr Xaa Xaa Xaa Xaa Xaa Xaa Xaa Xaa Xaa
        85                  90                  95

Xaa Xaa Xaa Xaa Xaa Xaa Xaa Xaa His Ile Tyr Leu Phe Asn Xaa Xaa
        100                 105                 110

Xaa Xaa Xaa Xaa Xaa Xaa Xaa Xaa Xaa Xaa Xaa Xaa Xaa Xaa
        115                 120                 125

Xaa Xaa Xaa Ser Ile Val Asn Leu Gln Gly His Gly Gly Val Asp Asn
        130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa
                165

<210> SEQ ID NO 29
<211> LENGTH: 6
<212> TYPE: PRT
<213> ORGANISM: Artificial Sequence
<220> FEATURE:
<223> OTHER INFORMATION: Synthetic- His tag

<400> SEQUENCE: 29

His His His His His His
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic- cMyc tag

<400> SEQUENCE: 30

Glu Gln Lys Leu Ile Ser Glu Glu Asp Leu
1               5                   10

<210> SEQ ID NO 31
```

```
<211> LENGTH: 8
<212> TYPE: PRT
<213> ORGANISM: Artificial Sequence
<220> FEATURE:
<223> OTHER INFORMATION: Synthetic- FLAG tag

<400> SEQUENCE: 31

Asp Tyr Lys Asp Asp Asp Asp Lys
1               5

<210> SEQ ID NO 32
<211> LENGTH: 14
<212> TYPE: PRT
<213> ORGANISM: Artificial Sequence
<220> FEATURE:
<223> OTHER INFORMATION: Synthetic- V5-tag

<400> SEQUENCE: 32

Gly Lys Pro Ile Pro Asn Pro Leu Leu Gly Leu Asp Ser Thr
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Synthetic- HA-tag

<400> SEQUENCE: 33

Tyr Pro Tyr Asp Val Pro Asp Tyr Ala
1               5

<210> SEQ ID NO 34
<211> LENGTH: 18
<212> TYPE: PRT
<213> ORGANISM: Artificial Sequence
<220> FEATURE:
<223> OTHER INFORMATION: Synthetic- NE-tag

<400> SEQUENCE: 34

Thr Lys Glu Asn Pro Arg Ser Asn Gln Glu Glu Ser Tyr Asp Asp Asn
1               5                   10                  15

Glu Ser

<210> SEQ ID NO 35
<211> LENGTH: 15
<212> TYPE: PRT
<213> ORGANISM: Artificial Sequence
<220> FEATURE:
<223> OTHER INFORMATION: Synthetic- S-tag

<400> SEQUENCE: 35

Lys Glu Thr Ala Ala Ala Lys Phe Glu Arg Gln His Met Asp Ser
1               5                   10                  15

<210> SEQ ID NO 36
<211> LENGTH: 10
<212> TYPE: PRT
<213> ORGANISM: Artificial Sequence
<220> FEATURE:
<223> OTHER INFORMATION: Synthetic- Ty tag

<400> SEQUENCE: 36

Glu Val His Thr Asn Gln Asp Pro Leu Asp
1               5                   10
```

VARIABLE LYMPHOCYTE RECEPTORS THAT TARGET THE BRAIN EXTRACELLULAR MATRIX AND METHODS OF USE

CROSS-REFERENCE TO RELATED APPLICATIONS

This application claims priority to U.S. Provisional Application No. 62/783,475, filed on Dec. 21, 2018, the contents of which are incorporated by reference in its entirety.

STATEMENT REGARDING FEDERALLY SPONSORED RESEARCH

This invention was made with government support under NS091851 and NS099158 awarded by the National Institutes of Health. The government has certain rights in the invention.

SEQUENCE LISTING

A Sequence Listing accompanies this application and is submitted as an ASCII text file of the sequence listing named "2019-12-11_960296.03973_ST25.txt" which is 21.9 KB in size and was created on Dec. 11, 2019. The sequence listing is electronically submitted via EFS-Web with the application and is incorporated herein by reference in its entirety.

BACKGROUND OF THE INVENTION

The field of the invention is related to polypeptides and antibodies specific to the extracellular matrix of the brain.

Under healthy conditions, brain endothelial cells form the blood-brain barrier (BBB) that differentially segregates blood components from the central nervous system (CNS).[1] Because of the BBB's specialized barrier properties, including tight junctions and drug efflux transport, CNS uptake of systemically administered therapeutics is often limited.[1-3] However, multiple events including acute insults such as trauma and stroke; chronic pathologies such as tumors and multiple sclerosis; and artificial methods such as high frequency ultrasound and osmotic agents can disrupt BBB integrity.[2,4-11] Although the time course, extent and location of BBB disruption dramatically differs with each condition, the consistent result is pathological exposure of normally sequestered brain extracellular matrix (ECM).[1,8,12-16]

Thus there is a need for agents and methods that are able to target brain regions with pathologically disrupted BBB, which can be used for non-cell intrinsic methods of therapeutic delivery to previously "difficult-to-access" CNS disease sites.

SUMMARY OF THE INVENTION

The present invention overcomes the aforementioned drawbacks by providing polypeptides, nucleic acids encoding the polypeptides, and compositions comprising the polypeptides, wherein the polypeptides comprises variable lymphocyte receptors specific for brain extracellular matrix in vivo which are exposed due to blood brain barrier (BBB) disruption, and polypeptides and compositions comprising them.

In one aspect, the present disclosure provides an isolated polypeptide or antigen-binding fragment thereof able to specifically bind to the brain extracellular matrix in vivo comprising an amino acid sequence of a variable lymphocyte receptor (VLR) comprising two or more of the following regions:
  (i) TXKXHS (SEQ ID NO:3),
  (ii) IXRXYS (SEQ ID NO:4),
  (iii) KXYXSW (SEQ ID NO:5),
  (iv) HXSXGY (SEQ ID NO:6),
  (v) HXWXLN (SEQ ID NO:7), and
  (vi) SIVNLQGHGGVD (SEQ ID NO:8), wherein each X is selected from any amino acid, and
  wherein the isolated peptide or antigen-binding fragment thereof is able to specifically bind to the brain extracellular matrix in vivo.

In another aspect, the disclosure provides an isolated polypeptide or antigen-binding fragment thereof comprising an amino acid sequence of $(X)_{11}$TXKXHS $(X)_{15}$IXRXY S $(X)_{18}$(XYXSW$(X)_{18}$HXSXGY$(X)_{18}$HXWXLN$(X)_{21}$ SIVNLQG HGGVD$(X)_{25}$, wherein each X is independently selected from any amino acid.

In yet another aspect, the disclosure provides an isolated polypeptide or antigen binding fragment thereof able to specifically bind to the brain extracellular matrix in vivo comprising an amino acid sequence of a variable lymphocyte receptor (VLR) comprising two or more of the following regions:
  (i) SEQ ID NO:11 (TVKCHS),
  (ii) SEQ ID NO:12 (ILRLYS),
  (iii) SEQ ID NO:13 (KLYISW),
  (iv) SEQ ID NO:14 (HLSLGY),
  (v) SEQ ID NO:15 (HIWLLN), and
  (vi) SEQ ID NO:8 (SIVNLQGHGGVD).

In one aspect, the disclosure provides an isolated polypeptides or antigen binding fragment thereof wherein the VLR comprises the amino acid sequence of $(X)_{11}$TVKCHS $(X)_{15}$ILRLYS$(X)_{18}$KLYISW$(X)_{18}$HLSLGY$(X)_{18}$HIWLLN $(X)_{21}$SIVNLQGHG GVD$(X)_{25}$ (SEQ ID NO:10).

In another aspect, the disclosure provides an isolated polypeptides or antigen binding fragments thereof wherein the VLR is selected from the group consisting of P1C10 (SEQ ID NO:1) and an amino acid sequence with at least 75% sequence similarity to SEQ ID NO:1.

In another aspect, the disclosure provides a brain ECM targeting composition comprising the isolated peptide or antigen-binding fragment described herein and a pharmaceutically acceptable carrier.

In yet another aspect, the disclosure provides an isolated nucleic acid sequence encoding the isolated polypeptide or antigen-binding fragment described herein.

In yet another aspect, the disclosure provides a vector encoding and able to express the isolated polypeptide or antigen-binding fragment described herein or comprising the isolated nucleic acid sequence described herein.

Another aspect of the disclosure provides a method of targeting an agent to the brain extracellular matrix, the method comprising:
  (a) administering to the subject an isolated polypeptide or antigen-binding fragment described herein which is directly or indirectly linked to the agent or
  (b) administering to the subject a brain extracellular matrix targeting composition described herein.

In another aspect, the disclosure provides a method of treating a disease or injury associated with BBB disruption in a subject in need thereof, the method comprising
  (a) administering to the subject an isolated polypeptide or antigen-binding fragment described herein which is directly or indirectly linked to the agent or (b) administering to the subject a brain extracellular matrix targeting composition described herein,
in an amount effective to treat the disease or injury in the subject.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

FIGS. 1A-1D. Identification of VLRs that bind brain ECM. (A) A yeast surface display VLR library underwent two rounds of biopanning to enrich for clones that bind bEnd.3 ECM. Next, individual clones were grown, induced and screened for comparative binding to bEnd.3 and 3T3 ECM. VLRs were released from the yeast surface using reducing agent and VLR binding to ECM was measured by probing the anti-c-myc epitope tag in an ELISA format. (B) Fold-changes in ECM binding. The ratio of bEnd.3 ECM/3T3 ECM ELISA signals is shown for 285 VLR clones. Lead clones P3A8 and P1C10 are noted. (C) Preferential binding to bEnd.3 ECM was evaluated for selected clones by biopanning individual clones onto bEnd.3 and 3T3 ECM. Yeast binding was qualitatively analyzed by bright field microscopy. Scale bars=100 µm. (D) VLRs were reduced off the yeast surface and used in labeling murine brain sections and detected via an anti-c-myc epitope tag antibody (green). Microvessels (magenta) were labeled with IS-GB4 lectin, and cell nuclei (blue) were visualized with Hoechst 33342 stain. Scale bars=20 µm.

FIG. 12A depicts the amino acid regions of a VLR. FIG. 12A is adapted from: Waters and Shusta. "The variable lymphocyte receptor as an antibody alternative." Curr Opin Biotechnol. 2018 August; 52:74-79.

FIG. 12B depicts the alignment of the exemplary VLRs isolated.

DETAILED DESCRIPTION OF THE INVENTION

Figures 2A, 2B, 2C, 2D, 2E:
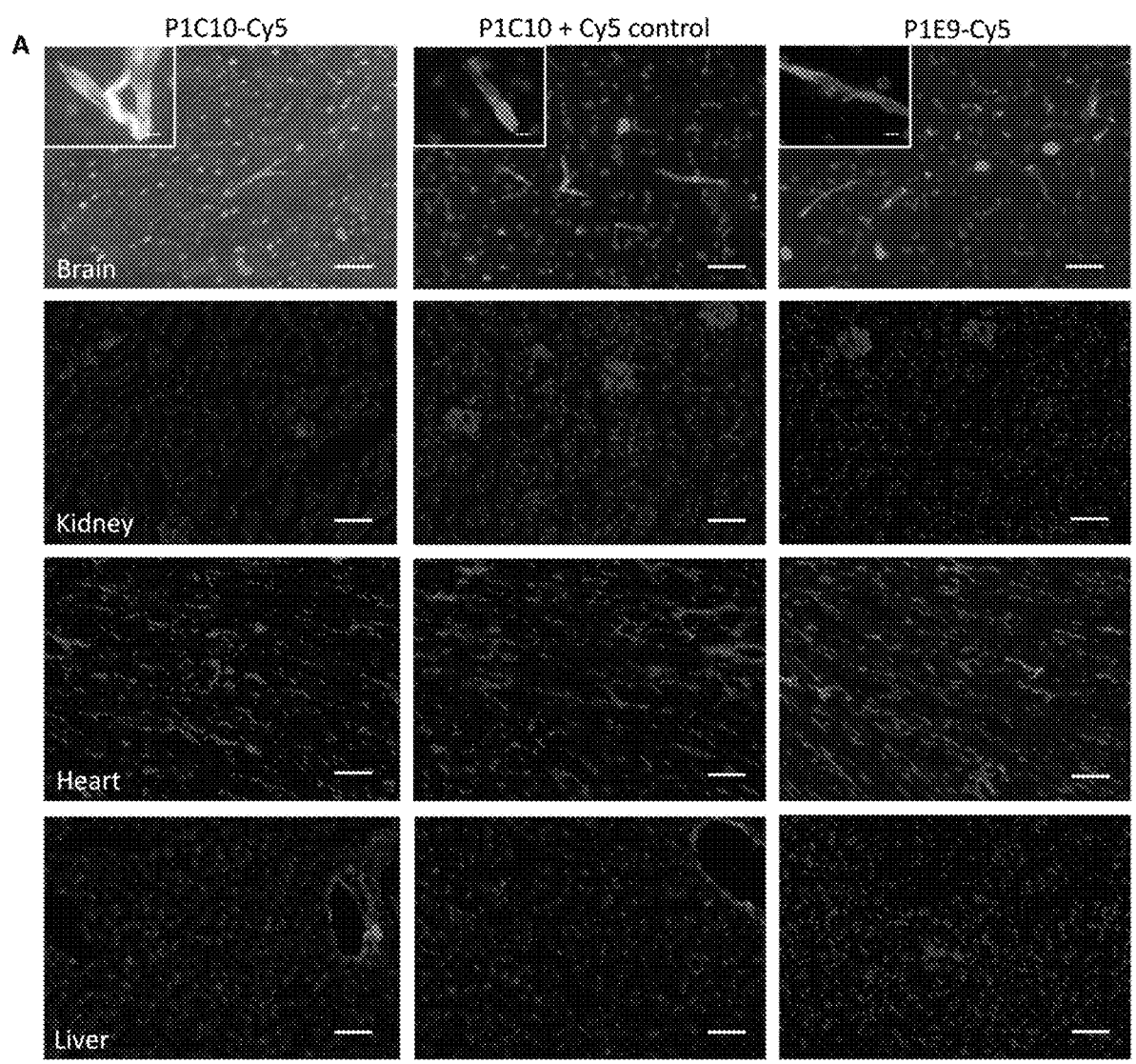
FIGS. 2A-2E. Binding characterization of P1C10. (A) P1C10-Cy5 (green) was used to probe murine tissues. GS-IB4 lectin labels microvessels (magenta), and cell nuclei are stained with Hoechst 33342 (blue). The P1C10+Cy5 control column of images are labeled as in the left column except the P1C10 VLR and Cy5 that are not chemically conjugated. Images in the right column are labeled with nonbinding VLR, P1E9-Cy5. Scale bars, 100 µm. Inset images are higher magnification of brain labeling. Scale bars, 20 µm. (B) Quantification of VLR signal from images derived from groups presented in (A) [*P<0.01, analysis of variance (ANOVA)]. (C) P1C10 VLR demonstrates a monomeric affinity of 48.38±6.05 nM for bEnd.3 ECM. Three replicates (means±SD) fit to a monomeric equilibrium binding model are plotted. (D) Freshly resected, snap-frozen, histologically normal human brain section labeled with either P1C10-Cy5 (green) or negative control P1E9-Cy5. Anti-Cd31 monoclonal antibody (mAb) labels microvessels (magenta), and cell nuclei are stained with Hoechst 33342 (blue). (E) A patient-derived GBM specimen was freshly resected, snap-frozen, and sectioned for labeling with P1C10-Cy5 (green) and compared to negative control, P1E9-Cy5. Anti-Cd31 mAb labels microvessels (magenta), and cell nuclei are stained with Hoechst 33342 (blue). Scale bars, 20 µm.
Figures 2A, 2B, 2C, 2D, 2E:
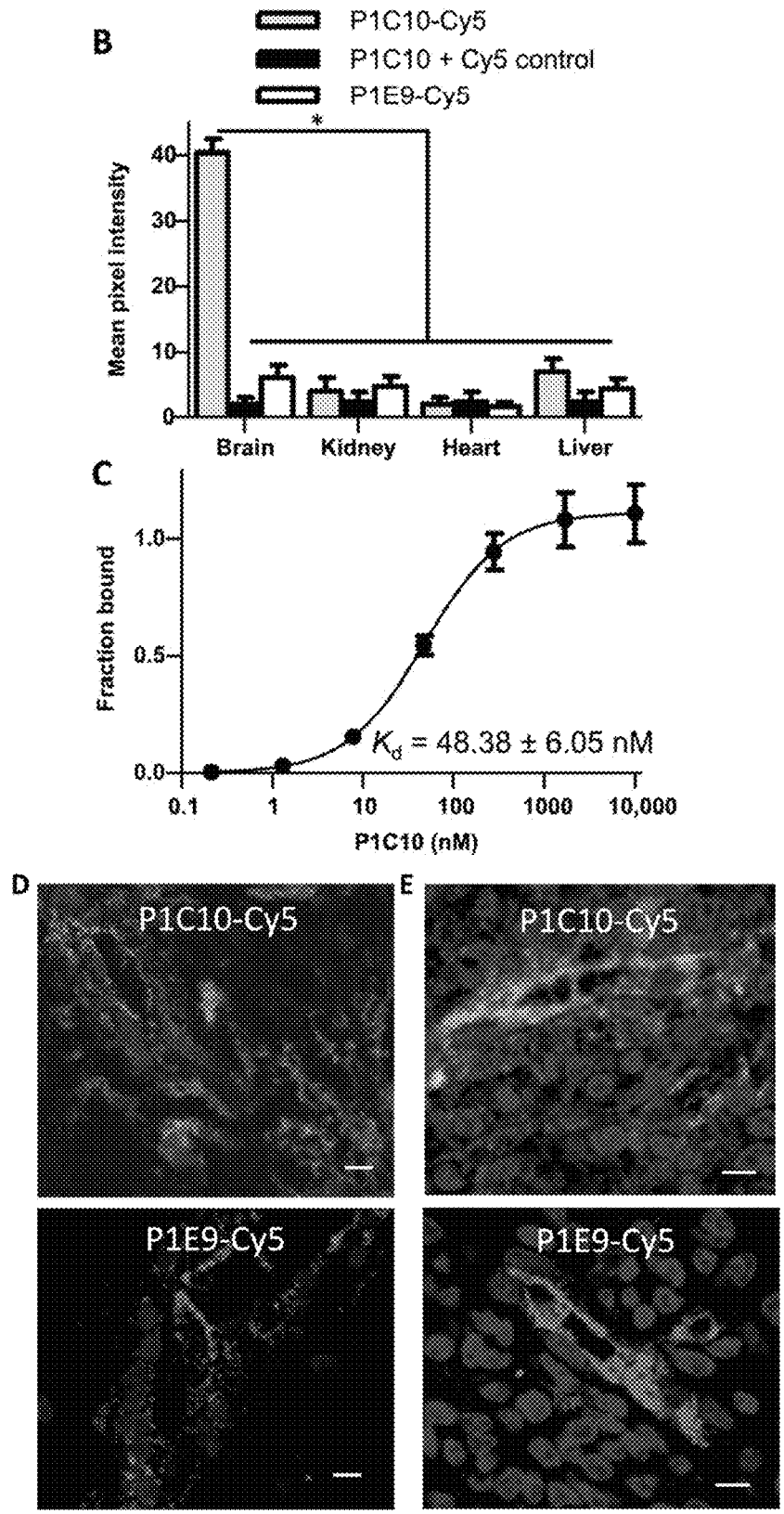
Figures 3A, 3B, 3C, 3D:
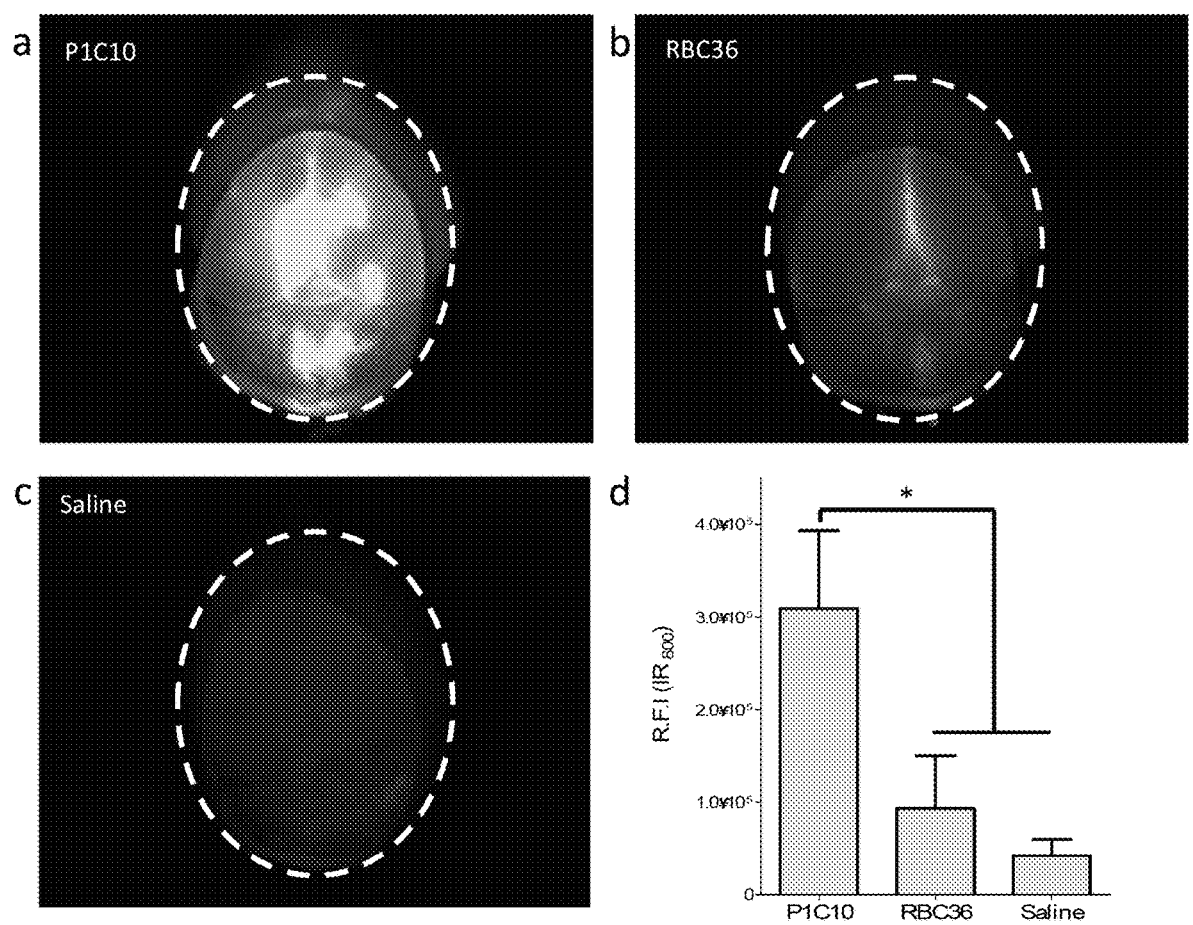
FIGS. 3A-3D. Brain retention of VLRs after BBB disruption with mannitol. C57BL/6 mice were intravenously administered VLR-IR$_{800}$ followed by hyperosmolar mannitol to transiently disrupt the BBB. While the BBB was still disrupted, mice were perfused to remove unbound VLR. Representative, whole brain images, of retained IR$_{800}$ signal from mice administered (A) P1C10-IR$_{800}$, (B) RBC36-IR$_{800}$, and (C) saline treated animals are presented and quantified in panel (D) Dotted line outlines total brain area that was quantified in each image. (mean±SD, n=3 mice per group. *p<0.01, ANOVA).

The present invention has been described in terms of one or more preferred embodiments, and it should be appreciated that many equivalents, alternatives, variations, and modifications, aside from those expressly stated, are possible and within the scope of the invention. Before the present invention is described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

Currently most approaches to brain drug delivery attempt to overcome the blood-brain barrier. However, many brain diseases and medical interventions can cause blood-brain barrier disruption, which in turn, exposes normally inaccessible underlying brain extracellular matrix (ECM). The antibodies of the present disclosure target brain ECM as it becomes exposed due to injury or disease. Thus, these antibodies can be used to target the brain in cases that result from the BBB disruption. The Examples below demonstrate therapeutic advantage to ECM targeting and the ability to accumulate drugs within the brain via disrupted BBB which expose normally inaccessible ECM.

The present disclosure provides polypeptides and antigen binding fragments thereof that specifically/selectively bind to the usually inaccessible brain extracellular matrix in vivo and compositions, method and kits for uses thereof. Further, the present disclosure provides methods of treating disease or injury associated with blood-brain barrier disruption by using the polypeptides or antigen binding fragments thereof described herein.

Under healthy conditions, brain endothelial cells form the blood-brain barrier (BBB) differentially segregates blood components from the central nervous system (CNS). However, multiple events including acute insults such as trauma and stroke; chronic pathologies such as tumors and multiple sclerosis; and artificial methods such as high frequency ultrasound and osmotic agents can disrupt BBB integrity.[2,4-11] Although the time course, extent and location of BBB disruption dramatically differs with each condition, all these conditions have in common the consistent result of pathological exposure of normally sequestered brain extracellular matrix (ECM).[1,8,12-16] The present peptides target brain regions with pathologically disrupted BBB, and serve as a non-cell intrinsic method of therapeutic delivery to previously 'difficult-to-access' CNS disease sites. This strategy is potentially superior to therapies directed against cell intrinsic targets because normal brain ECM serves as the targeting ligand rather than cell-associated disease variants or markers that are often altered or lost after treatments, resulting in therapeutic resistance.[17] Moreover, a single ECM targeting ligand as described herein can be applied to many different CNS diseases or conditions and provides a versatile therapeutic platform, contrasting with other recent ECM targeted approaches that selectively target injury or diseased ECM. The Examples demonstrate the ECM-targeted therapeutic delivery using the polypeptides described herein to treat incurable brain cancer, glioblastoma (GBM). Better GBM therapies are sorely needed because patients have a uniformly poor prognosis with median survival of less than two years despite aggressive clinical treatments of surgery, chemotherapy and radiation.[19-21] Targeting of GBM and specifically, ECM components, offers new treatment strategies. In addition, central or internal GBM regions exhibit disrupted BBB revealed by MRI enhancement with gadolinium contrast, suggesting compatibility with ECM-targeted approaches.[8,11,13,23] Thus, our Examples set out to demonstrate the pathologically exposed brain ECM in GBM could be targeted for therapeutic advantage.

The present disclosure used lamprey antigen receptors known as variable lymphocyte receptors (VLRs).[24,25] VLRs are crescent-shaped, leucine-rich repeat proteins that recognize antigenic targets with specificity and affinity comparable to Ig-based antibodies.[26-28] Combining the unique binding site geometry with the approximately 500 million years evolutionary distance between lamprey and mammals, VLRs could possibly recognize conserved proteins and glycans in ECM that may not be effectively targeted by mammalian antibodies.[24-26,28]

To identify VLRs that bind brain ECM, an immunized lamprey VLR library in yeast surface display format was screened by biopanning. The library was generated from the VLR repertoire of lamprey immunized with mechanically isolated murine brain microvessel plasma membrane preparations that contained associated brain ECM.[29] The library was first enriched for ECM binders via two rounds of biopanning on decellularized ECM generated by cultured mouse brain endothelial cells (bEnd.3 cell line). ECM-binding clones were identified that preferentially bound bEnd.3 ECM compared to control mouse fibroblast ECM (3T3 cell line). The resultant enriched pool of ECM-binding clones was subsequently assayed for preferential binding to brain ECM using a moderate throughput, ELISA-based screen (FIG. 1A). In total, 285 clones were assayed for differential binding, and observed binding signals were as high as ~5-fold preference for bEnd.3 ECM (FIG. 1B). Importantly, 10 clones demonstrated at least a 2.5-fold preference for bEnd.3 ECM. Yeast displaying clones P1C10 and P2C7 (ELISA fold change=4.2 and 4.5, respectively) bound selectively to bEnd.3 ECM compared to 3T3 ECM, whereas a nonbinding VLR clone P1E9 showed very little ECM binding (FIG. 1C, P1E9). Given their positive binding and substantial bEnd.3 ECM selectivity in the ELISA assay, P1C10 and P3A8 were subjected to more detailed evaluation.

Figure 7:
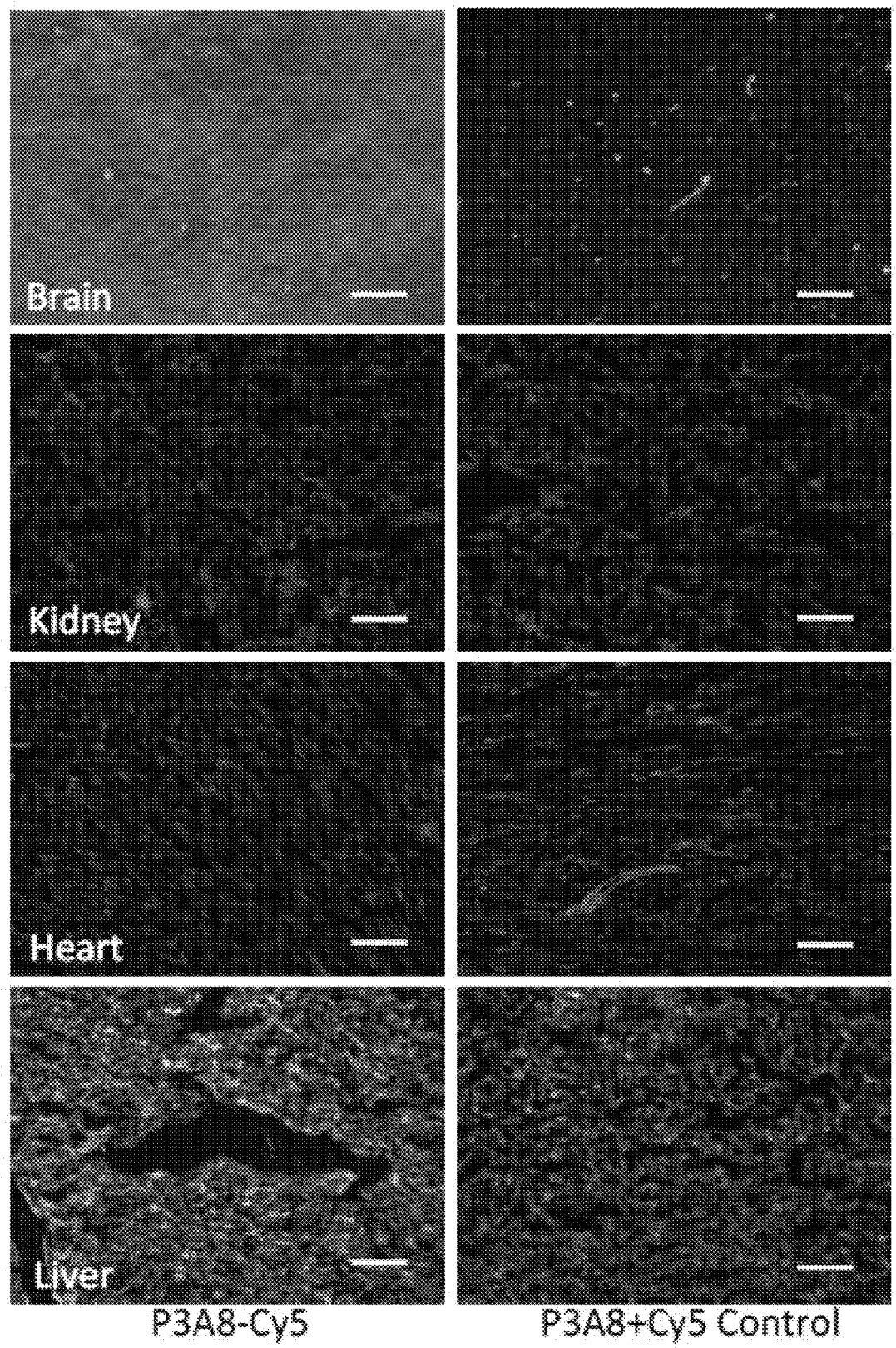
FIG. 7. P3A8 binding to murine tissue sections. Images on the left side are stained with Hoechst 33342 for DNA (blue) and labeled with GS-IB4-AF488 for microvessels (magenta) and P3A8-Cy5 (green). Images on the right are labeled as the left except the P3A8 VLR and Cy5 are not chemically conjugated to serve as a negative control. Origin of the tissue sections are labeled for each pair of images. Scale bars=100 µm.
Figure 8:
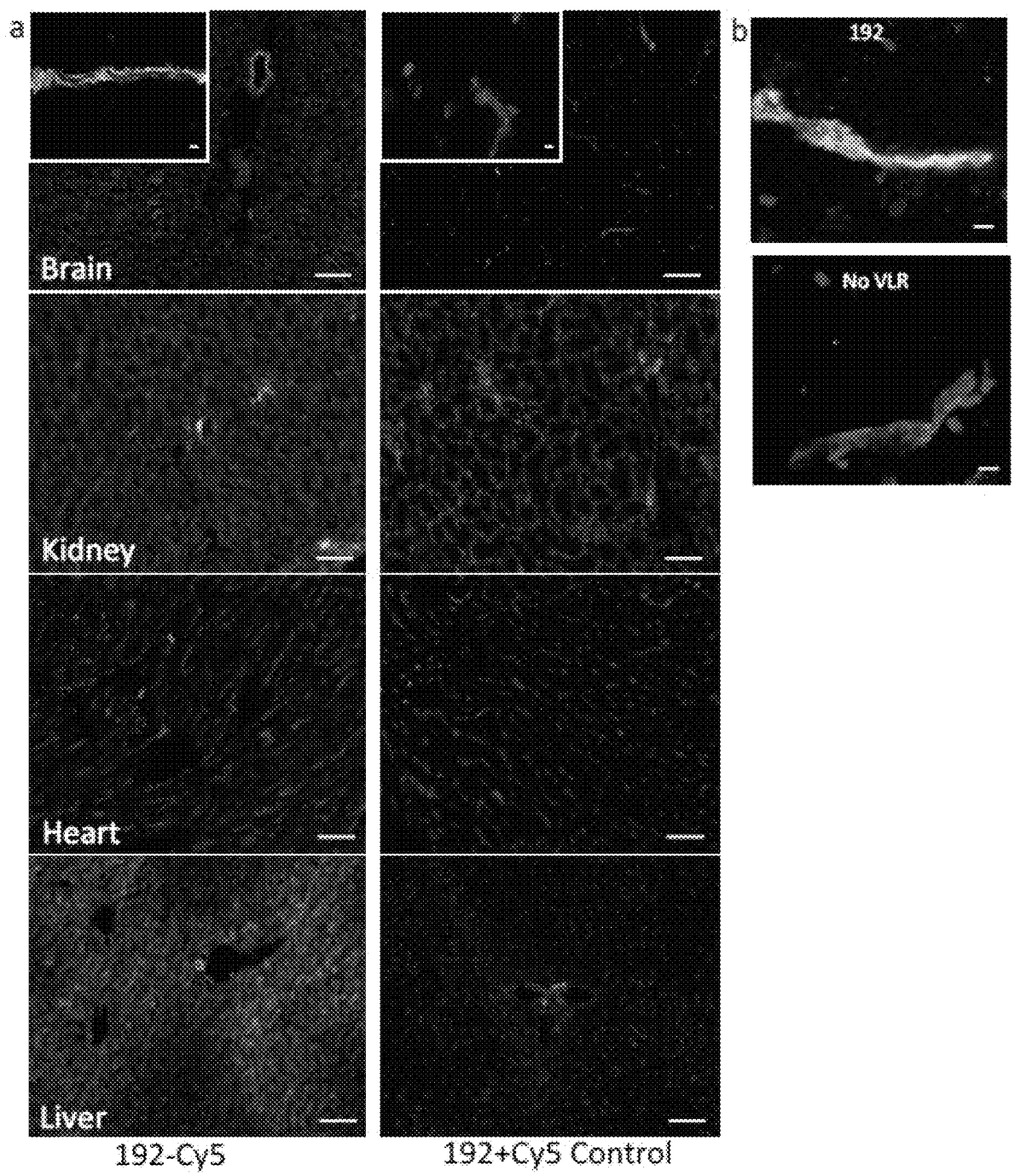
FIGS. 8A-8B. VLR 192 binding to tissue sections. (A) Images in the left column are stained with Hoechst 33342 for DNA (blue) and labeled with GS-IB4-AF488 for microvessels (magenta) and 192-Cy5 (green). Images on the right are stained as the left except the 192 VLR and Cy5 are not chemically conjugated to serve as a negative control. Scale bars=100 µm. Inset images are higher magnification images of the same groups. Scale bars=20 µm Origin of the tissue sections are labeled for each pair of images. (B) Human brain sections labeled with 192-Cy5 as in a) microvessels are immunolabeled with an anti-Cd31 antibody (magenta). Scale bars=20 µm.

Next, in vivo relevance of ECM-binding VLR candidates was confirmed by cloning the P1C10 and P3A8 into our previously described intein fusion yeast display system that allows site-specific modification of the VLR at the carboxy-terminus.[30,31] In this way, P1C10 and P3A8 were functionalized with Cy5 fluorescent dye.[32] Direct immunolabeling of murine tissues using VLR-Cy5 conjugates indicated that P1C10-Cy5 possessed substantial brain ECM selectivity compared kidney, heart and liver tissues (FIG. 2A). In contrast, P3A8-Cy5 bound both brain and liver ECM with similar intensity, but like P1C10-Cy5, also did not show binding to kidney and heart tissues (FIG. 7). P1C10-Cy5 bound human brain ECM compared with controls, with a pattern similar to that observed in murine brain sections (FIG. 2B). Furthermore, P1C10-Cy5 also bound to ECM in cryosections of freshly resected human GBM specimens (FIG. 2C). Given the desirable attributes of brain selectivity and murine-human cross-reactivity, P1C10 affinity was measured and the monomeric dissociation constant for binding to bEnd.3 ECM was 48.38±6.05 nM (FIG. 2D).

As demonstrated in the Examples, brain ECM-targeting polypeptides can specifically target glioblastoma (GBM), an incurable BBB-disrupting brain cancer. Brain ECM binding of VLR clones to murine and human brain tissue sections and freshly resected human GBM was confirmed. After systemic administration, P1C10, one example of the brain ECM-targeting VLR, specifically accumulated at disrupted BBB regions in an intracranial GBM model (FIGS. 3A-3D). The Examples further demonstrate P1C10's ability to target pathologically exposed brain ECM, and deliver P1C10-linked doxorubicin-loaded liposomes which resulted in significantly improved survival in the glioblastoma model (FIGS. 4A-4B and FIGS. 5A-5C).

In certain embodiments, the disclosure relates to isolated polypeptides or antigen binding fragments thereof able to specifically and selectively bind to the brain ECM. By "selectively" or "specifically" we mean a polypeptide capable of binding brain ECM but which does not bind other ECM of other organs or locations within a subject, for example, does not bind to heart, lung, liver, or kidney ECM. By "binding", we mean that the antibodies are capable of detecting brain ECM by standard methods (e.g., tissue section immunofluorescence assays.)

In one embodiment, the present disclosure provides an isolated polypeptide or fragment thereof able to specifically bind to the brain ECM in vivo comprising an amino acid sequence of a variable lymphocyte receptor (VLR) of P1C10 (SEQ ID NO:1) or an amino acid sequence with at least 75%, preferably 80%, 90%, 95%, 98%, 99% or 100% sequence identity to SEQ ID NO:1.

In another embodiment, the present disclosure provides an isolated polypeptide or antigen-binding fragment thereof able to specifically bind to the brain extracellular matrix in vivo comprising an amino acid sequence of a variable lymphocyte receptor (VLR) comprising two or more of the following regions: (i) TXKXHS (SEQ ID NO:3), (ii) IXRXYS (SEQ ID NO:4),(iii) KXYXSW (SEQ ID NO:5), (iv) HXSXGY (SEQ ID NO:6), (v) HXWXLN (SEQ ID NO:7), and (vi) SIVNLQGHGGVD (SEQ ID NO:8), wherein each X is independently selected from any amino acid, and wherein the isolated peptide or antigen-binding fragment thereof is able to specifically bind to the brain extracellular matrix in vivo. Suitably, in some embodiments, the amino acids selected for "X" are capable of proper folding of the VLR into the polypeptide capable of specifically binding to the brain extracellular matrix in vivo. In some embodiments, isolated polypeptide or antigen-binding fragment thereof comprises an amino acid sequence of a variable lymphocyte receptor (VLR) comprising three or more of regions (i)-(vi), alternatively four or more regions of (i)-(vi), alternatively five or more regions of (i)-(vi), alternatively all six regions of (i)-(vi).

In one embodiment, the isolated polypeptide or antigen-binding fragment comprises a VLR comprising an amino acid sequence of $(X)_{11}$TXKXH S $(X)_{15}$IXRXY S $(X)_{18}$KXYXSW$(X)_{18}$HXSXGY$(X)_{18}$HXWXLN$(X)_{21}$ SIVNLQG HGGVD$(X)_{25}$, wherein each X is independently selected from any amino acid.

In one embodiment, the two or more regions, three or more regions, four or more regions, five or more regions, or six regions of the VLR are selected from: (i) SEQ ID NO:11 (TVKCHS), (ii) SEQ ID NO:12 (ILRLYS), (iii) SEQ ID NO:13 (KLYISW), (iv) SEQ ID NO:14 (HLSLGY), (v) SEQ ID NO:15 (HIWLLN), and (vi) SEQ ID NO:8 (SIVNLQGHGGVD).

In one embodiment, the isolated polypeptide or antigen binding fragment comprises the VLR comprising the amino acid sequence of $(X)_{11}$TVKCHS$(X)_{15}$ILRLYS$(X)_{18}$KLYISW$(X)_{18}$HLSLGY$(X)_{18}$HIWLLN$(X)_{21}$SIVNLQGHG GVD$(X)_{25}$ (SEQ ID NO:10), wherein each X is independently selected from any amino acid.

In one preferred embodiment, the isolated polypeptide or antigen binding fragment comprises the amino acid sequence of TVKCHSRRLTSVPAGIPTTTKILRLYSNQITKLEPGVFDHLVNLEKLYISWNQLSALPVGVFDKLTKLTHLSLGYNQLKSVPRGAFDNLKSLTHIWLLNNPWDCECSDILYLKNWI VQHASIVNLQGHGGVD (SEQ ID NO: 16) or a sequence having at least 75% identity with SEQ ID NO:16.

"Any amino acid" for X refers to any amino acid that would maintain the correct conformation to allow for proper folding of the VLR. Amino acids are known in the art and include, for example, glycine (G), alanine (A), valine (V), leucine (L), isoleucine (I), methionine (M), phenylalanine (F), tryptophan (W), proline (P), serine (S), threonine (T), cysteine (C), tyrosine (Y), asparagine (N), glutamine (Q), aspartic acid (D), glutamic acid (E), lysine (K), arginine (R), histadine (H), and selenocysteine (U).

As used herein, the terms "proteins" and "polypeptides" are used interchangeably herein to designate a series of amino acid residues connected to the other by peptide bonds between the alpha-amino and carboxy groups of adjacent residues. The terms "protein" and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, homologs, orthologs, paralogs, fragments and other equivalents, variants, fragments, and analogs of the foregoing. The isolated polypeptides of the present invention are non-naturally occurring peptides that specifically bind the brain ECM in vivo which is normally not accessible unless there has been trauma or damage to the BBB.

Variable lymphocyte receptors, or VLRs, belong to the Leucine-rich repeat (LRR) family and mediate adaptive immune responses in jawless vertebrates, lamprey and hagfish. The VLR are often referred to as the antibodies of jawless fish. The VLRs are assembled in lymphocytes by DNA rearrangements and are as diverse as the conventional antibodies of jawed vertebrates, with the potential to make of over $10^{14}$ unique receptors. VLRs are derived from the assembly of leucine-rich repeat (LRR) gene segments as opposed to the immunoglobulin V, D, and J gene subunits utilized by jawed vertebrates. The VLR consists of a set of LRR modules, each with a highly variable sequence, a 27-34-residue N-terminal LRR (LRRNT), one 25-residue LRR (LRR1), up to nine 24-residue LRRs (VRRVs, the terminal one designated LRRVe), a truncated LRR designated as a connecting peptide (LLRCP) and a 48- to 63-residue C-terminal LRR (LRRCT), as depicted in FIG. 12A.

By "antigen binding fragment thereof" or "fragment thereof" we refer to a portion of the polypeptide that retains its ability to specifically and selectively bind to the brain ECM but not other ECM or cell types. In this application, the antigen is the brain ECM which is not normally exposed to the systemic system when there is a functioning BBB. Suitably, the antigen binding fragment thereof will contain the antigen binding regions of the VLR in order to maintain its ability to selectively and specifically bind to the brain ECM. One skilled in the art, using the methods described in the examples below, will readily be able to determine suitable antigen binding fragments which are able to bind to the brain ECM and which do not bind to other ECM or cells.

The VLRs described in the present disclosure were produced by administering mechanically isolated murine brain microvessel plasma membrane preparations that contained associated brain ECM to a lamprey wherein the lamprey produced VLRs that bind specifically to the brain ECM. This antigen (brain microvessel plasma membrane preparations) is an antigen to which lamprey do not naturally experience exposure, and as such, the isolated polypeptides derived from the methods are non-naturally occurring sequences.

In some embodiments, the isolated polypeptide is a recombinant polypeptide comprising a VLR sequence that is humanized. Suitably, in some embodiments, the polypeptide amino acid sequence is altered to reduce the likelihood of being seen as a foreign antigen and eliciting an immune response when administered to a human subject. Suitable methods to humanize a polypeptide are known in the art. For example, chimeric recombinant polypeptides may be created by swapping in regions of a human protein outside of the antigen binding regions of the VLR.

In one embodiment, a suitable method to humanize a VLR is described in U.S. patent application Ser. No. 15/308,535 ("Variable Lymphocyte Receptors (VLR) Modifications and Compositions and Uses Related Thereto", hereafter "the '535 application"), the contents of which are incorporated by reference in its entirety. For example, in one embodiment, the P1C10 binding moieties described herein are placed into the Slit2-D2 human scaffold (from human leucine-rich repeat receptors) as described in the '535 application. In another embodiment, the VLR may be humanized by linking the VLR to a portion of a human antibody, for example, the human Fc region of a human IgG antibody, as described in the '535 application. The antibodies disclosed in the present invention may be modified to be humanized antibodies which include the constant region from human germline immunoglobulin sequences. The term "recombinant human antibody" includes all human antibodies that are prepared, expressed, created or isolated by recombinant means to include the specific binding regions of the VLRs, such as antibodies isolated from a host cell such as an SP2-0, NS0 or CHO cell (like CHO Kl) or from an animal (e.g., a mouse) that is transgenic for human immunoglobulin genes or polypeptides expressed using a recombinant expression vector transfected into a host cell. Such recombinant human antibodies have constant regions derived from human germline immunoglobulin sequences in a rearranged form.

In some embodiments, the isolated polypeptide has substantial identity to the polypeptide found in SEQ ID NO:1. In some embodiments, the isolated polypeptides have at least 50% sequence identity to SEQ ID NO:1, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the isolated polypeptide has at least 100% sequence identity within the antigen binding regions of the P1C10 to specifically and selectively bind to the brain ECM.

In some embodiments, the isolated polypeptide has substantial identity to the polypeptide found in SEQ ID NO:2. In some embodiments, the isolated polypeptides have at least 50% sequence identity to SEQ ID NO:2, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the isolated polypeptide has at least 100% sequence identity within the antigen binding regions of the P3A8 to specifically and selectively bind to the brain and liver ECM.

The term "substantial identity" of polynucleotide sequences means that a polynucleotide comprises a sequence that has at least 75% sequence identity. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

In some preferred embodiments, the term "substantial identity" of amino acid sequences for purposes of this invention means polypeptide sequence identity of at least 75% identity. Preferred percent identity of polypeptides can be any integer from 75% to 100%. More preferred embodiments include at least 75%, 80%, 85%, 86%, 87%, 88%, 89%, 90%, 91%, 92%, 93%, 94%, 95%, 96%, 97%, 98%, %, or 99%.

In one embodiment, a polypeptide able to bind to brain ECM which is normally not accessible by systemic administration of any antibody is provided. For example, in one embodiment, the polypeptide comprises P1C10 (SEQ ID NO:1) or antigen binding fragments thereof.

In some embodiments, the isolated polypeptide or antigen binding fragment thereof is directly or indirectly linked to an agent. In some embodiments, the isolated polypeptide or antigen binding fragment thereof is covalently or noncovalently linked to an agent. In some embodiments, the isolated polypeptide or antigen binding fragment thereof is conjugated to the agent. In other embodiments, the agent is a polypeptide, wherein the polypeptide is translated concurrently with the VLR polypeptide sequence.

In some embodiments, the agent is selected from the group consisting of a therapeutic agent, pharmaceutical agent, a diagnostic agent, an imaging agent, a detection agent, an immunological therapeutic construct, and a combination thereof.

The term "agent" as used herein includes any useful moiety that allows for the purification, identification, detection, diagnosing, imaging, or therapeutic use of the polypeptide of the present invention. The terms agent includes epitope tags, carriers including therapeutic agent/drug-loaded carriers, detection markers and/or imaging moieties, including, for example, enzymatic markers, fluorescence markers, radioactive markers, among others. Additionally, the term agent includes therapeutic agents, pharmaceutical agents and compounds, small molecules, and drugs, among others. The term agent also includes diagnostic agents. The agent to be attached to a polypeptide described herein is selected according to the purpose of the intended application (i.e., treatment of a particular disease). Such agents may include but are not limited to, for example, pharmaceutical agents, biologics, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radioopaque dyes, radioactive isotopes, fluorogenic compounds, magnetic labels, nanoparticles, marker compounds, lectins, compounds which alter cell membrane permeability, photochemical compounds, small molecules, liposomes, micelles, gene therapy vectors, viral vectors, and the like.

The agents may be linked via cleavable or non-cleavable linkers to the polypeptides described herein. Suitable linkers are known in the art.

In some embodiments, the polypeptide is linked to a biologic that can be targeted to the brain, specifically in some preferred embodiments, a biologic for use in treating a brain injury or disease associated with disruption of the BBB. For example, in one embodiment, the biologics include, but are not limited to, for example, proteinaceous components, for example, other antibody binding domains, trophic factors, neuroactive peptides, among others. For use herein, the term "polypeptide conjugate" includes a polypeptide described above linked directly or indirectly to an agent.

Suitable epitope tags are known in the art and include, but are not limited to, 6-Histidine (His, HHHHHH) cMyc (EQKLISEEDL), FLAG (DYKDDDDK), V5-tag (GK-PIPNPLLGLDST), HA-tag (YPYDVPDYA), NE-tag (TKENPRSNQEESYDDNES), S-tag (KETAAAKFER-QHMDS), Ty tag (EVHTNQDPLD), among others. Epitope tags are commonly used as a purification tag. A purification tag is an agent that allows isolation of the polypeptide from other non-specific proteins.

In one embodiment, the polypeptide is linked with an agent, for example, with a detectable marker, preferably a fluorescent, enzymatic or a luminescent marker. Examples of suitable enzymes include, but are not limited to, horse-radish peroxidase, alkaline phosphatase, beta-galactosidase, glucose-6-phosphatase, or acetylcholinesterase. Examples of suitable tags comprising prosthetic group complexes include, but are not limited to, streptavidin/biotin and avidin/biotin. Examples of suitable fluorescent materials include, but are not limited to, fluorescein, fluorescein isothiocyanate, rhodamine, dichlorot[pi]azinylamine fluorescein, green fluorescent protein (GFP), red fluorescent protein (RFP), blue fluorescent dyes excited at wavelengths in the ultraviolet (UV) part of the spectrum (e.g. AMCA (7-amino-4-methylcoumarin-3-acetic acid); Alexa Fluor 350), green fluorescent dyes excited by blue light (e.g. FITC, Cy2, Alexa Fluor 488), red fluorescent dyes excited by green light (e.g. rhodamines, Texas Red, Cy3, Alexa Fluor dyes 546, 564 and 594), or dyes excited with infrared light (e.g. Cy5) to be visualized with electronic detectors (CCD cameras, photomultipliers); dansyl chloride, phycoerythrin or the like.

Suitable examples of radioactive material include, but are not limited to, $^{125}I$, $^{131}I$, $^{35}S$ or $^{3}H$. In some embodiments, the polypeptide is directly or indirectly linked to a radioisotope, an NMR or MRI contrast agent or nanoparticles for diagnosing, imaging and treatment. Suitable radioisotopes include, but are not limited to, $^{18}$F, $^{11}$C, $^{13}$N, $^{15}$O, $^{68}$Ga, $^{82}$Rb, $^{44}$Sc, $^{64}$Cu, $^{86}$Y, $^{89}$Zr, $^{124}$I, $^{152}$Tb that can be used for PET imaging or $^{67}$Ga, $^{81m}$Kr $^{99m}$Tc, $^{111}$In, $^{123}$I, $^{125}$I, $^{133}$Xe, $^{201}$Tl, $^{155}$Tb, $^{195m}$Pt that can be used for SPECT/scintigraphic studies, or $^{14}$C, $^{3}$H, $^{35}$S, $^{32}$P, $^{125}$I that can be used for autoradiography or in situ hybridisation, or $^{211}$At—, $^{212}$Bi—, $^{75}$Br—, $^{76}$Br—, $^{131}$I—, $^{111}$In, $^{177}$Lu—, $^{212}$Pb—, $^{186}$Re—, $^{188}$Re—, $^{153}$Sm—, $^{90}$Y that can be used to label the polypeptides. Suitable NMR or MRI contrast agents are known in the art and include, but are not limited to, for example paramagnetic agents gadolinium (Gd), dysprosium (Dy) and manganese (Mn), and the superparamagnetic agents based on iron oxide (such as MION, SPIO or USPIO) or iron platinium (SIPP), and X-nuclei such as $^{18}$F, $^{13}$C, $^{23}$Na, $^{17}$O, $^{15}$N.

In further embodiments, the agent is a therapeutic agent. As used herein, the term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, biologics, chemotherapeutics, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, substances used for the treatment, prevention, diagnosis, cure or mitigation of a disease or illness; substances that affect the structure or function of the body, or pro-drugs, which become biologically active or more active after they have been placed in a physiological environment.

As used herein, the term "conjugate" refers to the joining of two entities by covalent bonds. The entities may be covalently bonded directly or through linking groups using standard synthetic coupling procedures. For examples, two polypeptides may be linked together by simultaneous polypeptide expression typically referred to as a fusion or chimeric protein. One or more amino acids may be inserted into polypeptide as a linking group by incorporation of corresponding nucleic acid sequences into the expression vector. Other contemplated linking groups include polyethylene glycols or hydrocarbons terminally substituted with amino or carboxylic acid groups to allow for amide coupling with polypeptides having amino acids side chains with carboxylic acid or amino groups respectively. Alternatively the amino and carboxylic acid groups can be substituted with other binding partners such as an azide and an alkyne which undergo copper catalyzed formation of triazoles.

In another example of conjugation, polypeptides are expressed to contain naturally or non-naturally occurring amino acids containing a thiol group. The thiol group can be substituted for an amino group in coupling reactions with carboxylic acids, or two thiol groups when exposed to oxidative conditions react to form disulfides. Additionally, in some embodiments, non-naturally occurring amino acids are incorporated into the polypeptide, allowing for site-specific conjugation of the polypeptide to one or more agents. For example, in one embodiment, the use of selenocysteine allows for the site-specific conjugation of the polypeptides of the present invention to suitable agents.

In general, methods of conjugating, linking and coupling polypeptides to pharmacologically active compounds are well known in the field. For example, methods of conjugating antibodies can also be used to conjugate polypeptides, see, for example, Wu A M, Senter P D, Arming antibodies: prospects and challenges for immunoconjugates, Nat Biotechnol. 2005 September; 23(9):1137-46 and Trail P A, King H D, Dubowchik G M, Monoclonal antibody drug immunoconjugates for targeted treatment of cancer, Cancer Immunol Immunother. 2003 May; 52(5):328-37; Saito G, Swanson J A, Lee K D. Drug delivery strategy utilizing conjugation via reversible disulfide linkages: role and site of cellular reducing activities, Adv Drug Deliv Rev. 2003 Feb. 10; 55(2):199-215.

Further embodiments contemplated include polypeptide-drug conjugates. For example, suitable drugs may be conjugated to the polypeptides or antigen binding fragments described herein with a cleavable or non-cleavable linker. Cleavable and non-cleavable linkers are known in the art.

Conventional linking methods of linking a substance of interest to a polypeptide are known in the art (e.g., See TERNYNCK and AVRAMEAS, 1987, "Techniques immunoenzymatiques" Ed. INSERM, Paris or G. T. Hermanson, Bioconjugate Techniques, 2010, Academic Press). Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on polypeptide cross-linking and conjugate preparation is: WONG, Chemistry of protein conjugation and cross-linking, CRC Press (1991).

In some embodiments, the polypeptides may be provided in combination with liposome, nanoparticles or other analogous carriers loaded with a pharmaceutically active compound (e.g., therapeutic agent or drug). Methods of preparing such compositions are known in the field (see, for example, Sugano et al., Antibody Targeting of Doxorubicin-loaded Liposomes Suppresses the Growth and Metastatic Spread of Established Human Lung Tumor Xenografts in Severe Combined Immunodeficient Mice Cancer Research 60, 6942-6949, Dec. 15, 2000 and Martin et al., Nanomaterials in Analytical Chemistry, Analytical Chemistry News & Features, May 1, 1998; pp. 322 A-327 A). As used herein, the phrase "isolated polypeptide in combination with a pharmaceutically active compound" shall not be limited by the method of manufacture and such compositions may be produced by, but not limited to, techniques of conjugating, linking, coupling and decorating known in the art.

In some examples, the isolated peptide or antigen-binding fragment thereof can be conjugated to the carrier in order to deliver a drug or therapeutic to the brain. Suitable carriers are known in the art and include, but are not limited to, for example, liposomes, polymeric micelles, microspheres, and nanoparticles.

Liposomes are structures which consist of at least one lipid bilayer surrounding an aqueous core. Suitable liposomes are known in the art, for example, but not limited to, examples described in Allen and Cullis "Liposomal drug delivery systems: From concept to clinical applications" Advanced Drug Delivery Reviews, 65:1 (January 2013) pp. 36-48; Alavi et al. "Application of Various Types of Liposomes in Drug Delivery Systems" Adv. Pharm Bull 2017 April:7(1):3-9, and Torchilin and Weissig "Liposomes, A Practical Approach" Oxford University Press, 2003: Second Edition, the contents of which are incorporated by reference in their entireties. Suitable methods of conjugating liposomes to the antibodies are also known in the art, including DBCO or azide reactive liposomes (e.g., DBCO-PEG2000-DSPE liposomes), among others. For example, but not limited to, suitable methods are described in Whitehead et. al. "Artificial Membrane Fusion Triggered by Strain-Promoted Alkyne-Azide Cycloaddition" Bioconjugate Chem. 2017, 28, 4, 923-932 DOI: 10.1021/acs.bioconjchem.6b00578, the contents of which are incorporated by reference in its entirety.

In some embodiments, the liposomes are used to deliver a therapeutic agent (e.g. drug) to the site of disease or injury. Suitable methods of loading liposomes with therapeutic agents are known in the art. For example, suitable therapeutic agents that can be loaded to the polypeptide-conjugated liposomes include, for example, chemotherapeutic drugs among others as described below.

In one embodiment, the polypeptide-conjugated liposomes comprise a drug able to treat or target glioblastoma. For example, in one embodiment, the drug is doxorubicin, temozolomide, or a checkpoint inhibitor(s0 (e.g., antibodies against PD-1, PD-L1, or CTLA-4). .

Suitable nanoparticles, including metal nanoparticles and other metal chelates, are known in the art and include, but are not limited to, for example, gold nanoparticles (B. Van de Broek et al., ACSNano, Vol. 5, No. 6, 4319-4328, 2011), quantum dots (A. Sukhanova et al., Nanomedicine, 8 (2012) 516-525), magnetic nanoparticles ($Fe_3O_4$), silver nanoparticles, nanoshells and nanocages.

In some embodiments, the agent can be a portion or fraction of an immunoglobulin (i.e., antibody). For example, in one embodiment, the agent can be an fraction crystallizable region (Fc) portion of an antibody. The Fc region is the tail region of an antibody that interacts with cell surface receptors called Fc receptors and some proteins of the complement system. Fc binds to various cell receptors and complement proteins. In this way, it mediates different physiological effects of antibodies (detection of opsonized particles; cell lysis; degranulation of mast cells, basophils, and eosinophils; and other processes). The Fc regions define the class (or isotype) of antibody (e.g., IgG) and are responsible for binding a number of natural proteins to elicit important biochemical events. The Fc region of an antibody interacts with a number of ligands including Fc receptors and other ligands, imparting an array of important effector functions, including, for example, antibody dependent killing and increased circulation. In IgG, IgA and IgD antibody isotypes, the Fc region is composed of two identical protein fragments, derived from the second and third constant domains of the antibody's two heavy chains; IgM and IgE Fc regions contain three heavy chain constant domains (CH domains 2-4) in each polypeptide chain.

In one embodiment, the agent is the Fc of a human IgG. Suitably, the Fc portion of the Ig may be from a mammalian immunoglobulin (e.g., rabbit, rat, human, etc), preferably in one embodiment, from a human Ig.

One may wish to express the isolated polypeptide as a fusion protein with a pharmacologically or therapeutically relevant peptide. For example, one may wish to express the VLR with a protein linker and a protein therapeutic. Standard molecular biology techniques (e.g., restriction enzyme based subcloning, or homology based subcloning) could be used to place the DNA sequence encoding a protein therapeutic in frame with the VLR within the targeting vector (usually a protein linker is also added to avoid steric hindrance). The fusion protein is then produced as one peptide in a host cell (e.g., yeast, bacteria, insect, or mammalian cell) and purified before use. Note the therapeutic does not need to be a whole protein. (For example, it can be a single peptide chain as a subunit in a protein with more than one peptide. The other peptides can be co-expressed with the vector fusion and allowed to associate in the host cell or after secretion). For example, in one embodiment, the fusion protein may be the amino acid sequence comprising the VLR and the amino acid sequence of human Fc IgG.

In some embodiments, the present disclosure provides compositions comprising the isolated polypeptide and a pharmaceutically acceptable carrier.

The present disclosure provides compositions comprising a polypeptide specific for brain EMC described above. In some embodiments, the composition is a pharmaceutical composition comprising the polypeptide specific for brain EMC and a pharmaceutically acceptable carrier. Compositions are provided that include one or more of the disclosed polypeptides that bind brain EMC. Compositions comprising poylpeptides that are conjugated to and/or directly or indirectly linked to an agent are also provided. The compositions can be prepared in unit dosaged forms for administration to a subject. The amount and timing of administration are at the discretion of the treating clinician to achieve the desired outcome. The polypeptide can be formulated in the composition for systemic or local (such as intravenous, intrathecal, intra-cranial) administration depending on the specific method for use (e.g., detection, diagnostic, treatment (e.g., administered with a therapeutic or pharmaceutical agent). In one example, the polypeptide is formulated for parenteral administration, such as intravenous administration.

In some embodiments, the composition comprises effective amounts of the polypeptide and a pharmaceutical agent together with a pharmaceutically acceptable carrier.

"Pharmaceutically acceptable" carriers are known in the art and include, but are not limited to, for example, suitable diluents, preservatives, solubilizers, emulsifiers, liposomes, nanoparticles and adjuvants. Pharmaceutically acceptable carriers are well known to those skilled in the art and include, but are not limited to, 0.01 to 0.1 M and preferably 0.05M phosphate buffer or 0.9% saline. Additionally, such pharmaceutically acceptable carriers may be aqueous or non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media. Water is not contemplated as a suitable physiologically acceptable carrier. In some embodiments, additional components may be added to preserve the structure and function of the viruses, vectors or polypeptides of the present invention, but are physiologically acceptable for administration to a subject.

Compositions of the present disclosure may include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e. g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the polypeptide, complexation with metal ions, or incorporation of the material into or onto particulate preparations of polymeric compounds such as polylactic acid, polyglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

In some embodiments, the compositions comprise a pharmaceutically acceptable carrier, for example, buffered saline, and the like. The compositions can be sterilized by conventional, well known sterilization techniques. The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

In some embodiments, the polypeptides are provided in lyophilized form and rehydrated with sterile water or saline solution before administration.

Further embodiments provide an isolated nucleic acid sequence that encodes for the polypeptides described above. Some embodiments provide an isolated polynucleotide encoding the polypeptide described herein. In one embodiment, the isolated polynucleotide encodes the VLR comprising SEQ ID NO:1. In some embodiments, the isolated nucleic acid sequence encoding the isolated polypeptide or antigen binding fragments thereof described herein are provided.

A recombinant expression cassette comprising a polynucleotide encoding the polypeptide or antigen binding fragment thereof is also contemplated. The polynucleotide or antigen binding fragment thereof can be under the control of a transcriptional promoter allowing the regulation of the transcription of said polynucleotide in a host cell.

The present disclosure also provides a recombinant expression cassette comprising a polynucleotide or antigen binding fragment thereof according to the present invention under the control of a transcriptional promoter allowing the regulation of the transcription of said polynucleotide in a host cell. Said polynucleotide can also be linked to appropriate control sequences allowing the regulation of its translation in a host cell.

The present disclosure also provides a recombinant vector (e.g., a recombinant expression vector) comprising a polynucleotide according to the present invention. Advantageously, said recombinant vector is a recombinant expression vector comprising an expression cassette according to the present invention.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Vectors, including expression vectors, comprise the nucleotide sequence encoding for the polypeptides described herein and a heterogeneous sequence necessary for proper propagation of the vector and expression of the encoded polypeptide. The heterogeneous sequence is sequence from a difference species that the polypeptide.

The present disclosure also provides a host cell containing a recombinant expression cassette or a recombinant expression vector according to the present invention. The host cell is either a prokaryotic or eukaryotic host cell. The host cell is capable of expressing the polypeptides of the present invention. Suitable host cells include, but are not limited to, mammalian cells and yeast cells. In some embodiments, the host cell may be a eukaryotic cell. The terms "host cell" refers to a cell into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The present disclosure contemplates methods of delivering an agent, for example, but not limited to, a pharmaceutically active or otherwise therapeutic compound to a subject's brain. Such a method includes administering a composition comprising the isolated polypeptide described herein and an agent, for example, a pharmaceutically active or therapeutic compound to a subject. The isolated polypeptide directs delivery of the agent to the site of BBB disturbance which allows exposure of the brain ECM and allows the pharmaceutically active agent to accumulate in the subject's brain. As described in more detail above, the agent may be directly or indirectly linked to the isolated polypeptide specific for the brain ECM. Suitable peptides include, for example, polypeptide comprising P1C10 (SEQ ID NO:1) or an antigen binding fragment thereof.

The polypeptides or antigen fragments thereof can be used as a diagnostic tool, both in the clinical and laboratory setting (e.g., in vitro and in vivo). Suitable diagnostic uses include, but are not limited to, for example, detection, labeling and imaging of brain ECM using the polypeptides or antigen binding fragments thereof described herein. In one embodiment, the present disclosure provides a method of detecting brain ECM in a sample, the method comprising contacting the sample with the polypeptide or antigen binding fragment thereof and detecting the polypeptide or antigen binding fragment thereof within the sample. Suitable methods of detection include, but are not limited to, for example, visualization or imaging of a labeled polypeptide or antigen binding fragment thereof. In vitro methods of visualization can be by microscope (e.g., fluorescence microscopy), flow cytometry, cryo-imaging, 3-D imaging, and the like. Suitable methods of in vivo visualization include, but are not limited to, for example, PET scan, MRI scan, CT scan, NMR, among others.

Another embodiment of the present disclosure provides a method of detecting and labeling brain ECM within a subject. This may be desirable in cases in which there has been BBB disruption in the subject, allowing for the exposure of the ECM to the systemic blood system. The method comprises administering to the subject an isolated polypeptide specific to brain ECM as described herein. In some instances, the method can be performed before brain surgery to assess the integrity of the blood brain barrier. In some embodiments, the isolated polypeptide may be conjugated to an imaging or fluorescent or other visualizable agent that can be used to detect the brain ECM within the brain. Methods of imaging are known in the art and include, but are not limited to, for example, PET scan, MRI scan, CT scan, NMR, among others.

The present disclosure also contemplates methods of detecting or imaging the brain ECM within a subject. The method comprises, administering to the patient a suitable amount of the isolated polypeptide directly or indirectly linked with a diagnostic or detecting agent.

Another embodiment provides a method of imaging brain ECM in a subject comprising (a) administering to the subject an isolated polypeptide comprising a VLR described herein conjugated to an imaging agent, and (b) visualizing the localization of the polypeptide in the subject. Methods of visualizing the polypeptide are known in the art, and will depend on the imaging agent attached to the polypeptide as described above. Suitable methods of visualization of the brain ECM within the subject include, but are not limited to, PET scan, MRI scan, CT scan, among others. In some embodiments, the visualization occurs in the brain of the subject.

As used herein "subject" or "patient" refers to mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In one specific embodiment, a subject is a mammal, preferably a human.

As used herein, the terms "administering" and "administration" refer to any method of providing a pharmaceutical preparation or composition to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically; that is, administered to treat an existing disease or condition. In a preferred embodiment, the administration is intracerebral administration or intravenous administration.

For purposes of the present invention, "treating" or "treatment" describes the management and care of a subject for the purpose of combating the disease, condition, or disorder. Treating includes the administration of a polypeptide of present invention in combination with a therapeutic or pharmaceutical agent to prevent the onset of the symptoms or complications, alleviating the symptoms or complications, or eliminating the disease, condition, or disorder.

In some embodiments, kits for carrying out the methods described herein are provided. The kits provided may contain the necessary components with which to carry out one or more of the above-noted methods.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon consideration of the following non-limiting examples.

EXAMPLES

Example 1: Identification of Variable Lymphocyte Receptors that Can Target Therapeutics to Pathologically Exposed Brain Extracellular Matrix This Example demonstrates the identification and use of variable lymphocyte receptors (VLRs) that accumulate in pathologically-exposed brain extracellular matrix (ECM) for therapeutic targeting of brain diseases. The novel, moderate throughput screening assay described in this study was suitable for identification of VLRs that specifically bind brain ECM. In particular, coupling an ECM biopanning protocol with a differential ECM-binding ELISA that simply used VLRs cleaved directly from the yeast surface enabled rapid identification of brain ECM-specific binders. In addition, the principles of this novel screening assay could be applied to identify targeting ligands that bind ECM derived from other organs or disease states.

Unlike typical therapeutic strategies that are designed to target disease-specific, cell intrinsic markers[33,47] this Example shows that targeting of pathologically exposed ECM could be effective in neurological diseases that exhibit differential BBB permeability, such as glioblastoma (GBM). Another advantage is that there are available techniques to artificially expose sequestered ECM via local BBB disruption such as targeted ultrasound.

The VLRs identified in our work bind normal brain ECM, and strategically use the pathological exposure of normal ECM for targeting specificity. This approach could therefore obviate the need to identify a disease-specific target, and the ECM-targeting VLRs could be customized for any neurological disease that exhibits BBB disruption (or via artificial BBB disruption) by simply altering the therapeutic payload. Finally, the initial immunohistochemical and biodistribution analyses with VLR clone P1C10 demonstrated a high brain ECM specificity compared to peripheral tissues, indicating that brain ECM can serve as a "specific" target when coupled with pathological disruption of BBB barrier properties. Thus, this strategy represents a significant departure from existing platforms that focus on targeting disease-related cell-intrinsic markers and/or schemes to circumvent the BBB.

This study used an implantable GBM murine model to demonstrate the functional relevance of targeting pathologically permeable BBB to deliver therapeutics to GBM. Implantable U87 GBM is a commonly used pre-clinical model.[33-35] Benefits include human tumor origin, controlled tumor initiation, and the ability to implant intracranially in SCID mice. Previous studies have demonstrated that treating U87 intracranial glioma with IL-13- or 2C5 nucleosome-recognizing antibody-targeted doxorubicin-loaded liposomes significantly reduced tumor burden.[33,35] Similarly, P1C10 targeting resulted in doxorubicin accumulation within GBM xenografts, reduced in vitro $EC_{50}$, and significantly improved survival. All treatment groups in this study were administered equal amounts of VLR-conjugated doxorubicin-loaded liposomes. Thus, the therapeutic benefit observed with P1C10 VLR is directly related to its specific targeting of BBB disrupted regions, and the biodistribution data suggest that the therapeutic benefit results from enhanced accumulation of doxorubicin selectively within the GBM.

To test the potential benefits of ECM-targeted drug delivery, we first applied the concept to the incurable brain cancer, GBM. Better GBM therapies are sorely needed because patients have a uniformly poor prognosis with median survival of less than 2 years despite aggressive clinical treatments of surgery, chemotherapy, and radiation (13, 14). Recent data indicate that GBM targeting of immunotherapy through interleukin-13 (IL-13)—targeted chimeric antigen receptor (CAR) T cells could have marked effects for a short time in selected patients, and CAR T cells targeting chondroitin sulfate proteoglycan 4 recently demonstrated efficacy in a murine model (11, 12, 15). Thus, targeting of GBM and, specifically, ECM components could offer new treatment strategies. In addition, central or internal GBM regions exhibit disrupted BBB revealed by magnetic resonance imaging enhancement with gadolinium contrast, suggesting compatibility with ECM-targeted approaches (6, 16). Thus, we hypothesized that pathologically exposed brain ECM in GBM could be targeted for therapeutic purposes.

While standard peptides and antibodies could be used as ECM-targeting reagents, we chose to deploy lamprey antigen receptors known as variable lymphocyte receptors (VLRs) (17). VLRs are crescent-shaped, leucine-rich repeat proteins that recognize antigenic targets with specificity and affinity comparable to immunoglobulin (Ig)-based antibodies (1, 18, 19). Combining the unique binding site geometry with the approximately 500 million years of evolutionary distance between lamprey and mammals, VLRs could possibly recognize conserved proteins and glycans in ECM that may not be effectively targeted by mammalian antibodies (17-19). To identify VLRs that bind brain ECM, we screened an immunized lamprey VLR library in yeast surface display format by biopanning. The resultant enriched pool of ECM-binding clones was subsequently assayed for preferential binding to brain ECM using a moderate throughput, enzyme-linked immunosorbent assay (ELISA)-based screen. The lead clone demonstrated preferential accumulation at disrupted BBB sites in animals with osmotic BBB disruption or intracranial GBM tumors and also effectively targeted doxorubicin-loaded liposomes to improve survival.

Results

Identification of Brain ECM-Binding VLRs

Brain ECM-binding VLRs were identified by mining a yeast surface display library of VLRs. The library was generated from the VLR repertoire of lamprey immunized with mechanically isolated murine brain microvessel plasma membrane preparations that contained associated brain ECM (20). The library was first enriched for ECM binders via two rounds of biopanning on decellularized ECM generated by cultured mouse brain endothelial cells (bEnd.3 cell line). Next, we sought to identify ECM-binding clones that preferentially bound bEnd.3 ECM compared to control mouse fibroblast ECM (3T3 cell line). For this analysis, we picked individual yeast clones into 96-well plates and then expanded and induced them for VLR display. To enable moderate throughput analysis of the clones and avoid cumbersome subcloning of many VLR clones, we removed the VLRs directly from yeast surface via reduction. After removal, we evaluated the comparative binding of VLRs to bEnd.3 and 3T3 ECM via ELISA screening (FIG. 1A). In total, 285 clones were assayed for differential binding, and observed binding signals were as high as ~5-fold preference for bEnd.3 ECM (FIG. 1B). Ten clones demonstrated at least a 2.5-fold preference for bEnd.3 ECM. To further validate the ELISA-based screening method, the individual VLR-displaying yeast clones were panned against both bEnd.3 and 3T3 ECM and imaged via bright-field microscopy. For example, yeast displaying clones P1C10 and P2C7 (ELISA fold change, 4.2 and 4.5, respectively) bound selectively to bEnd.3 ECM compared to 3T3 ECM, whereas a nonbinding VLR clone P1E9 showed very little ECM binding (FIG. 1C, P1E9).

Next, to confirm the in vivo relevance of ECM-binding VLR candidates, they were assayed for binding to murine brain sections. Eight of the top 10 VLR clones from the ELISA screen showed binding to murine brain sections (FIG. 1D). Two VLRs, including the P3E11 clone shown in FIG. 1D, did not show brain tissue labeling despite their binding to cell culture ECM. Each of the binding clones demonstrated a diffuse parenchymal brain ECM immunolabeling pattern, with no apparent vascular or cell type enrichment despite the fact that brain endothelial cell ECM was used as the biopanning substrate. Given their positive binding and substantial bEnd.3 ECM selectivity in the ELISA assay, P1C10 and P3A8 were subjected to more detailed evaluation.

P1C10 Displays Brain-Selective ECM Binding

P1C10 and P3A8 were cloned into our previously described intein fusion yeast display system that allows site-specific modification of the VLR at the C terminus (21). In this way, P1C10 and P3A8 were functionalized with Cy5 fluorescent dye (22). Direct immunolabeling of murine tissues using VLR-Cy5 conjugates indicated that P1C10-Cy5 had substantial brain ECM selectivity compared to kidney (10.1-fold increase), heart (20.2-fold increase), and liver (5.7-fold increase) tissues (FIG. 2A). In contrast, P3A8-Cy5 bound both brain and liver ECM with similar intensity but, like P1C10-Cy5, also did not show binding to kidney and heart tissues (FIG. 7). Next, we tested the ability of P1C10 to cross-react with human brain ECM using human brain cryosections. P1C10-Cy5 bound human brain ECM compared with controls, with a pattern similar to that observed in murine brain sections (FIG. 2B). Furthermore, P1C10-Cy5 also bound to ECM in cryosections of freshly resected human GBM specimens (FIG. 2C). Given the desirable attributes of brain selectivity and murine-human cross-reactivity, P1C10 affinity was measured and the monomeric dissociation constant ($K_d$) for binding to bEnd.3 ECM was 48.38±6.05 nM (FIG. 2D).

Brain ECM-Binding VLR is Retained within Brain after BBB Disruption

We next evaluated whether P1C10 would accumulate at sites of BBB disruption by using hyperosmolar mannitol for transient global BBB disruption in murine brain (23). P1C10 or RBC36 modified with $IR_{800}$ near-infrared dye was administered intravenously at 1 mg/kg to healthy C57BL/6 mice. RBC36 is a VLR that recognizes human H antigen trisaccharide (18) and was used as an isotype control. Next, mannitol was administered intravenously to transiently open the BBB. With the BBB still disrupted, mice were perfused to remove unbound VLR. We resected and imaged whole brains for retained $IR_{800}$ signal (FIGS. 3A-3D). Mice treated with P1C10-$IR_{800}$ had a significant, 3.3-fold increase in accumulated brain fluorescence compared to RBC36-$IR_{800}$ and a 7.6-fold increase compared to saline-treated animals. Thus, P1C10 selectively accumulates in normal brains after transient BBB disruption.

Brain ECM-Binding VLRs Selectively Accumulate within Intracranial GBM

Figure 4A:
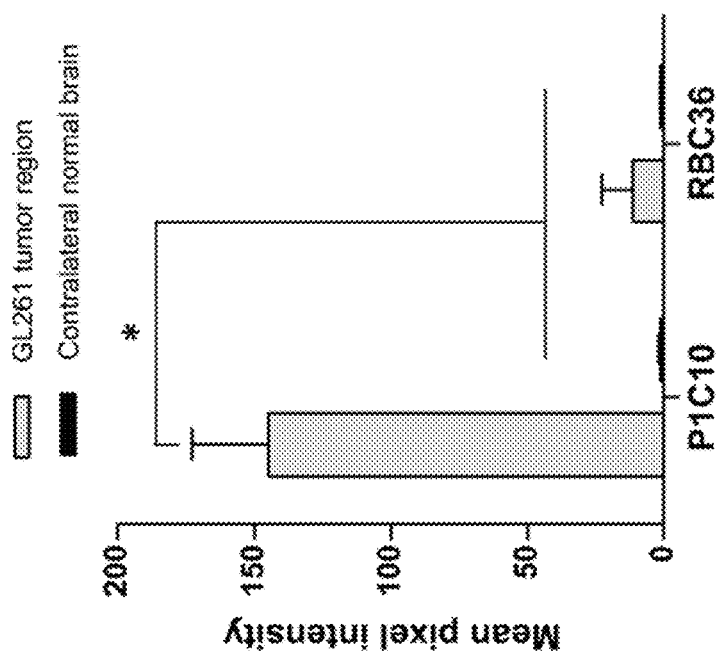
FIGS. 4A-4B. Tissue accumulation of VLRs after systemic administration in GBM models. (A) C57BL/6 mice, bearing GL261 intracranial tumors, were intravenously administered VLR-IR800 (1 mg/kg). After 30 min, mice were perfused and the brains resected and imaged for IR800 signal (green). H&E images of coronal brain sections are depicted above the IR800 signal for representative mice, T represents the tumor region in each image and the tumor region is outlined. Signal from GL261 tumor region and normal contralateral brain was quantified (means±SD, n=3 mice per group; *P<0.01, ANOVA). (B) VLR-Fc fusions (3 mg/kg) were administered via tail vein injection to SCID mice bearing intracranial U87 GBM and allowed to circulate for 30 min. After full-body perfusion, organs were harvested, sectioned, and probed for Fc region (VLR, green), blood vessels (GS-IB4, magenta), and nuclei (Hoechst 33342, blue). Columns from left to right are U87 tumor region, normal contralateral brain, kidney (focused on a glomerulus), heart, and liver. Scale bars, 20 µm. Accumulated VLR-Fc fluorescence signal intensity is quantified below the images for each tissue (*P<0.01, comparing VLR, U87 tumor signal for either P1C10-Fc or 192-Fc to RBC36-Fc, t test. $P<0.01 for P1C10-Fc U87 tumor signal compared to all other tissues, ANOVA. &P<0.05 for 192-Fc U87 tumor signal compared to all other tissues, ANOVA. €P<0.05 for 192 VLR signal within a tissue type compared to P1C10 or RBC36, ANOVA).
Figure 4B:
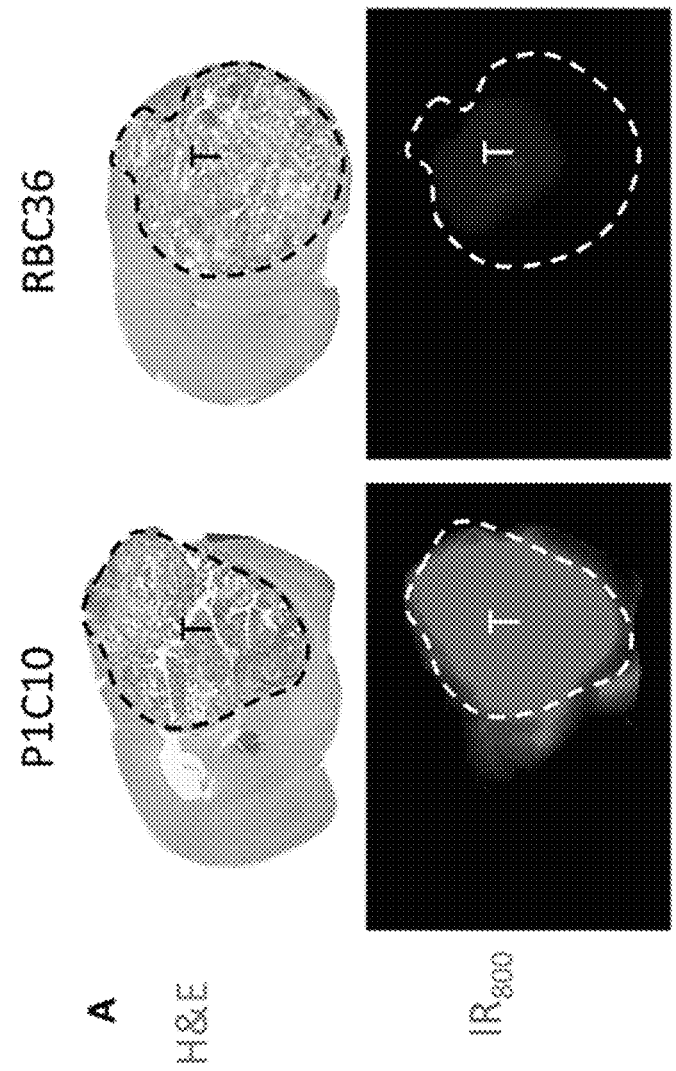
Figures 4A, 4B:
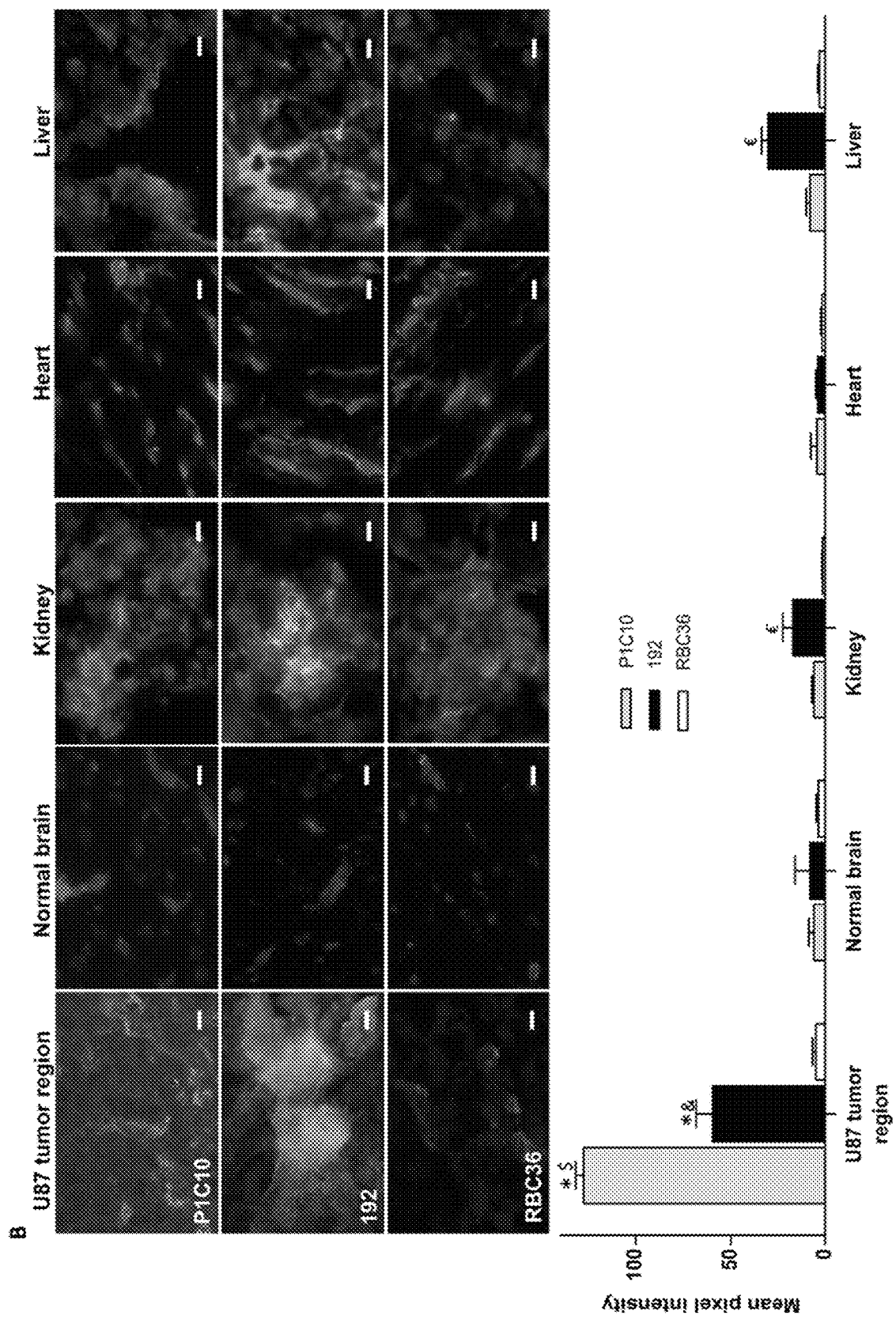

We used two different intracranial GBM models to test the hypothesis that pathological exposure of brain ECM can also be targeted by the identified VLRs. Intracranial implantation of murine GL261 or human U87 GBM cells results in brain tumors that exhibit chaotic vasculature and regional BBB disruption (24-26). First, P1C10 or RBC36 (1 mg/kg) isotype control (both modified with $IR_{800}$ near-infrared dye) were intravenously administered to C57BL/6 mice bearing syngeneic, intracranial GL261 GBM. VLRs circulated for 30 min before mice were perfused, brain resected, and imaged for $IR_{800}$ signal. The mean fluorescence intensity of the GL261 tumor region for mice treated with P1C10-$IR_{800}$ was 112-fold higher than that of the contralateral brain region (FIG. 4A). By contrast, the fluorescence intensity of the GL261 tumor region for mice treated with control RBC36-$IR_{800}$ was only increased ninefold compared with contralateral brain. Moreover, the accumulated P1C10-$IR_{800}$ in tumor was 13-fold higher than that observed for control RBC36-$IR_{800}$. Together, these data indicate that P1C10-$IR_{800}$ selectively accumulated within GL261 orthotopic tumors. Next, given the capability to target pathologically exposed ECM in mouse tumors, we also tested whether P1C10 could target ECM in orthotopically implanted human tumors. VLR uptake was monitored after VLRs were administered as above to severe combined immunodeficient (SCID) mice bearing intracranial U87 GBM tumors. In addition to P1C10, which exhibits diffuse binding to brain ECM, we also evaluated another VLR (192, identified in our laboratory), which binds much more selectively to the basolateral side of the brain vasculature in addition to kidney and liver vessels and ECM (FIGS. 8A-8B) (20). P1C10, 192, and RBC36 were fused to a rabbit Fc region (VLR-Fc) to facilitate avidity and detection while minimizing renal clearance. VLR-Fc (3 mg/kg each) was administered intravenously and allowed to circulate for 30 min. After full-body perfusion, organs were removed, sectioned, and imaged for the presence of VLR-Fc. Both VLR clones P1C10-Fc and 192-Fc accumulated within the margins of the GBM, with P1C10-Fc being distributed throughout the tumor ECM (FIG. 4B). While 192-Fc exhibited some parenchymal distribution, it was more concentrated outside of large tumor vessels (FIG. 4B), recapitulating the perivascular binding pattern observed in tissue section labeling assays. Neither VLR appreciably accumulated in the normal contralateral brain hemisphere from the same mouse, and isotype control RBC36-Fc was not found in tumor or normal brain regions (FIG. 4B). P1C10-Fc did not preferentially accumulate above background in treated mouse kidney, heart, or liver sections. In contrast, we found 192-Fc signal proximal to blood vessels of renal glomeruli and liver sinusoidal blood vessels (FIG. 4B). Quantitatively, P1C10-Fc demonstrated a 21.2-fold increase in U87 tumor compared to contralateral controls, as well as increases of 21.2-fold compared to kidney, 15.9-fold compared to liver, and 29.6-fold compared to heart. Both P1C10-Fc (25.4-fold) and 192-Fc (11.9-fold) yielded increased accumulation in U87 tumor regions compared to the RBC36-Fc control. Both distributions mirrored those suggested by tissue section labeling (FIGS. 2A-2E and FIGS. 8A-8B). Together, both P1C10-Fc and 192-Fc specifically target and preferentially accumulate at regions of vascular disruption in GBM, with P1C10-Fc displaying more brain specificity.

VLRs can be Conjugated to Doxorubicin-Loaded Liposomes

Figures 5A, 5B, 5C:
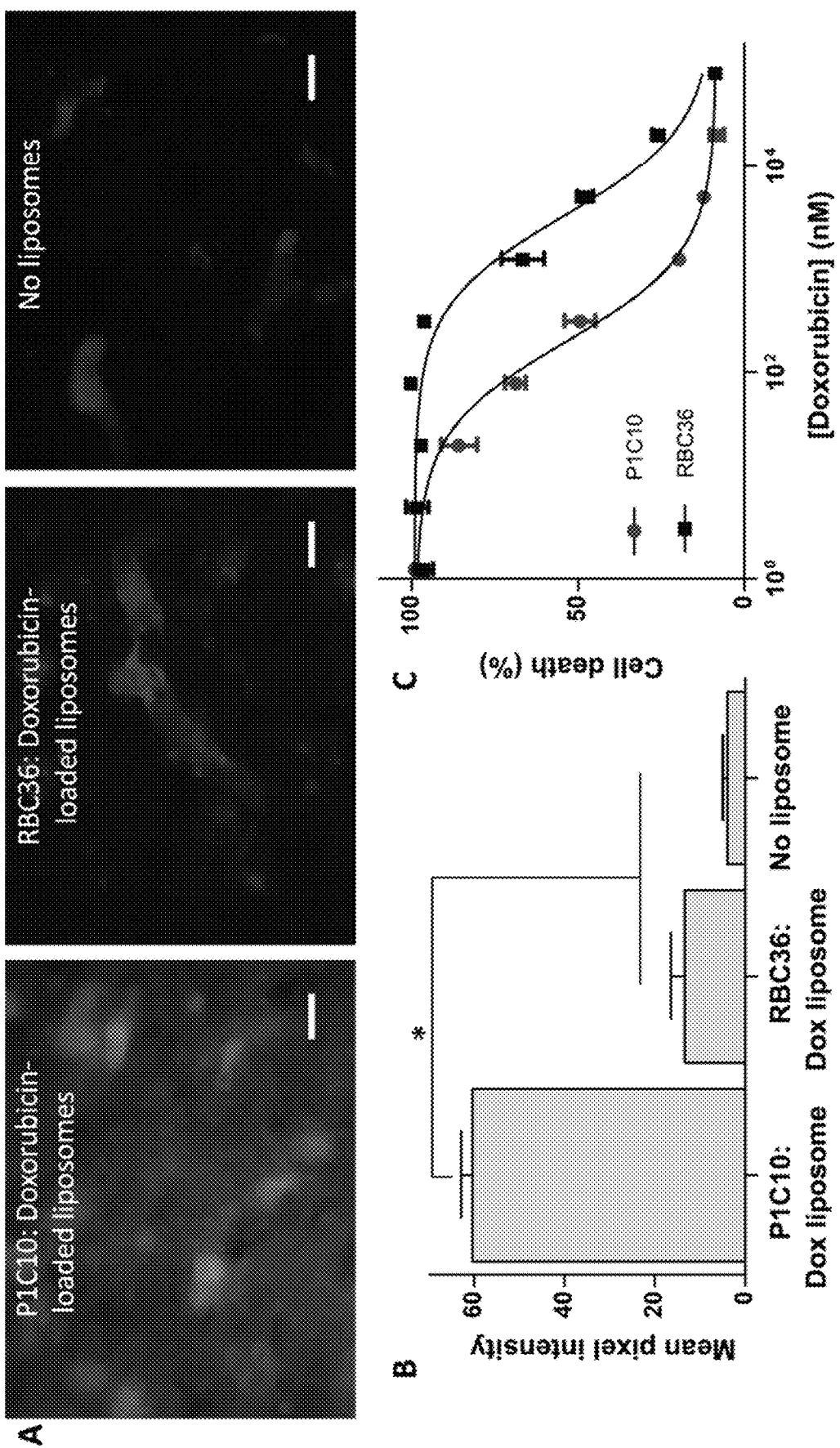
FIGS. 5A-5C. Characterization of P1C10-targeted doxorubicin-loaded liposomes. (A) VLR-targeted doxorubicin-loaded liposomes were used in a binding assay with murine brain tissue sections and imaged for doxorubicin fluorescence (green). GS-IB4 lectin labels microvessels (magenta), and cell nuclei are stained with Hoechst 33342 (blue). (B) Doxorubicin fluorescent signal, from groups presented in (A), is quantified for each group (*P<0.01, ANOVA). (C) U87 cell viability as a function of doxorubicin concentration provided by VLR-conjugated doxorubicin-loaded liposomes bound to bEnd.3 ECM. The EC$_{50}$ was determined by seeding U87 cells onto bEnd.3-derived brain ECM, incubating with VLR-conjugated doxorubicin labeled liposomes, washing unbound liposomes, and then culturing for 72 hours at which point the cell viability was measured. All dilutions were performed in triplicate. EC$_{50}$ for P1C10=199.0±1.7 nM and RBC36=3312.0±2.6 nM (P <0.05, Student's t test).
Figures 9A, 9B, 9C:
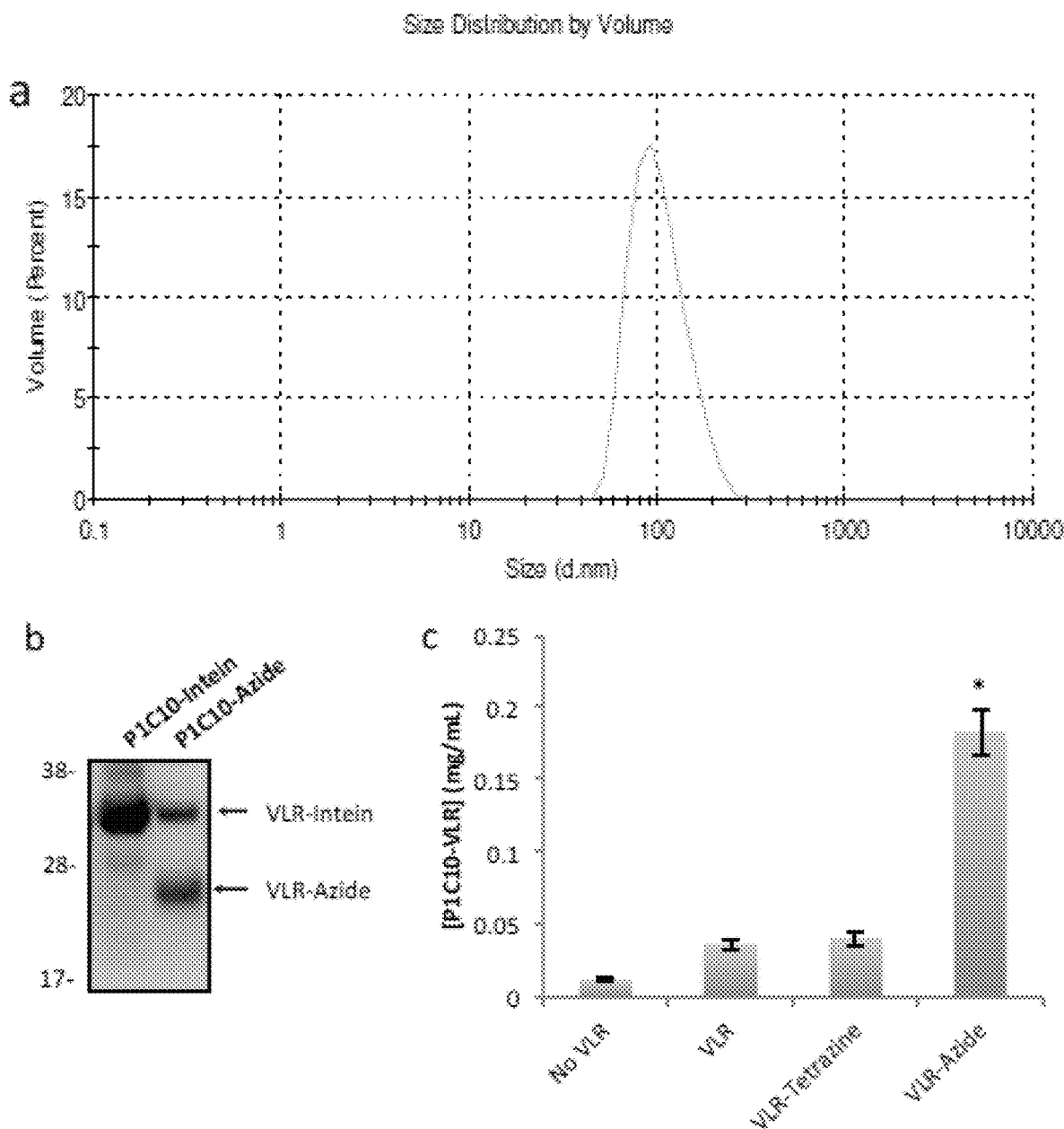
FIGS. 9A-9C. Characterization of doxorubicin-loaded liposomes. (A) Doxorubicin-loaded liposomes were sized using dynamic light scattering. Formed liposomes demonstrated a narrow size distribution with mean diameter of 94.2 nm. (B) Anti-Flag western blot of P1C10-Intein fusion in lane 1 and P1C10 that has undergone EPL to append an azide at the carboxy-terminus in lane 2. (C) VLRs are incubated with liposomes that contain DSPE-PEG2000-DBCO. Compared are a no VLR group, a VLR with no chemically reactive carboxy-terminal group, a VLR with a non-DBCO reactive tetrazine at its carboxy-terminus and the VLR with a DBCO-reactive azide at its carboxy-terminus. After removal of excess protein, the amount of protein present in each liposome group is quantified using a BCA assay (* p<0.05 using ANOVA).

Given the targeting specificity of P1C10, we wished to test the effectiveness of ECM targeting for therapeutic delivery. Thus, we next used VLRs to decorate doxorubicin-loaded liposomes as a proof-of-principle exploration of pathologically exposed ECM for therapeutic targeting in GBM. Doxorubicin was chosen as the test drug because it is easily visualized due to intrinsic fluorescence, there is abundant literature describing liposome loading and tumor targeting, and doxorubicin is a substrate for drug efflux transporters in cancer and at the BBB (24, 25, 27). Pegylated liposomes were loaded with doxorubicin as previously described (28). Resultant liposomes had a median diameter of 94.2 nm and contained doxorubicin (1 to 2 mg/ml; FIGS. 9A-9C). Next, we prepared VLR-intein fusion protein for attachment by installing an azide group at the C terminus of the VLR as previously described (FIGS. 9A-9C) (22). The azide-functionalized VLRs were next attached to the liposome surface by reacting with a strained cyclooctyne (DBCO) that was doped into the liposome formulation (DBCO-PEG2000-DSPE). Specific VLR attachment was confirmed by measuring a significant increase in protein concentration in liposomal formulations having the VLR-azide (FIGS. 9A-9C). Last, VLRs retained their binding activity after immobilization on the liposome surface as demonstrated by a 4.5-fold increase in doxorubicin signal for P1C10-targeted liposomes binding to murine brain sections compared to RBC36-targeted control liposomes (FIGS. 5A-5C). To demonstrate the feasibility of performing treatment studies with VLR-targeted doxorubicin-loaded liposomes, we incubated U87 GBM cells cultured on bEnd.3 ECM with P1C10- or RBC36-targeted doxorubicin-loaded liposomes in vitro (FIGS. 5A-5C). We observed an enhanced cell killing with P1C10-targeted liposomes with a median effective concentration ($EC_{50}$) of 199.0±1.7 nM compared with an $EC_{50}$ of 3312.0±2.6 nM for RBC36-targeted liposomes.

P1C10-Targeted Liposomes Significantly Extend Survival of GBM-Bearing Mice

Figures 6A, 6B, 6C, 6D, 6E, 6F:
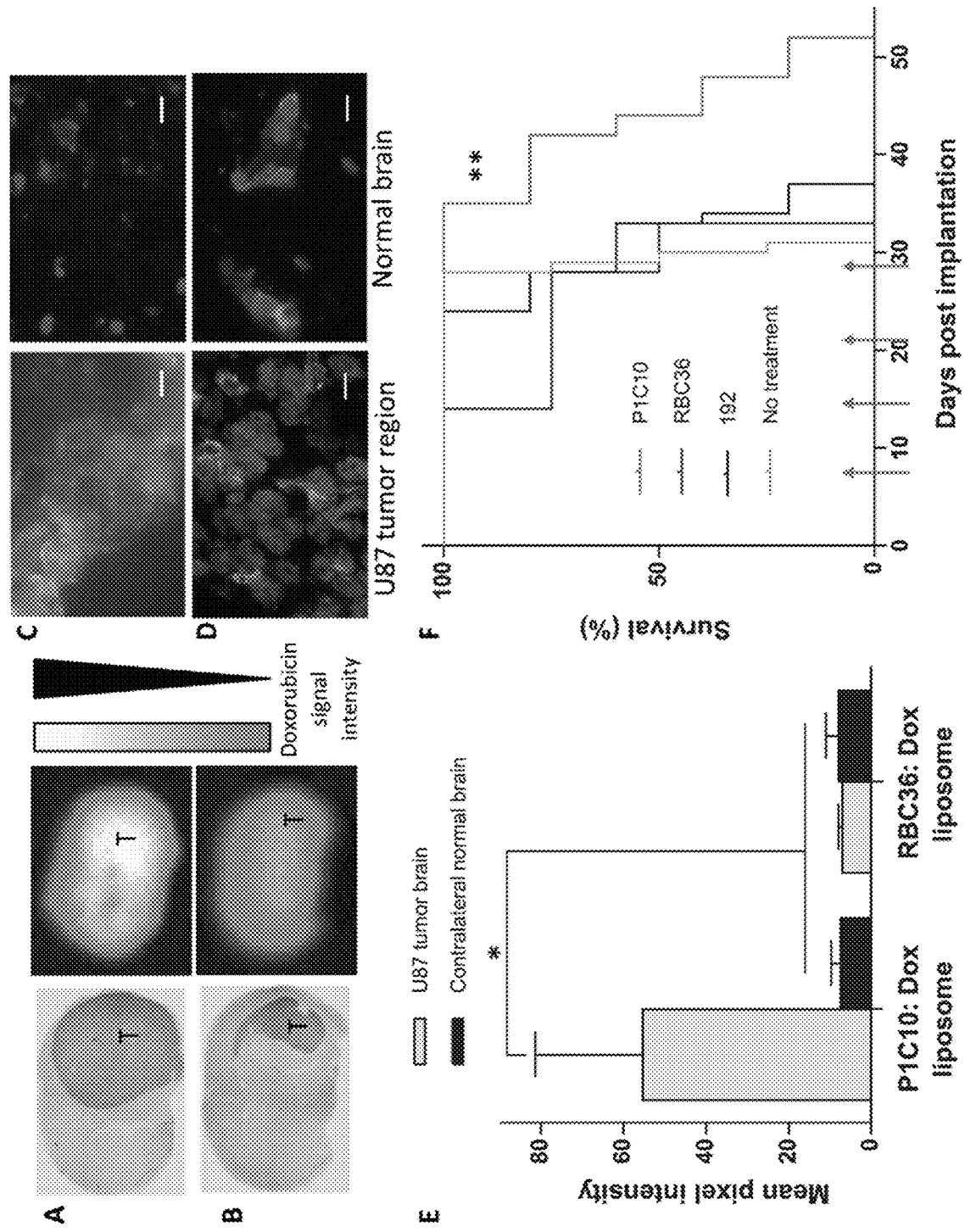
FIGS. 6A-6F. VLR targeting of doxorubicin-loaded liposomes in a GBM model. SCID mice bearing intracranial U87 tumors were intraperitoneally administered 12 mg doxorubicin/kg of VLR-targeted doxorubicin-loaded liposomes. (A) Accumulation of P1C10-targeted doxorubicin-loaded liposomes after 30 min of circulation. Representative H&E-stained murine brain bearing U87 glioma with the tumor region, dark blue and denoted with "T." The paired fluorescence image depicts doxorubicin fluorescence signal in an adjacent serial brain section. Yellow represents a stronger signal. (B) Accumulation of RBC36-targeted doxorubicin-loaded liposomes. Stained and imaged as in (A). (C) Accumulation of P1C10 or (D) RBC36-targeted doxorubicin-loaded liposomes was evaluated using doxorubicin fluorescence (green). GS-IB4 lectin labels microvessels (magenta), and cell nuclei are stained with Hoechst 33342 (blue). Doxorubicin accumulation was evaluated in the U87 tumor region and the contralateral normal brain. Scale bars, 20 µm. (E) Doxorubicin fluorescence signal, from groups presented in (C) and (D), is quantified for each group (*P<0.05, ANOVA). (F) P1C10-, 192-, or RBC36-targeted doxorubicin-loaded liposomes were administered once per week for 4 weeks (green arrows). The percentage of surviving mice was plotted for each group using Kaplan-Meier curves. P1C10 (n=5) targeting conferred a significant survival benefit compared to 192 (n=5), RBC36 (n=4), and nontreated (n=4) groups (**P<0.01, log-rank tests).
Figures 10A, 10B, 10C:
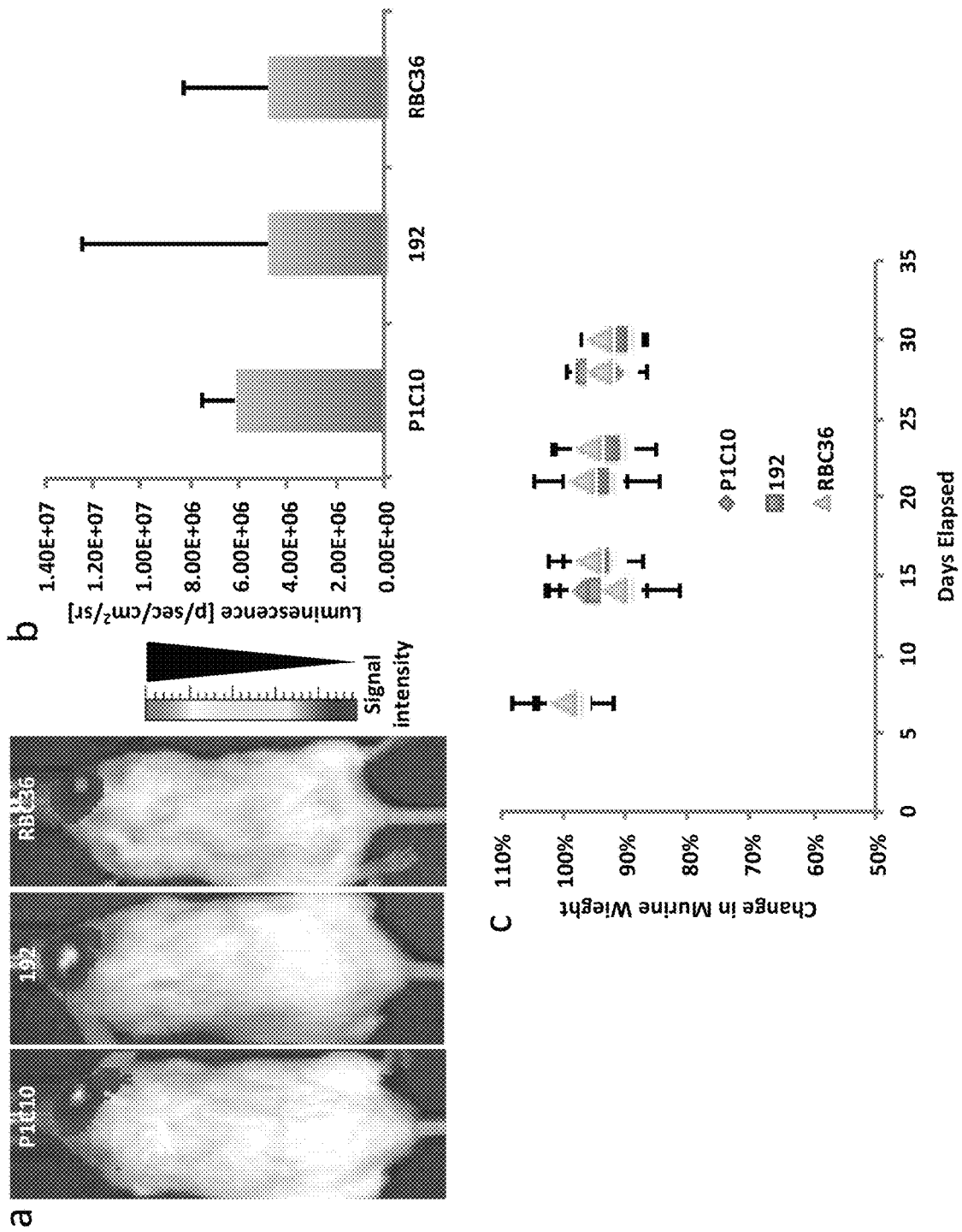
FIGS. 10A-10C. Luminescence and Weights from U87 Tumor Survival Experiment. (A) Representative, 7-day post implantation IVIS imager images of mice bearing luciferase-expressing U87 intracranial tumors. (B) Mean luminescence signal and standard deviation of IVIS image signal from day 7 brain tumors (ANVOA, p>0.05). (C) Murine weights are plotted as percentage of weight change from day 7 for each group, Mean±S.D. There are no statistically significant differences in weight between groups over time (p>0.05, ANOVA).

To demonstrate the potential therapeutic utility of targeting pathologically exposed brain ECM, we treated SCID mice bearing intracranial U87 GBM with P1C10-, 192-, or RBC36-targeted doxorubicin-loaded liposomes. For initial accumulation studies, tumor-bearing mice were administered one intraperitoneal dose of VLR-targeted doxorubicin liposomes, perfused, and then imaged for accumulated doxorubicin fluorescence. Whole-brain images of doxorubicin signal from mice treated with either P1C10- or RBC36-targeted doxorubicin liposomes show enhanced doxorubicin uptake with P1C10-targeted liposomes (FIGS. 6A-6B). Hematoxylin and eosin (H&E) staining of brain sections adjacent to sections used for fluorescent imaging demonstrates that the elevated doxorubicin signal was localized within tumor margins rather than contralateral normal brain. Higher-resolution fluorescent images indicate that P1C10 mediates an elevated doxorubicin accumulation within the tumor region compared to control contralateral brain tissue (7.6-fold increase) or the signal observed within the tumor region after exposure to control RBC36 (7.9-fold increase) (FIG. 6C-6E). These data correlate with the VLR brain distribution data (FIGS. 4A-4B), indicating that P1C10 mediates doxorubicin accumulation at the tumor site. To test therapeutic efficacy, we administered VLR-targeted liposomes to mice having detectable tumor burden 1 week after implantation (FIGS. 10A-10C). Four weekly therapeutic doses of 12 mg doxorubicin/kg of doxorubicin-loaded liposomes targeted by P1C10, 192, or RBC36 were administered by intraperitoneal injection at days 7, 14, 21, and 28. There were no significant differences in weight between groups (FIG. 10C). Median survivals after tumor implantation were 43, 30, and 28 days for P1C10-, 192-, and RBC36-targeted groups, respectively. The P1C10-targeted group demonstrated significantly improved survival compared to both the 192 and RBC36 control groups. Neither the 192 nor the RBC groups offered any survival benefit over a no-treatment control. These data indicate that targeting of pathologically exposed brain ECM with P1C10 can offer a therapeutic advantage versus perivascular targeting (192) or no targeting (RBC36).

Discussion

This study presents an approach for identifying VLRs that accumulate in pathologically exposed brain ECM for therapeutic targeting of brain diseases. We used VLRs rather than conventional targeting molecules such as immunoglobulins, peptides, or DARPins (29-31). As described earlier, VLRs have a leucine repeat structure, are smaller than immunoglobulins, have a large evolutionary distance from mammals, and have additional propensity to bind glycostructures (17-19, 32). All four of these features are desirable for identifying targeting ligands that accumulate in brain ECM. Whereas the unique structure and evolutionary distance expand the potential epitope range, the small size- and sugar-binding properties of VLRs could prove to be beneficial for accumulation and penetration into the tightly packed, glycosylated environment of brain ECM (27, 33). The novel, moderate throughput screening assay described in this study was suitable for identification of VLRs that specifically bind brain ECM. In particular, coupling an ECM biopanning protocol with a differential ECM-binding ELISA that simply used VLRs cleaved directly from the yeast surface enabled rapid identification of brain ECM-specific binders. In addition, the principles of this novel screening assay could be applied to identify targeting ligands that bind ECM derived from other organs or disease states.

Unlike typical therapeutic strategies that are designed to target disease-specific, cell-intrinsic markers (24), we show that targeting of pathologically exposed ECM could be effective in neurological diseases that exhibit differential BBB permeability such as GBM (6, 8, 9). Another advantage is that there are available techniques to artificially expose sequestered ECM via local BBB disruption such as targeted high-frequency focused ultrasound. To our knowledge, only two other recent studies have suggested targeting ECM as a strategy to treat neurological diseases. The first study identified a peptide that homed to traumatic brain injury (TBI) injury sites and appeared to selectively bind brain ECM associated with the TBI injury site (4). The second study generated CAR T cells targeted to chondroitin sulfate proteoglycan 4, which is reportedly overexpressed in brain tumor ECM (12). Both studies rely on targeting diseased ECM and are therefore likely best suited for treating diseases demonstrating these target-specific biomarkers. In contrast, the VLRs identified in our work bind normal brain ECM and strategically use the pathological exposure of normal ECM for targeting specificity. This approach could therefore obviate the need to identify a disease-specific target, and the ECM-targeting VLRs could be customized for any neurological disease that exhibits BBB disruption (or via artificial BBB disruption) by simply altering the therapeutic payload. Last, the initial immunohistochemical and biodistribution analyses with VLR clone P1C10 demonstrated high brain ECM specificity compared to peripheral tissues, indicating that brain ECM can serve as a "specific" target when coupled with pathological disruption of BBB properties. Thus, this strategy represents a significant departure from existing platforms that focus on targeting disease-related cell-intrinsic markers and/or schemes to circumvent the BBB. Specific targeting of BBB disruption could potentially reduce off-target effects compared with ligands that target overexpressed receptors as these proteins can also be expressed elsewhere in the body, although this would require further study.

This study used two different intracranial GBM murine models to demonstrate the functional relevance of targeting pathologically permeable BBB to deliver therapeutics. Implanting GL261 intracranially into C57BL/6 mice is a widely used immunocompetent syngeneic mouse GBM model for immunotherapy-related studies (26). In addition, implantable human-derived U87 GBM is a commonly used preclinical model, although the specific patient origin is unclear (24, 25, 34). Benefits include that it is a human tumor, has controlled tumor initiation, and can be implanted intracranially in SCID mice. Previous studies have demonstrated that treating U87 intracranial glioma with IL-13- or 2C5 nucleosome-recognizing, antibody-targeted, and doxorubicin-loaded liposomes significantly extended survival, with the IL-13 targeting leading to a partial cure (24, 25). Similarly, P1C10 targeting resulted in doxorubicin accumulation within GBM xenografts, reduced in vitro $EC_{50}$, and significantly improved survival. In contrast to the IL-13 study, we observed no cured animals after doxorubicin treatment. However, the unoptimized doxorubicin dosing and administration in our study is different from the previous IL-13 work, and IL-13 may also result in tumor cell endocytosis (35), which may confer superior efficacy compared to an ECM-targeted doxorubicin payload. We administered all treatment groups in this study equal amounts of VLR-conjugated, doxorubicin-loaded liposomes. Thus, the therapeutic benefit observed with P1C10 VLR is directly related to its specific targeting of disrupted BBB regions, and the biodistribution data suggest that the therapeutic benefit results from enhanced accumulation of doxorubicin selectively within the GBM. The survival benefit was only observed with P1C10, which displays diffuse parenchymal brain ECM binding, and not with the perivascular accumulating VLR 192. Additional studies comparing the P1C10 and 192 VLRs, as well as possible use of mass spectrometry or glycan arrays or other methods to identify the ECM antigenic components recognized by these VLRs, could offer insights into possible differences in therapeutic efficacy that may be based on actual delivered dose or differential localization.

Although GBM was used as a proof-of-concept neurological disease in this study since these tumors exhibit pathological BBB disruption and ECM exposure, it is important to note that recent studies demonstrate GBM tumors exhibit only partially disrupted BBB (6). The invasive tumor margins generally reside behind an intact BBB. Therefore, targeting pathologically permeabilized BBB with VLRs appears to be an effective strategy for delivering drug to the tumor core, but further work is needed to combine these VLRs with a therapeutic platform that is capable of spreading and inclusively targeting the clinically important invasive margin. Alternatively, techniques such as targeted high-frequency focused ultrasound or stereotactic radiation could further disrupt the BBB, potentially allowing brain ECM-binding VLRs to deliver therapeutics to the tumor margins. In addition, rather than targeting doxorubicin as in this proof-of-principle study, P1C10 VLR could be used to target and deliver more clinically relevant anti-GBM treatments such as temozolomide-loaded liposomes or immune checkpoint inhibitors (36, 37). To gather evidence for broad application and versatility of our approach, we envision extending our paradigm of delivering therapies via brain ECM targeting to additional disease models that show pathological exposure of brain ECM, including stroke, trauma, and neurodegenerative conditions. In addition, given the observed P1C10 accumulation after BBB disruption via hyperosmolar mannitol, it would be conceivable to use a combination of ECM-targeting VLRs and localized anatomical BBB disruption techniques such as high-frequency focused ultrasound to specifically target therapies to diseased brain regions that are associated with an intact BBB (27, 38). Although relatively low VLR immunogenicity has been reported in recent murine studies, VLRs would likely require humanization for future clinical applications, potentially by grafting antigen-binding domains onto human proteins that have a structurally homologous leucine repeat structure (39, 40). Last, with the potential of VLRs to target and deliver many different therapeutic payloads having various mechanisms of action, detailed toxicity testing for each VLR-payload combination will be necessary.

In conclusion, we present a proof-of-principle study for exploiting the pathological exposure of brain ECM for therapeutic benefit. Identification of VLRs and other targeting reagents that can target the pathological exposure of brain ECM and be combined with compatible therapeutic payloads may provide a new approach for treating many debilitating neurological diseases that currently lack effective treatments, including incurable GBM.

Materials and Methods

Experimental Design

Sample size. Sample sizes were dependent on the assay and are presented within the methods section for each assay.

Rules for stopping data collection. Data were collected at a predefined endpoint for each in vitro assay based on manufacturer's protocol or recommendations from literature. With murine survival studies, mice were euthanized in accordance with the Institutional Animal Care and Use Committee (IACUC) guidelines.

Data inclusion/exclusion criteria. Data generated for all assays were presented.

Outliers. No outliers were removed in this study.

Selection of endpoints. Study endpoints were predefined on the basis of the assay (please see methods sections below) and were not changed on the basis of outcomes.

Replicates. All in vitro assays were performed in multiple replicates as described within the methods section. Murine studies were powered as described below to measure statistically significant differences between groups.

Research objectives. The overall goal of this proof-of-concept study was to identify VLRs that bind normal brain ECM and demonstrate the functional ability of these VLRs to treat neurological pathologies that present with pathologic exposure of brain ECM.

Research subjects or units of investigation. NOD-SCID and C57BL/6 mice, bEnd.3 and 3T3 tissue-cultured cells, U87 and GL261 GBM cell lines, murine tissue sections (multiple organs), human brain sections, and human GBM sections were used in this study.

Experimental design. This study was a controlled laboratory experiment. Initial measurements were made using quantitative ELISA-based assays. Clones were validated using qualitative and quantitative in vitro assays and qualitative and quantitative murine studies.

Randomization. Mice were randomized into groups after intracranial implantation of U87 or GL261 GBM cells.

Blinding. Researchers were not blinded in this study given the limited number of individuals approved to perform murine assays making blinding impractical for this proof-of-concept study.

Cell Culture bEnd.3 cells [American Type Culture Collection (ATCC CRL-2299)] were cultured in Dulbecco's modified Eagle's medium (DMEM):F12 (1:1) supplemented with 10% fetal bovine serum (FBS). NIH/3T3 cells (ATCC CRL-1658) were cultured in DMEM supplemented with 10% FBS. Cultures were decellularized to expose ECM using nonenzymatic cell removal techniques. Namely, versene treatment (three washes at 37° C. for 10 min each) or three 10-min washes with 10 mM tris, 10 mM EDTA, and 1% Triton X-100 at 4° C., followed by 30-min incubation with deoxyribonuclease (0.2 mg/ml) in phosphate-buffered saline (PBS) with calcium and magnesium were used for decellularization (4, 41). Following decellularization, all plates were stored for a maximum of 6 months at 4° C. in PBS+1% bovine serum albumin (BSA) until use. U87-MG (ATCC HTB-14) cells were grown in DMEM supplemented with 10% FBS and passaged using accutase.

Yeast Culture

For VLR surface display assays, EBY100 yeast were grown in SD-CAA medium [dextrose (20.0 g/liter), yeast nitrogen base (6.7 g/liter), casamino acids (5.0 g/liter), $Na_2HPO_4 \cdot 7 H_2O$ (10.19 g/liter), and $NaH_2PO_4 \cdot H_2O$ (8.56 g/liter)] as previously described and induced when the culture reached an optical density at 600 nm ($OD_{600nm}$) between 0.8 and 0.9 using SG-CAA medium (21). Yeast was induced for 48 hours at room temperature before VLR or VLR-intein was harvested. For VLR secretion, YVH10 yeast transformed with pRS316-VLR-intein was grown in SD-2XSCAA+Trp [dextrose (20 g/liter), yeast nitrogenous base (6.7 g/liter), $Na_2HPO_4 \cdot 7H_2O$ (10.19 g/liter), $NaH_2PO_4 \cdot H_2O$ (8.56 g/liter), Arg (190 mg/liter), Met (108 mg/liter), Tyr (52 mg/liter), Ile (290 mg/liter), Lys (440 mg/liter), Phe (200 mg/liter), Glu (1260 mg/liter), Asp (400 mg/liter), Val (480 mg/liter), Thr (220 mg/liter), Gly (130 mg/liter), and Trp (40 mg/liter), lacking leucine and uracil]. Cultures were initiated, and then, cell density reset the following day to an $OD_{600nm}=0.1$ and grown for 72 hours at 30° C. Yeast were induced by replacing the medium with an equivalent volume of SG-2XSCAA+Trp [galactose replacing dextrose (20 g/liter)] containing 0.1% (w/v) BSA and culturing the cells for 72 hours at 20° C. Yeast supernatants were harvested, filtered through 0.22-μm PES (polyethersulfone) membranes, and dialyzed against tris-buffered saline (TBS) [25 mM tris, 300 mM NaCl, 2 mM KCl (pH 7.9)]. Imidazole (5 mM) plus 200 ml of the dialyzed supernant was gently mixed overnight at 4° C. with 1 ml of cobalt HisPur resin (Thermo Fisher Scientific). Beads were collected, washed with TBS plus 10 mM imidazole, and eluted with TBS plus 250 mM imidazole. Elutants were then buffer-exchanged into 50 mM HEPES [4-(2-hydroxyethyl)-

1-piperazineethanesulfonic acid] (pH 7.2) (removing the imidazole and neutralizing pH) using 10 K MWCO (10 kDa molecular weight cut-off) filters. Of note, regenerated cellulose membranes contain high amounts of thiols that induce nondesirable intein cleavage during isolation. We recommend using a PES membrane available through Pierce and Pall for buffer exchanges with secreted VLR-intein fusions before expressed protein ligation (EPL).

Combining Biopanning with Moderate Throughput ELISA-Based Screen

The VLR YSD library underwent two rounds of biopanning against bEnd.3 ECM to enrich for brain ECM-binding clones as previously described (20, 42). For the ELISA-based screen, selected biopanning clones were streaked out, and individual clones were picked into 96-well polypropylene plates. Clones were expanded at 30° C. overnight in SD-CAA medium and split into two plates (one plate for screening and one plate for frozen stock). The screening plate was induced at 20° C. using SG-CAA medium for 24 hours. VLR displaying yeast were washed with 50 mM HEPES (pH 7.2), and VLR was reduced off of the yeast surface using 20 µl of 50 mM MESNA solution in 50 mM HEPES (pH 7.2) for 45 min. Supernatants containing VLR were then diluted 1:10 with 50 mM HEPES (pH 7.2). Plates containing decellularized bEnd.3 or 3T3 ECM were blocked with 1% BSA and 1.5% goat serum in PBS and incubated with the HEPES-diluted VLRs for 1 hour at 37° C. Wells were washed five times with PBS+0.05% Tween 20. Next, an anti-myc antibody (9E10, BioLegend) modified with horseradish peroxidase (HRP) (1:1000) was added to each well and incubated for 45 min at room temperature. Wells were then washed seven times with PBS+0.05% Tween 20, 1 min per wash. VLR binding was detected by incubation with one-step 3,3',5,5'-tetramethylbenzidine (TMB) substrate for 15 to 30 min to develop signal. The reaction was stopped via acidification with 1 M HCl and quantified using absorbance signal at 450 nm. A blank well was included on every plate to establish background signal.

Affinity Measurement

To characterize VLR affinity for bEnd.3 ECM, dilutions of purified VLR were incubated with ECM. P1C10 VLR was diluted using a sixfold dilution scheme from 10 µM to 0.21 nM and then incubated with bEnd.3 ECM. Wells were washed five times with PBS+0.05% Tween 20 and then inubcated with anti-myc 9E10, 1:750, (BioLegend) and goat anti-mouse IgG modified with HRP. Wells were washed seven times with PBS+0.05% Tween 20 and then incubated with TMB substrate. Reaction was stopped after 15 min by acidification with 1 M HCl. Absorbance at 450 nm was quantified, and data were fit to a one-site equilibrium binding model to determine $K_d$ as previously described (43). The amino acid sequence for VLR P1C10 is (SEQ ID NO: 1)
ACPSQCSCDQTTVKCHSRRLTSVPAGIPTTTKILRLYSNQITKLEPGVF

DHLVNLEKLYISWNQLSALPVGVFDKLTKLTHLSLGYNQLKSVPRGAFD

NLKSLTHIWLLNNPWDCECSDILYLKNWIVQHASIVNLQGHGGVDNVKC

SGTNTPVRAVTEASTSPSKCP.

Manufacturing Cys-PEG3-Azide EPL Handle

Figure 11:
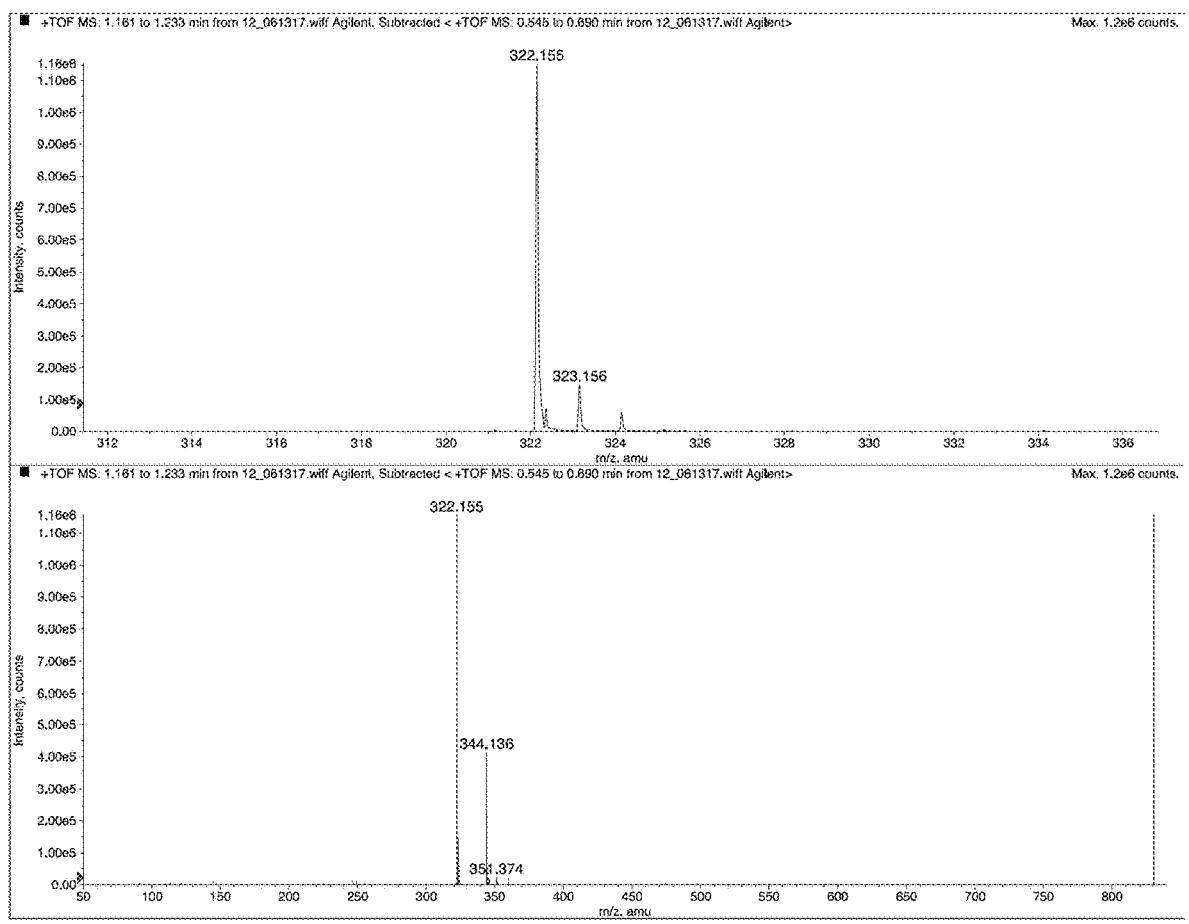
FIG. 11. Mass Spectrometry traces for Manufacture of Cys-PEG3-Azide. Amine-PEG3-Azide (Santa Cruz) was conjugated to the c-terminus of Cysteine using FMOC-Cys (Sassrin resin) OH (Bachem) using standard SPPS techniques. The peptide was purified to 90% purity by HPLC and Mass Spectrometry used determine formation of the desired product. Top panel shows the narrow mass range while bottom panel shows wide mass range. Expected mass for Cys-PEG3-Azide is 321 daltons.

Two hundred µM equivalents of Fmoc-Cys (SASRIN™ resin)-OH (Bachem) were swollen in N,N'-dimethylformamide (DMF) using two 30-min washes. Azido-PEG3-amine (1 mM; Santa Cruz Biotechnology), dissolved in DMF, was added, followed by NMM (4-N-methyl-morpholine) and HCTU [2-(6-Chloro-1H-benzotriazol-1-yl)-N,N,N',N'-tetramethylaminium hexafluorophosphate] for the activation of the amine. The reaction proceeded for 3 hours at room temperature. Resin was then washed nine times with DMF, two times with 20% piperidine for 15 min per wash, six times with DMF, and nine times with dichloromethane, dried for 10 min under $N_2$, and transferred to a desiccator overnight. The peptide was cleaved off the resin using 94% trifluoroacetic acid (TFA) with 2% TIPs (triisopropylsilane) for 3 hours. TFA was evaporated, and the peptide precipitated with cold ether. The Cys-PEG3-azide peptide sequence was confirmed with mass spectrometry (FIG. 11) and purified to >90% using high-performance liquid chromatography.

Intein EPL

To facilitate intein-mediated EPL of yeast-displayed VLRs, VLRs were cloned into the pCTre vector and fused to the engineered 202-08 intein using previously described methods (21, 22). For surface display experiments, 50 ml of yeast displaying VLR-intein fusion were pelleted, washed twice with 50 mM HEPES (pH 7.2), and then incubated with 200 mM MESNA in 50 mM HEPES (pH 7.2) (900 µl). This procedure reduces VLRs off the yeast surface and triggers the intein to form an unstable thioester. Immediately following MESNA addition, 5 mM 2mer peptide containing N-terminal cys and styrene handle was added to the yeast slurry (final volume, 1000 µl) (22). The mixture was incubated for 45 min at room temperature, and then, the yeast was pelleted. The supernatant was recovered and incubated at room temperature with shaking for an additional 2 to 18 hours to facilitate EPL. Buffer exchange of the VLR solution against PBS using 10 kDa MWCO filters removed MESNA and excess EPL ligand. Last, the tetrazine-Cy5 was incubated with VLR-styrene to facilitate covalent C-terminal modification of VLR and create VLR-Cy5 fusions. For secretion of intein-VLR fusions, VLRs were instead cloned into the pRS316 vector and fused to the 202-08 intein and produced and purified as noted in "Yeast culture" section above. Next, 200 mM MESNA was added to purified VLR-intein, followed by the addition of 5 mM Cys-PEG3-azide to produce VLR-azide fusions for liposome attachment. The mixture was incubated overnight at room temperature with gentle shaking. MESNA and excess EPL ligand were removed before use by buffer exchange with 10 kDa MWCO filters as described above. Western blots were used to characterize VLR-azide production. VLR samples were resolved on 4 to 12% bis-tris acrylamide and transferred to nitrocellulose using manufactures' protocols. Blots were probed using anti-FLAG antibody (M1 murine monoclonal, Sigma) to detect the N-terminal FLAG tag.

VLR-$IR_{800}$ Fusions

VLR-$IR_{800}$ was generated by creating VLR-azide using the intein-EPL reaction described above. After buffer exchange to remove MESNA and excess Cys-PEG3-azide, 5 mM DBCO-IR800 (LI-COR) was added to VLR fraction. Protein was shaken at 250 rpm, 30° C. for 90 min, to facilitate the bioorthogonal azide-DBCO reaction and yield VLR-$IR_{800}$. For GL261 imaging experiments, VLR-$IR_{800}$ (1 mg/kg) was intravenously administered to mice and allowed to circulate for 30 min before mice were perfused via cardiac puncture. Brains were resected, fixed in 4% paraformaldehyde, bisected, and imaged using a LiCor scanner. Serial sections were cut and stained with H&E to identify the tumor margins. n=3 per group was generated over two independent experimental days.

Mannitol Administration for Temporary BBB Disruption

Mannitol disruption was performed as previously described (23) with slight modification for this study. Briefly, C57BL/6 mice were anesthetized and then intravenously administered VLR-IR$_{800}$ (1 mg/kg). Five minutes after injection, 200 µl of 25% mannitol solution in water was administered intravenously (~2 mg/g mannitol). Exactly 9 min after mannitol administration, while the BBB was still permeable (23), mice were perfused with 20 ml of PBS via cardiac puncture. Brains were removed and imaged for retained IR$_{800}$ signal using a LiCor scanner. n=3 per group was generated over two independent experimental days.

VLR Rabbit Fc Fusions

VLRs were cloned into a pIRES vector and fused to rabbit Fc region (VLR-Fc). 293F cells (Life Technologies) were transfected with pIRES-VLR-Fc expression plasmids using 293fectin (Life Technologies), according to the manufacturer's protocol. Transfected 293F cells were grown for 3 days in FreeStyle (Life Technologies) media. VLR-Fc dimers were purified using protein A/G beads according to the manufacturer's protocol (Pierce).

Fluorescence Microscopy of Murine Specimens

Murine immunoflourescence techniques were used in two formats. First, VLRs directly reduced off of yeast surface were reoxidized and incubated with murine tissue sections, snap-frozen, and cut on a cryostat for 1 hour at room temperature. Sections were washed three times with PBS+ 1% BSA, 1.5% goat serum and incubated with a master mix containing anti-c-myc (rabbit) antibody (1:500; BioLegend), goat anti-rabbit AF555 antibody (1:1000; Life Technologies), and Isolectin GS-IB4 AF488 (1:400; Thermo Fisher Scientific) for 1 hour at room temperature. Sections were incubated with Hoechst 33342 (1:800) for the final 15 min of labeling. Sections were washed three times, fixed with 4% paraformaldehyde, and mounted for imaging. The second application was identical to the first except VLRs are directly labeled with Cy5 using intein EPL described above (22). Images were collected on a Zeiss Imager Z2 upright fluorescent microscope. For quantification, a minimum of three fields per group were quantified to determine VLR channel mean pixel intensity using ImageJ. Data are presented as mean pixel intensity±SD.

Fluorescence Microscopy of Human Specimens

Human brain samples were obtained from surgical resections as approved by the University of Wisconsin Institutional Review Board. Samples were snap-frozen and sectioned on a cryostat. For VLR staining, VLR-Cy5 was incubated with human brain sections (1:100; 1 mg/ml) for 1 hour at 37° C. Anti-CD31 (1:100; Cell Sciences) and goat anti-mouse AF488 (1:200; Thermo Fisher Scientific) were added to illuminate microvessels. Last, nuclei were stained with Hoechst 33342 (1:800). All human sections were imaged using a Leica SP8 3X STED microscope using confocal settings.

Generation and Characterization of VLR-Targeted Doxorubicin-Loaded Liposomes

Doxorubicin containing stealth liposomes decorated with VLR were produced. A lipid film containing 65% phosphatidylcholine, 32% cholesterol, 2.5% phosphatidylethanolamine-PEG2000, and 0.64% 1,2-distearoyl-sn-glycero-3-phosphoethanolamine-N-[dibenzocyclooctyl (polyethylene glycol)-2000] (DSPE-PEG2000-DBCO) (all lipids were from Avanti Polar Lipids) was created by dissolving lipids in 1:1 mixture of chloroform and methanol and removing solvent as previously described (28). Films were rehydrated in 155 mM $(NH_4)_2SO_4$ (pH 5.5) via vortexing and heating to >65° C., sonicated for 1 hour, and extruded through double-stacked 100-nm filters. Liposomes were buffer-exchanged into 123 mM Na citrate using PD-10 desalting columns and immediately mixed with 30 mg of doxorubicin/100 mg of lipid, at >65° C., to facilitate postformation loading. After ~1 hour at >65° C., liposomes were transferred to 4° C. overnight. The next day, free doxorubicin was removed using PD-10 desalting columns. Formation and size of liposomes were confirmed using dynamic light scattering (Malvern Zetasizer). To facilitate VLR decoration, VLR-azide was incubated with DBCO-containing liposomes for 90 min at 30° C. with shaking. VLR covalently bound to the liposome surface was detected by BCA (bicinchoninic acid assay) in nondoxorubicin-loaded liposomes (because doxorubicin contains a free amine) using the manufacturer's protocol (Pierce). Encapsulated doxorubicin was quantified by boiling liposomes with 1% Triton X-100 and measuring doxorubicin absorbance at 480 nm compared to a standard curve.

In Vitro U87 Cytotoxicity Assay bEnd.3 cells were grown to confluence in 96-well plates. Wells were decellularized to leave bEnd.3 ECM, as described above. Next, 1000 U87 cells per well were replated onto the U87 ECM and allowed to attach overnight. Wells were washed once with Opti-MEM and then incubated with a dilution series of P1C10- or RBC36-targeted doxorubicin-loaded liposomes. Liposomes were applied to the cell-ECM mixture in a dilution series from 80 µM to 0.3 nM, using fourfold dilutions (concentration calculated from doxorubicin 480-nm absorbance signal), using Opti-MEM as a diluent and incubated for 2 hours. Wells were washed two times with complete media and incubated for an additional 72 hours. CellTiter-Glo (Promega) was used to quantify the number of live cells, according to the manufacturer's protocol. $EC_{50}$ calculations were made using GraphPad software suite. To directly quantify VLR-doxorubicin binding to murine sections, P1C10-RBC36, or nontargeted doxorubicin-loaded liposomes were incubated with murine sections, washed and then imaged on a Zeiss Imager Z2 upright fluorescent microscope. A minimum of three fields per group were quantified to determine the VLR channel mean pixel intensity using ImageJ. Data are presented as mean pixel intensity±SD.

U87 Delivery and Survival Studies

All animal studies were approved by IACUC at the University of Wisconsin-Madison. Nonobese diabetic—severe combined immunodeficient mice underwent intracranial implantation of U87 cells expressing luciferase as previously described (44). Tumor engraftment was determined by quantifying luminescence using luciferin and an IVIS imager, according to manufacturer's protocols. For accumulation studies, tumors were grown until mice demonstrated tumor burden by displaying neurologic symptoms or hunched posture. For VLR-Fc studies, protein (3 mg/kg) was administered intravenously and allowed to circulate for 30 min. Mice were then perfused, and the organs were harvested. Organs were snap-frozen, embedded in OCT (optimal cutting temperature), and cut using a cryostat. Sections were stained with Isolectin GS-IB4 (1:400), Hoechst 33342 (1:800), and goat anti-rabbit AF555 (1:500) and then imaged on an upright Zeiss Imager Z2 fluorescent microscope. For doxorubicin accumulation studies, mice bearing U87 intracranial tumors received a single injection of P1C10- or RBC36-targeted doxorubicin-loaded liposomes intraperitoneally (12 mg doxorubicin/kg). Drug was allowed to circulate for 30 min, and then, mice were perfused with PBS and euthanized. Whole brains were bisected at the tumor site, and coronal images for doxorubicin fluorescence were taken using an IVIS imager (excitation, 465 nm; emission, 600 nm). Slices adjacent to the brain bisection used to expose the tumor were stained with H&E to define tumor margins and Isolectin GS-IB4+ Hoechst 33342 (1:400 and 1:800, respectively) for imaging on an upright Zeiss Imager Z2 fluorescent microscope. A minimum of three fields per group were quantified to determine the VLR channel mean pixel intensity using ImageJ.Data are presented as mean pixel intensity±SD. For survival studies, after confirming tumor engraftment by luminescence, mice were intraperitoneally administered 12 mg/kg doxorubicin of P1C10-targeted (n=5), 192-targeted (n=5), or RBC36-targeted (n=4) doxorubicin-loaded liposomes weekly for four cycles. Mice were monitored for neurological symptoms, hunched posture, and weight loss throughout the study and euthanized in accordance with guidelines of the IACUC protocol. The proportion of surviving mice over time was plotted using a Kaplan-Meier plot, and statistically significant differences were determined with log-rank tests.

Statistical Analysis

Statistical methods used in each assay are defined in detail within each respective figure legend. In general, data are presented and means±SD. The number of replicates used to generate these data is described in each method section. For murine survival studies, an n of 5 was chosen to power the study to observe a 30% survival difference between groups with 95% confidence.

REFERENCES

1. N. J. Abbott, A. A. K. Patabendige, D. E. M. Dolman, S. R. Yusof, D. J. Begley, Structure and function of the blood-brain barrier. Neurobiol. Dis. 37, 13-25 (2010).
2. G. McCaffrey, T. P. Davis, Physiology and pathophysiology of the blood-brain barrier: P-glycoprotein and occludin trafficking as therapeutic targets to optimize central nervous system drug delivery. J. Invest. Med. 60, 1131-1140 (2012).
3. A. Minagar, J. S. Alexander, Blood-brain barrier disruption in multiple sclerosis. Mult. Scler. 9, 540-549 (2003).
4. A. P. Mann, P. Scodeller, S. Hussain, J. Joo, E. Kwon, G. B. Braun, T. Molder, Z.-G. She, V. R. Kotamraju, B. Ranscht, S. Krajewski, T. Teesalu, S. Bhatia, M. J. Sailor, E. Ruoslahti, A peptide for targeted, systemic delivery of imaging and therapeutic compounds into acute brain injuries. Nat. Commun. 7, 11980 (2016).
5. J. K. Holodinsky, A. Y. X. Yu, Z. A. Assis, A. S. Al Sultan, B. K. Menon, A. M. Demchuk, M. Goyal, M. D. Hill, History, evolution, and importance of emergency endovascular treatment of acute ischemic stroke. Curr. Neurol. Neurosci. Rep. 16, 42 (2016).
6. P. R. Lockman, R. K. Mittapalli, K. S. Taskar, V. Rudraraju, B. Gril, K. A. Bohn, C. E. Adkins, A. Roberts, H. R. Thorsheim, J. A. Gaasch, S. Huang, D. Palmieri, P. S. Steeg, Q. R. Smith, Heterogeneous blood-tumor barrier permeability determines drug efficacy in experimental brain metastases of breast cancer. Clin. Cancer Res. 16, 5664-5678 (2010).
7. L. Lamsam, E. Johnson, I. D. Connolly, M. Wintermark, M. Hayden Gephart, A review of potential applications of MR-guided focused ultrasound for targeting brain tumor therapy. Neurosurg. Focus 44, E10 (2018).
8. B. Nico, D. Ribatti, Morphofunctional aspects of the blood-brain barrier. Curr. Drug Metab. 13, 50-60 (2012).
9. B. Obermeier, A. Verma, R. M. Ransohoff, The blood-brain barrier. Handb. Clin. Neurol. 133, 39-59 (2016).
10. D. R. Groothuis, The blood-brain and blood-tumor barriers: A review of strategies for increasing drug delivery. Neuro Oncol. 2, 45-59 (2000).
11. C. E. Brown, B. Badie, M. E. Barish, L. Weng, J. R. Ostberg, W.-C. Chang, A. Naranjo, R. Starr, J. Wagner, C. Wright, Y. Zhai, J. R. Bading, J. A. Ressler, J. Portnow, M. D'Apuzzo, S. J. Forman, M. C. Jensen, Bioactivity and safety of IL13Rα2-redirected chimeric antigen receptor CD8+ T cells in patients with recurrent glioblastoma. Clin. Cancer Res. 21, 4062-4072 (2015).
12. S. Pellegatta, B. Savoldo, N. Di Ianni, C. Corbetta, Y. Chen, M. Patané, C. Sun, B. Polio, S. Ferrone, F. DiMeco, G. Finocchiaro, G. Dotti, Constitutive and TNFα-inducible expression of chondroitin sulfate proteoglycan 4 in glioblastoma and neurospheres: Implications for CAR-T cell therapy. Sci. Transl. Med. 10, eaao2731 (2018).
13. R. L. Siegel, K. D. Miller, A. Jemal, Cancer statistics, 2015. CA Cancer J. Clin. 65, 5-29 (2015).
14. Q. T.Ostrom, H.Gittleman, J. Fulop, M. Liu, R. Blanda, C. Kromer, Y. Wolinsky, C. Kruchko, J. S. Barnholtz-Sloan, CBTRUS statistical report: Primary brain and central nervous system tumors diagnosed in the united states in 2008-2012. Neuro Oncol. 17 Suppl 4, iv1-iv62 (2015).
15. C. E. Brown, D. Alizadeh, R. Stan, L. Weng, J. R. Wagner, A. Naranjo, J. R. Ostberg, M. S. Blanchard, J. Kilpatrick, J. Simpson, A. Kurien, S. J. Priceman, X. Wang, T. L. Harshbarger, M. D'Apuzzo, J. A. Ressler, M. C. Jensen, M. E. Barish, M. Chen, J. Portnow, S. J. Forman, B. Badie, Regression of glioblastoma after chimeric antigen receptor T-cell therapy. N. Engl. J. Med. 375, 2561-2569 (2016).
16. G. F. Woodworth, G. P. Dunn, E. A. Nance, J. Hanes, H. Brem, Emerging insights into barriers to effective brain tumor therapeutics. Front. Oncol. 4, 126 (2014).
17. B. R. Herrin, M. D. Cooper, Alternative adaptive immunity in jawless vertebrates. J. Immunol. 185, 1367-1374 (2010).
18. B. W. Han, B. R. Herrin, M. D. Cooper, I. A. Wilson, Antigen recognition by variable lymphocyte receptors. Science 321,1834-1837 (2008).
19. P. Guo, M. Hirano, B. R. Herrin, J. Li, C. Yu, A. Sadlonova, M. D. Cooper, Dual nature of the adaptive immune system in lampreys. Nature 459, 796-801 (2009).
20. J. M. Lajoie, "Application of yeast surface display screening methods to antibody discovery and proteomics of the blood-brain barrier," thesis, University of Wisconsin Madison (2016).
21. C. J. Marshall, V. A. Grosskopf, T. J. Moehling, B. J. Tillotson, G. J. Wiepz, N. L. Abbott, R. T. Raines, E. V. Shusta, An evolved Mxe GyrA intein for enhanced production of fusion proteins. ACS Chem. Biol. 10, 527-538 (2015).
22. B. J. Umlauf, K. A. Mix, V. A. Grosskopf, R. T. Raines, E. V. Shusta, Site-specific antibody functionalization using tetrazine-styrene cycloaddition. Bioconjug. Chem. 29, 1605-1613 (2018).
23. D. M. McCarty, J. DiRosario, K. Gulaid, J. Muenzer, H. Fu, Mannitol-facilitated CNS entry of rAAV2 vector significantly delayed the neurological disease progression in MPS IIIB mice. Gene Ther. 16, 1340-1352 (2009).
24. A. B. Madhankumar, B. Slagle-Webb, X. Wang, Q. X. Yang, D. A. Antonetti, P. A. Miller, J. M. Sheehan, J. R. Connor, Efficacy of interleukin-13 receptor-targeted liposomal doxorubicin in the intracranial brain tumor model. Mol. Cancer Ther. 8, 648-654 (2009).

25. B. Gupta, V. P. Torchilin, Monoclonal antibody 2C5-modified doxorubicin-loaded liposomes with significantly enhanced therapeutic activity against intracranial human brain U-87 MG tumor xenografts in nude mice. Cancer Immunol. Immunother. 56, 1215-1223 (2007).
26. T. Oh, S. Fakumejad, E. T. Sayegh, A. J. Clark, M. E. Ivan, M. Z. Sun, M. Safaee, O. Bloch, C. D. James, A. T. Parsa, Immunocompetent murine models for the study of glioblastoma immunotherapy. J. Transl. Med. 12, 107 (2014).
27. E. Nance, K. Timbie, G. W. Miller, J. Song, C. Louttit, A. L. Klibanov, T.-Y. Shih, G. Swaminathan, R. J. Tamargo, G. F. Woodworth, J. Hanes, R. J. Price, Non-invasive delivery of stealth, brain-penetrating nanoparticles across the blood-brain barrier using MRI-guided focused ultrasound. J. Control. Release 189, 123-132 (2014).
28. B. P. Gray, M. J. McGuire, K. C. Brown, A liposomal drug platform overrides peptide ligand targeting to a cancer biomarker, irrespective of ligand affinity or density. PLOS ONE 8, e72938 (2013).
29. G. Winter, A. D. Griffiths, R. E. Hawkins, H. R. Hoogenboom, Making antibodies by phage display technology. Annu. Rev. Immunol. 12, 433-455 (1994).
30. D. Steiner, P. Forrer, A. Plückthun, Efficient selection of DARPins with sub-nanomolar affinities using SRP phage display. J. Mol. Biol. 382, 1211-1227 (2008).
31. K. C. Brown, Peptidic tumor targeting agents: The road from phage display peptide selections to clinical applications. Curr. Pharm. Des. 16, 1040-1054 (2010).
32. X. Hong, M. Z. Ma, J. C. Gildersleeve, S. Chowdhury, J. J. Barchi Jr., R. A. Mariuzza, M. B. Murphy, L. Mao, Z. Pancer, Sugar-binding proteins from fish: Selection of high affinity "lambodies" that recognize biomedically relevant glycans. ACS Chem. Biol. 8, 152-160 (2013).
33. D. J. Wolak, R. G. Thorne, Diffusion of macromolecules in the brain: Implications for drug delivery. Mol. Pharm. 10, 1492-1504 (2013).
34. M. Allen, M. Bjerke, H. Edlund, S. Nelander, B. Westermark, Origin of the U87MG glioma cell line: Good news and bad news. Sci. Transl. Med. 8, 354re3 (2016).
35. V. A. Kuznetsov, R. K. Puri, Kinetic analysis of high affinity forms of interleukin (IL)-13 receptors: Suppression of IL-13 binding by IL-2 receptor gamma chain. Biophys. J. 77, 154-172 (1999).
36. M. Preusser, M. Lim, D. A. Hafler, D. A. Reardon, J. H. Sampson, Prospects of immune checkpoint modulators in the treatment of glioblastoma. Nat. Rev. Neurol. 11, 504-514 (2015).
37. S.-S. Kim, A. Rait, E. Kim, J. DeMarco, K. F. Pirollo, E. H. Chang, Encapsulation of temozolomide in a tumor-targeting nanocomplex enhances anti-cancer efficacy and reduces toxicity in a mouse model of glioblastoma. Cancer Lett. 369, 250-258 (2015).
38. A. B. Etame, R. J. Diaz, C. A. Smith, T. G. Mainprize, H. K. Hynynen, J. T. Rutka, Focused ultrasound disruption of the blood brain barrier: A new frontier for therapeutic delivery in molecular neuro-oncology. Neurosurg. Focus 1, E3 (2012).
39. J.-j. Lee, H. J. Kim, C.-S. Yang, H.-H. Kyeong, J.-M. Choi, D.-E. Hwang, J.-M. Yuk, K. Park, Y. J. Kim, S.-G. Lee, D. Kim, E.-K. Jo, H.-K. Cheong, H.-S. Kim, A high-affinity protein binder that blocks the IL-6/STAT3 signaling pathway effectively suppresses non-small cell lung cancer. Mol. Ther. 22, 1254-1265 (2014).
40. D.-E. Hwang, J.-H. Ryou, J. R. Oh, J. W. Han, T. K. Park, H.-S. Kim, Anti-human VEGF repebody effectively suppresses choroidal neovascularization and vascular leakage. PLOS ONE 11, e0152522 (2016).
41. P. M. Crapo, T. W. Gilbert, S. F. Badylak, An overview of tissue and whole organ decellularization processes. Biomaterials 32, 3233-3243 (2011).
42. X. X. Wang, E. V. Shusta, The use of scFv-displaying yeast in mammalian cell surface selections. J. Immunol. Methods 304, 30-42 (2005).
43. M. L. Burns, T. M. Malott, K. J. Metcalf, B. J. Hackel, J. R. Chan, E. V. Shusta, Directed evolution of brain-derived neurotrophic factor for improved folding and expression in Saccharomyces cerevisiae. Appl. Environ. Microbiol. 80, 5732-5742 (2014).
44. K. I. Swanson, P. A. Clark, R. R. Zhang, I. K. Kandela, M. Farhoud, J. P. Weichert, J. S. Kuo, Fluorescent cancer-selective alkylphosphocholine analogs for intraoperative glioma detection. Neurosurgery 76, 115-124 (2015).

Each publication, patent, and patent publication cited in this disclosure is incorporated in reference herein in its entirety. The present invention is not intended to be limited to the foregoing examples, but encompasses all such modifications and variations as come within the scope of the appended claims.

We claim:

1. An isolated polypeptide comprising a variable lymphocyte receptor (VLR) comprising the six following regions:

(i)
                              SEQ ID NO: 11
    (TVKCHS), (ii)
                              SEQ ID NO: 12
    (ILRLYS), (iii)
                              SEQ ID NO: 13
    (KLYISW), (iv)
                              SEQ ID NO: 14
    (HLSLGY), (v)
                              SEQ ID NO: 15
    (HIWLLN),
    and (vi)
                              (SEQ ID NO: 8)
    (SIVNLQGHGGVD), wherein the isolated polypeptide is able to specifically bind to brain extracellular matrix (ECM) in vivo.

2. The isolated polypeptides of claim 1, wherein the VLR comprises SEQ ID NO:10.

3. The isolated polypeptide of claim 1, wherein the VLR comprises SEQ ID NO: 16 or a sequence having at least 98% identity with SEQ ID NO:16.

4. The isolated polypeptides of claim 1, wherein the VLR is selected from the group consisting of P1C10 (SEQ ID NO:1) and an amino acid sequence with at least 98% sequence identity to SEQ ID NO:1.

5. The isolated polypeptide of claim 1, wherein the polypeptide is directly or indirectly linked to an agent.

6. The isolated polypeptide of claim 5, wherein the agent is selected from the group consisting of a therapeutic agent, a pharmaceutical agent, a diagnostic agent, an imaging agent, a detection agent-, an immunological therapeutic construct, and a combination thereof.

7. The isolated polypeptide of claim 6, wherein the agent is a therapeutic agent or a pharmaceutical agent.

8. The isolated polypeptide of claim 6, wherein the agent is a diagnostic agent, a detection agent, or a combination thereof.

9. The isolated polypeptide of claim 5, wherein the agent is a peptide agent, and wherein the VLR and the peptide agent are portions of a fusion protein.

10. The isolated polypeptide of claim 5, wherein the agent is an Fc region of an antibody.

11. The isolated polypeptide of claim 10, wherein the VLR and the Fc region form a fusion protein.

12. The isolated polypeptide of claim 10, wherein the Fc region is a human Fc region.

13. The isolated polypeptide of claim 12, wherein the Fc region is from human IgG.

14. A brain ECM targeting composition comprising the isolated polypeptide of claim 1 and a pharmaceutically acceptable carrier.

15. The brain ECM targeting composition of claim 14, wherein the composition further comprises a drug-loaded carrier conjugated to the isolated polypeptide.

16. The brain ECM targeting composition of claim 15, wherein the drug-loaded carrier is a liposomes.

17. The brain ECM targeting composition of claim 15, wherein the drug-loaded carrier is loaded with a chemotherapeutic drug.

18. The brain ECM targeting composition of claim 17, wherein the chemotherapeutic drug is doxorubicin, temozolomide or a checkpoint inhibitor.

19. An isolated nucleic acid encoding the isolated polypeptide of claim 1.

20. A vector encoding the isolated polypeptide of claim 1.

21. A cell able to express the isolated polypeptide of claim 1.

22. A method of targeting an agent to brain ECM, the method comprising:
   (a) administering to the subject the isolated polypeptide of claim 1 directly or indirectly linked to an agent, or
   (b) administering to the subject a brain ECM targeting composition comprising the isolated polypeptide of claim 1 directly or indirectly linked to the agent.

23. The method of claim 22, wherein the agent is able to treat a neurological disease associated with disruption of the blood brain barrier.

24. The method of claim 23, wherein the disease is glioblastoma.

25. The method of claim 22, wherein the agent is a therapeutic agent or a pharmaceutical agent.

26. The method of claim 25, wherein the isolated polypeptide is conjugated to a carrier containing the therapeutic agent or the pharmaceutical agent.

27. A method of treating a disease or injury associated with blood brain barrier disruption in a subject in need thereof, the method comprising
   (a) administering to the subject the isolated polypeptide of claim 1 directly or indirectly linked to a therapeutic agent, or
   (b) administering to the subject a brain ECM targeting composition comprising the isolated polypeptide or of claim 1 directly or indirectly linked to a therapeutic agent,
   in an amount effective to treat the disease or injury in the subject.

28. The method of claim 27, wherein the isolated polypeptide or composition is administered to the subject systemically.

29. The method of claim 27, wherein the disease is cancer.

30. The method of claim 29, wherein the cancer is glioblastoma.

* * * * *

UNITED STATES PATENT AND TRADEMARK OFFICE
CERTIFICATE OF CORRECTION

PATENT NO. : 12,077,609 B2
APPLICATION NO. : 17/414581
DATED : September 3, 2024
INVENTOR(S) : Eric V. Shusta et al.

It is certified that error appears in the above-identified patent and that said Letters Patent is hereby corrected as shown below:

On the Title Page

(72) Inventors:, "John Kuo" should be --John Shu-Shin Kuo--.

In the Specification

Column 2, Line 17, "(XYXSW(x)$_{18}$" should be --(KXYXSW(X)$_{18}$--.

Column 28, Line 58, "Yeast supemants" should be --Yeast supernants--.

Column 34, Line 12, "Polio" should be --Pollo--.

Column 34, Line 26, "Stan" should be --Starr--.

Column 35, Line 6, "Fakumejad" should be --Fakurnejad--.

In the Claims

Claim 2, Column 61, Line 28, "polypeptides" should be --polypeptide--.

Claim 4, Column 61, Line 33, "polypeptides" should be --polypeptide--.

Claim 16, Column 62, Line 10, "liposomes" should be --liposome--.

Claim 27, Column 62, Line 46, "polypeptide or of" should be --polypeptide of--.

Signed and Sealed this
Tenth Day of December, 2024

Katherine Kelly Vidal
*Director of the United States Patent and Trademark Office*